US010208033B2

(12) United States Patent
Wang et al.

(10) Patent No.: US 10,208,033 B2
(45) Date of Patent: Feb. 19, 2019

(54) β-CARBOLINE, DIHYDRO-β-CARBOLINE AND TETRAHYDRO-β-CARBOLINE ALKALOID DERIVATIVES AND PREPARATION METHODS SAME AND USE IN ASPECTS OF PREVENTING AND TREATING PLANT VIRUSES, FUNGICIDES AND INSECTICIDES

(71) Applicants: NANKAI UNIVERSITY, Tianjin (CN); NATIONAL PESTICIDE ENGINEERING RESEARCH CENTER (TIANJIN), Tianjin (CN)

(72) Inventors: Qingmin Wang, Tianjin (CN); Hongjian Song, Tianjin (CN); Yongxian Liu, Tianjin (CN); Yuxiu Liu, Tianjin (CN)

(73) Assignees: NANKAI UNIVERSITY, Tianjin (CN); NATIONAL PESTICIDE ENGINEERING RESEARCH CENTER (TIANJIN), Tianjin (CN)

( * ) Notice: Subject to any disclaimer, the term of this patent is extended or adjusted under 35 U.S.C. 154(b) by 0 days.

(21) Appl. No.: 15/109,371

(22) PCT Filed: Dec. 24, 2014

(86) PCT No.: PCT/CN2014/094847
§ 371 (c)(1),
(2) Date: Jun. 30, 2016

(87) PCT Pub. No.: WO2015/101206
PCT Pub. Date: Jul. 9, 2015

(65) Prior Publication Data
US 2016/0326166 A1 Nov. 10, 2016

(30) Foreign Application Priority Data
Dec. 30, 2013 (CN) .......................... 2013 1 0752240

(51) Int. Cl.
*A01N 43/90* (2006.01)
*C07D 471/04* (2006.01)

(52) U.S. Cl.
CPC ........... *C07D 471/04* (2013.01); *A01N 43/90* (2013.01)

(58) Field of Classification Search
CPC .............................. A01N 43/90; C07D 471/04
USPC .......................................................... 546/85
See application file for complete search history.

(56) References Cited

U.S. PATENT DOCUMENTS

2009/0227619 A1  9/2009  Wu et al.

FOREIGN PATENT DOCUMENTS

| CN | 1358720 A | 7/2002 |
|---|---|---|
| CN | 1743326 A | 3/2006 |
| CN | 101020688 A | 8/2007 |
| WO | 97/37658 A1 | 10/1997 |

OTHER PUBLICATIONS

Song et al., Design, Synthesis, Anti-TMV, Fungicidal, and Insecticidal Activity Evaluation of 1,2,3,4-Tetrahydro-Beta-Carboline-3-Carboxylic Acid Derivatives Based on Virus Inhibitors of Plant Sources, Bioorganic & Medicinal Chemistry Letters, vol. 24, No. 22, pp. 5228-5233, Sep. 2014.*
Song et al., Synthesis and Antiviral and Fungicidal Activity Evaluation of Beta-Carboline, Dihydro-Beta-Carboline, Tetrahydro-Beta-Carboline Alkaloids, and Their Derivatives, Journal of Agricultural and Food Chemistry, vol. 62, No. 5, pp. 1010-1018, Jan. 2014.*
Liu et al., Design, Synthesis, nand Antiviral, Fungiciidal, and Insecticidal Activities of Tetrahydro-beta-Carboline-3-Carbohydrazide Derivatives, Journal of Agricultural and Food Chemistry, vol. 62, No. 41, pp. 9987-9999, 2014.*
Yao et al., A Class of Oral N-[(1S,3S)-1-Methyl-1,2,3,4-Tetrahydro-beta-Carboline-3-Carbonyl]-N'-(amino-acid-acyl)hydrazine: Discovery, Synthesis, in vitro Anti-Platelet Aggregation/in vivo Anti-Thrombotic Evaluation and 3D QSAR Analysis, European Journal of Medicinal Chem. vol. 46, No. 8, pp. 3237-3249, 2011.*
Fu et al., "Primary study on antifungal activity of peganum harmala extracts," Grassland and Turf (Bimonthly) 2008, No. 1 (Sum No. 126) 44-48 (English Abstract provided).
Lu et al., "Synthesis and Antibacterial Activties of beta-Carboline Oxime Esters Compounds," Chinese Journal of Synthetic Chemistry, 2011, vol. 19, No. 6, 769-772 (English Abstract provided).
Cai et al., "Synthesis and Antibacterial Activities of Novel 1-Trifluoromethyl-phenyl-beta-carboline-3-carbonyl-diacylhydrazine," Chinese Journal of Synthetic Chemistry, 2012, vol. 20, No. 6, 736-739 (English Abstract provided).
Xiaomeng et al., "The Research of the Pesticidal Activity on Different Peganum harmala Extractions," Chinese Agricultural Science Bulletin, 2005, vol. 21, No. 4, 278-279 (English Abstract provided).
Zeng et al., "Cytotoxic and Insecticidal Activities of Derivatives of Harmine, a Natural Insecticidal Component Isolated from Peganum harmala," Molecules 2010, 15, 775-7791.
Chen et al., "Tobacco Mosaic Virus (TMV) Inhibitors from Picrasma quassioides Benn," J. Agric. Food Chem. 2009, 57, 6590-6595.

(Continued)

*Primary Examiner* — Brenda L Coleman
(74) *Attorney, Agent, or Firm* — Volpe amd Koenig, P.C.

(57) ABSTRACT

The present invention relates to β-carboline, dihydro-β-carboline and tetrahydro-β-carboline alkaloid derivatives (I) and a method for preparing same and the use in the aspects of preventing and treating plant viruses, fungicides and insecticides. For the meaning of each group in formula (I) see the description. The β-carboline, dihydro-β-carboline and tetrahydro-β-carboline alkaloid derivatives of the present invention show a particularly ourstanding anti-plant virus activity, and also have fungicidal and insecticidal activities.

9 Claims, No Drawings

(56) References Cited

OTHER PUBLICATIONS

Bloomquist et al., "Mode of Action of beta-Carboline Convulsants on the Insect Nervous System and Their Potential as Insecticides," Pestic. Sci. 1997, 51, 1-6.

El-Gengaihi et al., "Chemical and biological investigation of harmal plant. 2. Alkaloidal investigation," J. Appl. Ent. 121, 165-167 (1997).

Weng et al., "Synthesis and Herbicidal Activity Evaluation of Novel beta-Carboline Derivatives," Molecules 2012, 17, 3969-3980.

* cited by examiner

β-CARBOLINE, DIHYDRO-β-CARBOLINE AND TETRAHYDRO-β-CARBOLINE ALKALOID DERIVATIVES AND PREPARATION METHODS SAME AND USE IN ASPECTS OF PREVENTING AND TREATING PLANT VIRUSES, FUNGICIDES AND INSECTICIDES

CROSS REFERENCE TO RELATED APPLICATIONS

This application is a 35 USC § 371 national stage application of PCT/CN2014/094847, which was filed Dec. 24, 2014 and claims priority to Chinese Patent Application No. 201310752240.2, filed Dec. 30, 2013, entitled "β-Carboline, Dihydro-β-Carboline and Tetrahydro-β-Carboline Alkaloid Derivatives and Preparation Methods Same and Use in Aspects of Preventing and Treating Plant Viruses, Fungicides and Insecticides," both of which are incorporated specifically and entirely herein by reference as if fully set forth.

FIELD OF THE INVENTION

The present invention relates to β-carboline, dihydro-β-carboline and tetrahydro-β-carboline alkaloid derivatives and their preparation methods and use in the preventing and treating plant viruses fungicides and insecticides and pertains to the technical field of pesticides.

BACKGROUND OF THE INVENTION

The skeleton structures of β-carboline, dihydro-β-carboline and tetrahydro-β-carboline widely exist in natural products and drug molecules. Harmine and tetrahydroharmine belong to β-carboline and tetrahydro-β-carboline alkaloids respectively and are representative compounds of harmala alkaloids. Harmine was first separated from *P. harmala* L. This alkaloid shows cytotoxicity to leukemia cell lines HL60 and K562. Tetrahydroharmine is a fluorescent molecule separated from Malpighiaceae plant *Banisteriopsis caapi*. This compound has weak inhibition to the re-uptake of 5-hydroxytryptamine. Harmaline is an agonist of the central nervous system and a reversible inhibitor of monoamine oxidase (MAO-A).

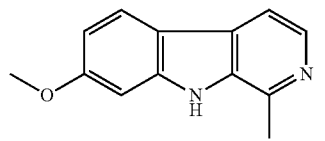

Harmine

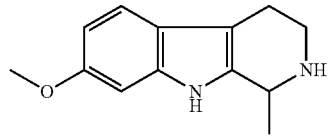

Tetrahydroharmine

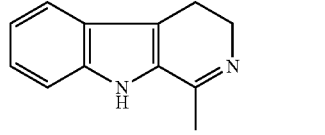

Harmaline

Currently, the research on β-carboline, dihydro-β-carboline and tetrahydro-β-carboline and substances similar to them focuses on anti-tumor, killing of human parasites and monoamine oxidase inhibitors. However, as far as we know, no document reports the activity of β-carboline, dihydro-β-carboline and tetrahydro-β-carboline and substances similar to them against plant viruses, and little was reported on their bactericidal activity and insecticidal activity. In the aspect of bactericidal activity: Fu Haibo et al from Gansu Agricultural University researched and found in 2007 that the extracting solutions of *P. harmala* L. in different solvents all have certain inhibiting effect to spore germination of four kinds of pathogenic bacteria, including *Botrytis cinerea, Fusarium oxysporum, Alternaria solani* and *Cladosporium cucumerinum* Ellis et Arthur, and their $EC_{50}$ is 0.060, 0.199, 0.105 and 0.223 g/mL respectively (Fu Haibo, Ding Defang, Zhao Hongmei, Yang Shunyi, Grassland and Lawn, 2008, 1, 44-48); in 2007, Wen Ren et al from Fudan University reported derivatives with a structure of 1-(3-indol)-1,2,3,4-tetrahydro-β-carboline and researched the in vitro activity of these derivatives against *Pyricularia oryzae* (CN101020688); in 2011, Zhang Yaomou et al from South China Agricultural University reported compounds with a structure of β-carboline-3-oxime ester and meanwhile studied the inhibitory activity of these compounds against *Colletotrichum musae, Colletotrichum gloeosporioides* and tomato late plight (Lu Shaoying, Zhang Yaomou, Synthetic Chemistry, 2011, 19 (6), 769-772); in 2012, this research group again reported compounds with a structure of 1-p-trifluoromethylphenyl-β-carboline-3-carbonyl bishydrazide, but the quantity of the compounds was small and their bacteriostatic activity against Rhizoctorzia *solani* was tested only (Cai Ying, Huang Jianfeng, Zhang Meidan, Zeng Yong, Zhang Yaomo, Synthetic Chemistry, 2012, 20(6), 736-739.). In the aspect of insecticidal activity: in 2005, Zhao Xiaomeng et al from Beijing University of Agriculture reported the contact activity of the ethanol extract, chloroform extract and water extract of the overground part of *P. harmala* L. in the growing period against *Myzus persicae, Macrosiphum rosivorum* and *Tetranychus cinnabarinus*. The result is that their contact activity against spider mites is all above 95% at concentration of 10 mg/mL, and that against two kinds of aphids is above 70% at concentration of 10 mg/mL (Zhao Xiaomeng, Zeng Zhaohai, Chinese Agricultural Science Bulletin, 2005, 21(4), 278-279); in 2010, Zhong Guohua et al from South China Agricultural University reported the insecticidal activity of 1,3-disubstituted β-carboline and tetrahydro-β-carboline derivatives against *culex pipiens* larvae and *Lipaphis erysimi*. To be specific, the $LC_{50}$ of the compounds with a structure of 1-phenyl substituted β-carboline and tetrahydro-β-carboline-3-methyl ester against *culex pipiens* larvae is 20.82 mg/L and 23.98 mg/L respectively, and the $LC_{50}$ against *Lipaphis erysimi* is 53.16 mg/L and 68.05 mg/L respectively (Zeng, Y; Zhang, Y M.; Weng, Q. F.; Hu, M. Y.; Zhong G H. *Molecules* 2010, 15, 7775-7791).

SUMMARY OF THE INVENTION

The object of the present invention is to provide β-carboline, dihydro-β-carboline and tetrahydro-β-carboline alkaloid derivatives and their preparation methods and use in the preventing and treating plant viruses and killing of bacteria and insects. The β-carboline, dihydro-β-carboline and tetrahydro-β-carboline alkaloid derivatives described in the present invention show very good activity against plant viruses and also show bactericidal activity and insecticidal activity. The β-carboline, dihydro-β-carboline and tetrahydro-β-carboline alkaloid derivatives described in the present invention are compounds with a structure shown in the following general formula (I):

General formula (I)

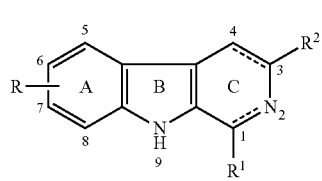

The β-carboline, dihydro-β-carboline and tetrahydro-β-carboline alkaloid derivatives (I) described in the present invention are compounds with structures shown in the following four general formulas ($I_a$, $I_b$, $I_c$, $I_d$):

General formula ($I_a$)

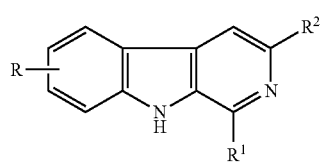

General formula ($I_b$)

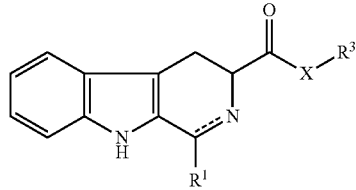

General formula ($I_c$)

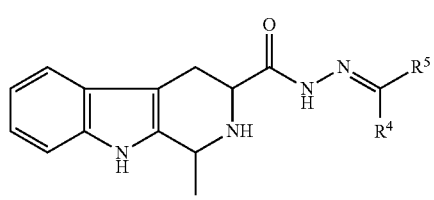

General formula ($I_d$)

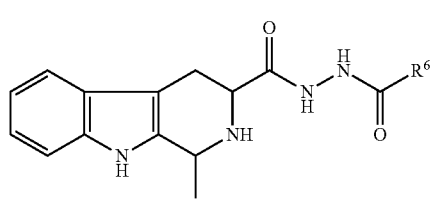

The β-carboline, dihydro-β-carboline and tetrahydro-β-carboline alkaloid derivatives (I) described in the present invention further comprise natural compounds with structures shown in the following formulae:

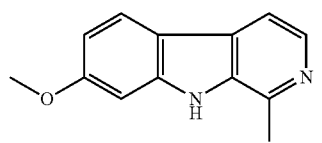

Harmine

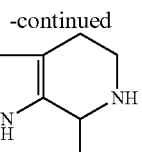

Tetrahydroharmine

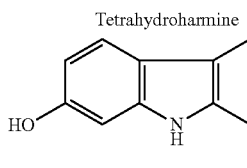

Harmol

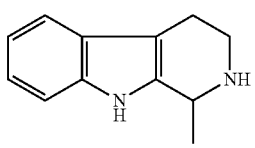

Harmane      Tetrahydroharmane

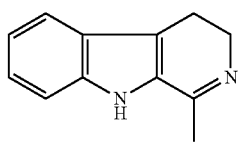

Harmalan

The dihydro-β-carboline alkaloid described in the present invention may be prepared by the following method (Path 1): firstly introducing aldehyde group to indol 3-site to obtain compound 1, the compound 1 then reacts with nitromethane and ammonium acetate to obtain intermediate 2, the intermediate 2 is reduced to obtain tryptamine 3, and then the tryptamine 3 is acylated and cyclized to obtain dihydro-β-carboline alkaloid harmalan.

Path 1:

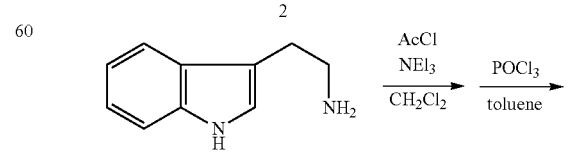

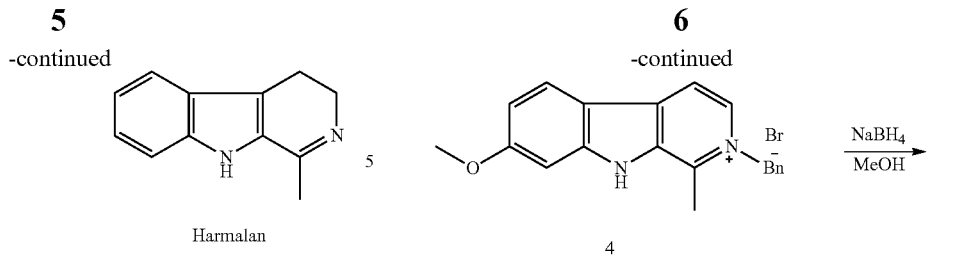

Harmalan

The β-carboline and tetrahydro-β-carboline alkaloid described in the present invention may be prepared by the following method (Path 2): firstly, reacting tryptamine 3 with an acetaldehyde aqueous solution under the catalysis of sulfuric acid to obtain tetrahydro-β-carboline alkaloid tetrahydroharmane, which is then further dehydrogenated by one step and oxidized to obtain β-carboline alkaloid harmane.

Path 2:

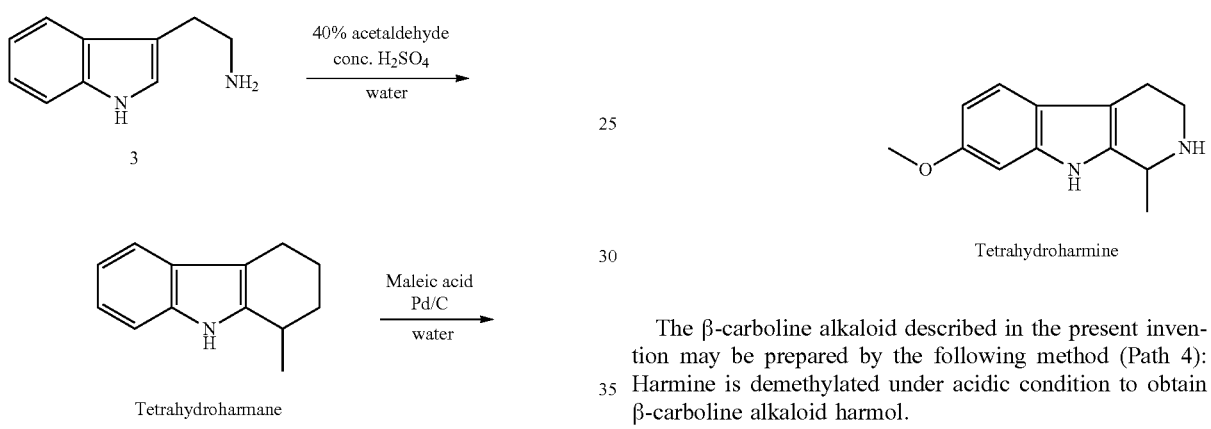

The tetrahydro-β-carboline alkaloid described in the present invention may be prepared by the following method (Path 3): firstly, reacting harmine with benzyl bromide to obtain quaternary ammonium salt 4, which is then reduced to obtain compound 5; lastly, the compound 5 is hydrogenated under the catalysis of Pd/C to obtain tetrahydro-β-carboline alkaloid tetrahydroharmine.

Path 3:

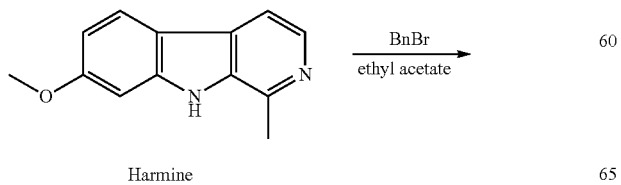

Harmine

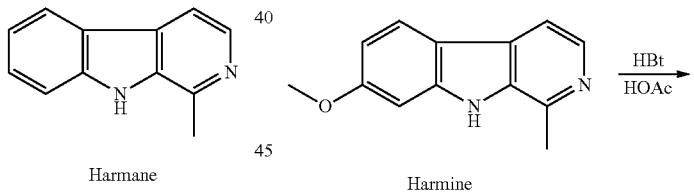

Tetrahydroharmine

The β-carboline alkaloid described in the present invention may be prepared by the following method (Path 4): Harmine is demethylated under acidic condition to obtain β-carboline alkaloid harmol.

Path 4:

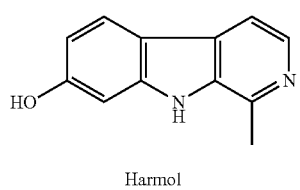

Harmol

The β-carboline alkaloid derivatives ($I_a$) described in the present invention may be prepared by the following method (Path 5): reacting Harmane with bromosuccinimide under acidic condition to obtain compounds $I_a$-1 and $I_a$-2, and reacting the obtained compounds with sodium nitrate under acidic condition to obtain compounds $I_a$-3 and $I_a$-4 containing substituted nitro on phenyl ring.

Path 5:

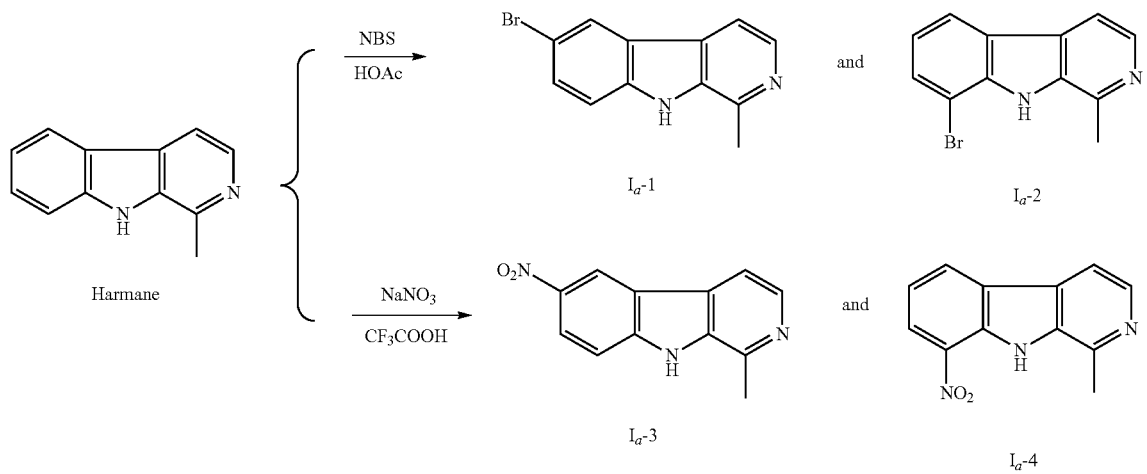

The β-carboline alkaloid derivatives (I) described in the present invention may be prepared by the following method (Path 6): reacting Harmol with isocyanate to obtain compound $I_a$-5, reacting Harmol with acyl chloride to obtain compound $I_a$-6-$I_a$-8, and reacting Harmol with amino acid in presence of a condensation agent to obtain compound $I_a$-9.

Path 6:

reacting L-tryptophan with an acetaldehyde aqueous solution to obtain cyclization product $I_b$-1, which is then further esterified by one step to obtain compound $I_b$-13. Compound $I_b$-13 is dehydrogenated and oxidized to obtain compound $I_a$-10. Compound $I_a$-10 is hydrolyzed under alkaline condition to obtain compound $I_a$-11. Compound $I_a$-10 is reduced by lithium aluminum hydride to obtain compound $I_a$-12. The

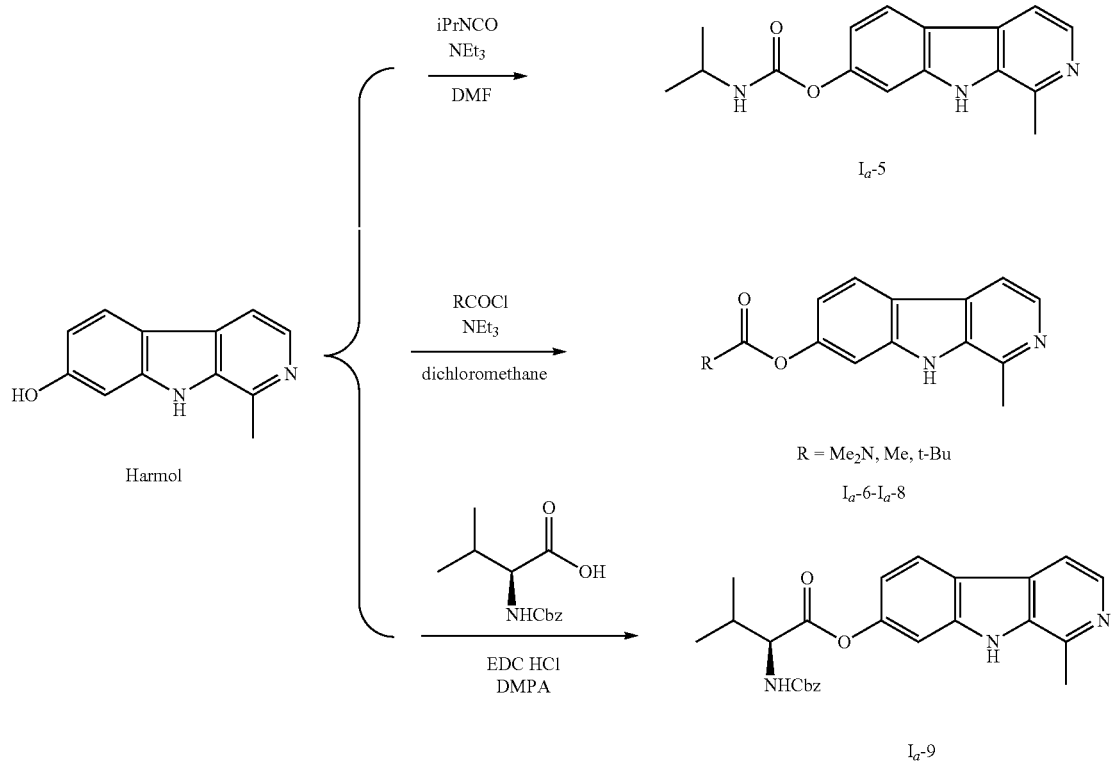

The β-carboline and tetrahydro-β-carboline alkaloid derivatives ($I_a$ and $I_b$) described in the present invention may be prepared by the following method (Path 7): firstly, compound is oxidized to obtain aldehyde $I_a$-13. Compound $I_a$-13 reacts with malonic acid to obtain acrylic acid $I_a$-14. By a same path, compound $I_a$-15-$I_a$-16 can be synthesized.

Path 7:

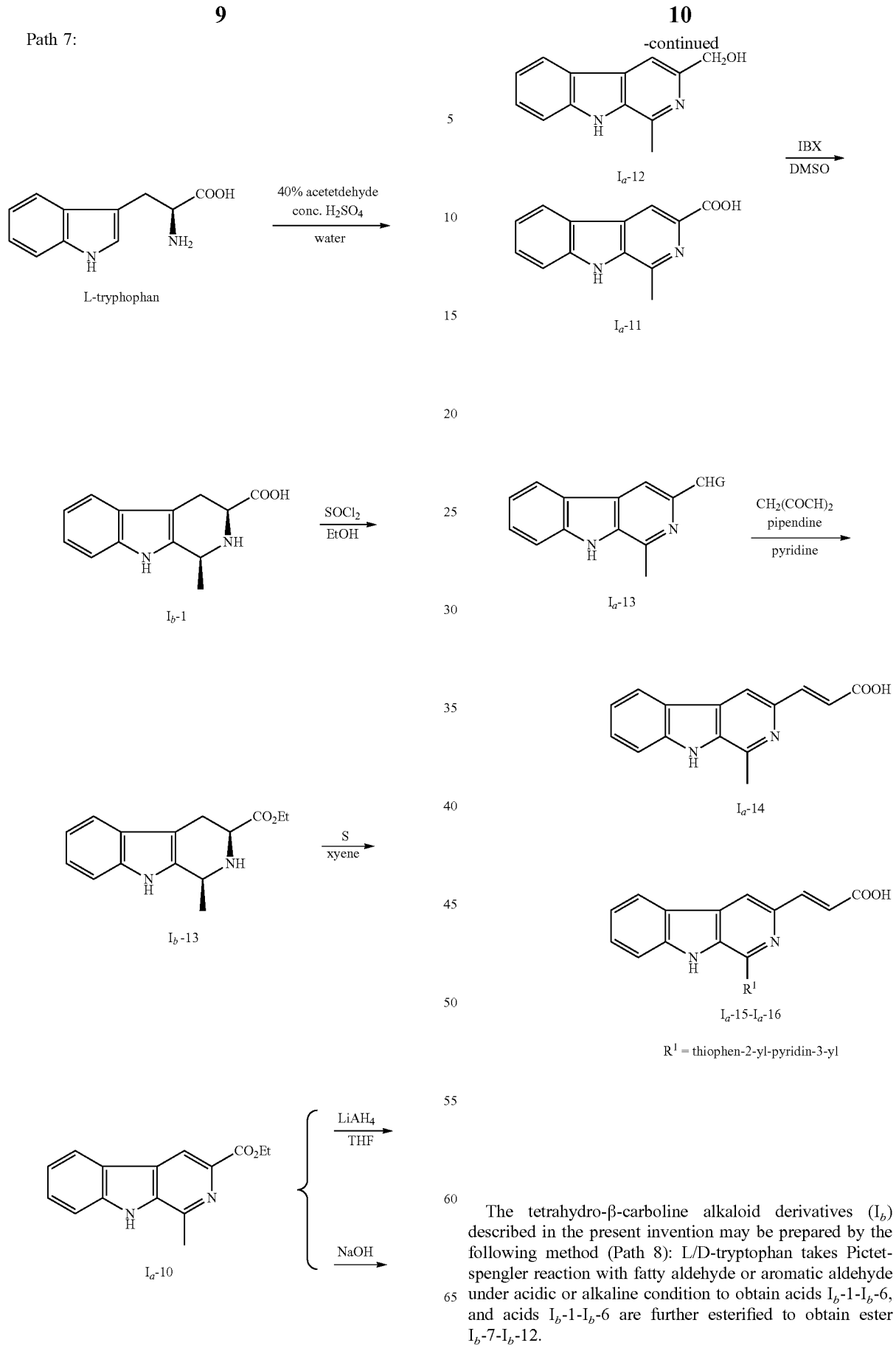

The tetrahydro-β-carboline alkaloid derivatives ($I_b$) described in the present invention may be prepared by the following method (Path 8): L/D-tryptophan takes Pictet-spengler reaction with fatty aldehyde or aromatic aldehyde under acidic or alkaline condition to obtain acids $I_b$-1-$I_b$-6, and acids $I_b$-1-$I_b$-6 are further esterified to obtain ester $I_b$-7-$I_b$-12.

Path 8:

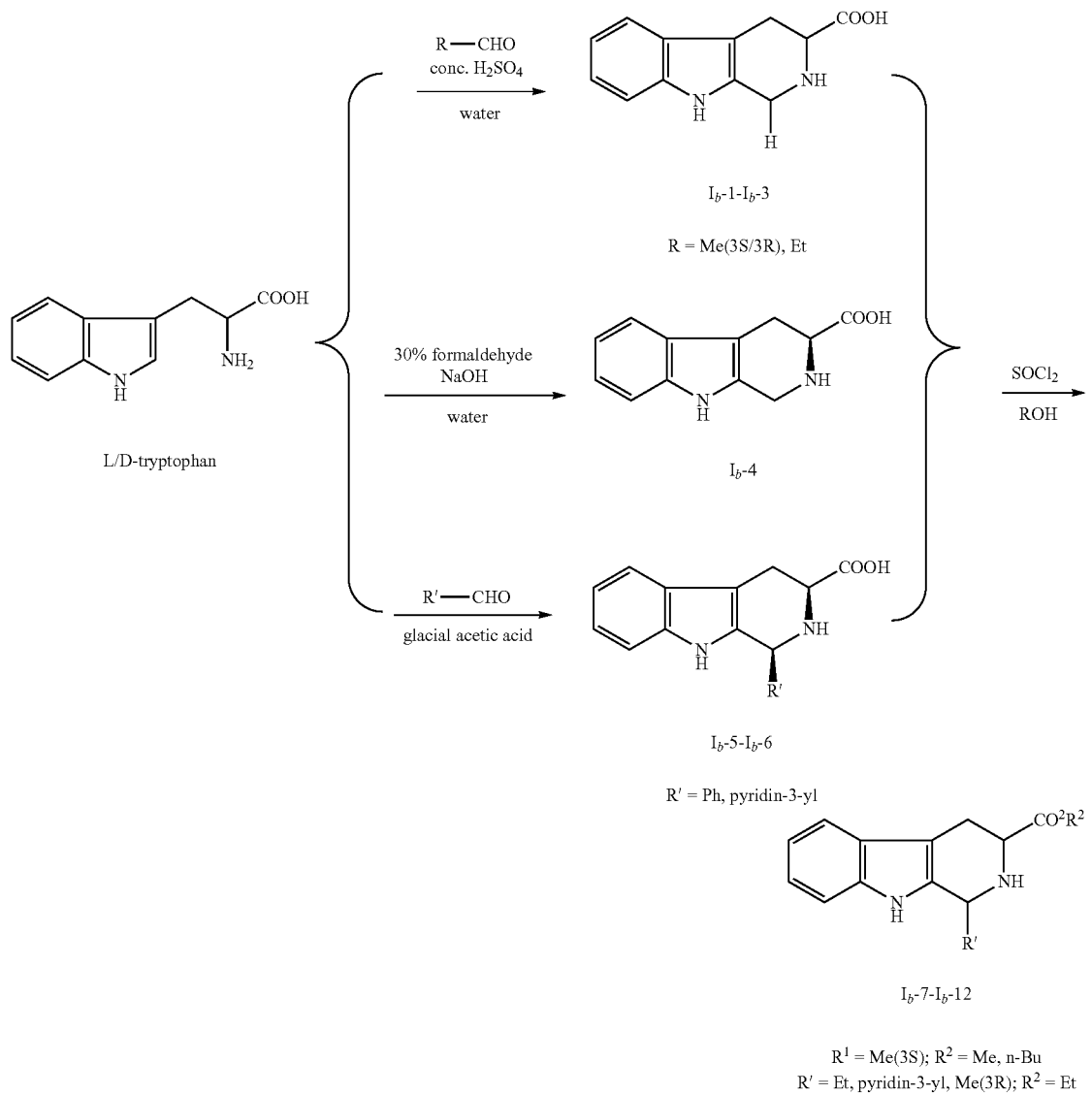

The dihydro-β-carboline alkaloid derivatives ($I_b$) described in the present invention may be prepared by the following method (Path 9): reacting L-tryptophan with ethanol to obtain ethyl ester 6, which is acylated and then reacting with phosphorus oxychloride to obtain dihydro-β-carboline alkaloid derivative $I_b$-14.

Path 9:

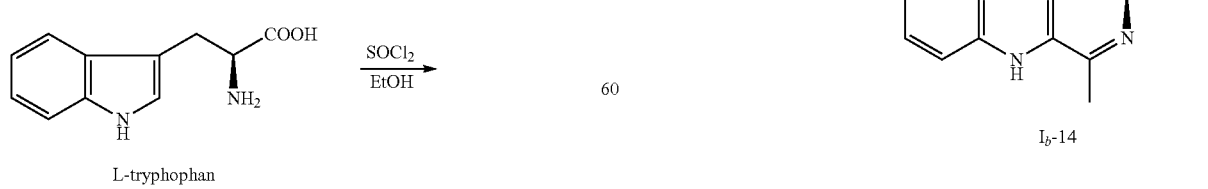

The tetrahydro-β-carboline alkaloid derivatives ($I_b$) described in the present invention may be prepared by the following method (Path 10): reacting methyl ester $I_b$-7 with hydrazine hydrate (80%) to obtain compound I$_b$-15, and reacting compound I$_b$-7 with amine to obtain amides I$_b$-16 and I$_b$-18.

Path 10:

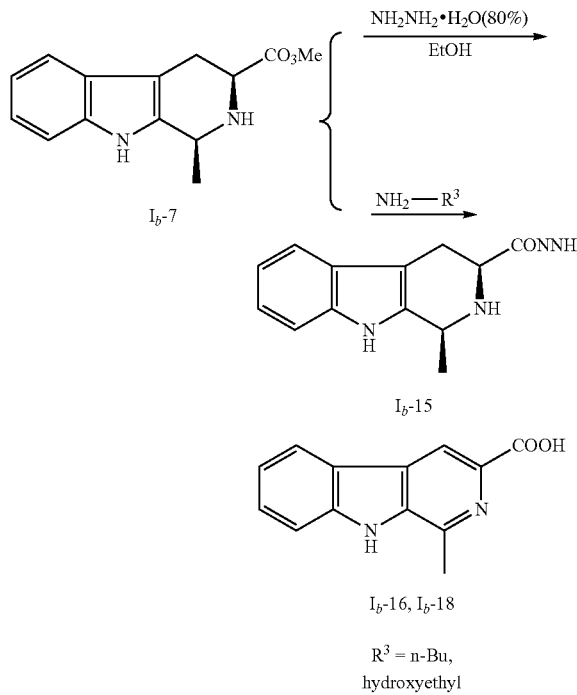

The tetrahydro-β-carboline alkaloid derivatives (I$_b$) described in the present invention may be prepared by the following method (Path 11): reacting acid I$_b$-1 with amine in presence of a condensation agent to obtain amides I$_b$-17, I$_b$-19-I$_b$-20.

Path 11:

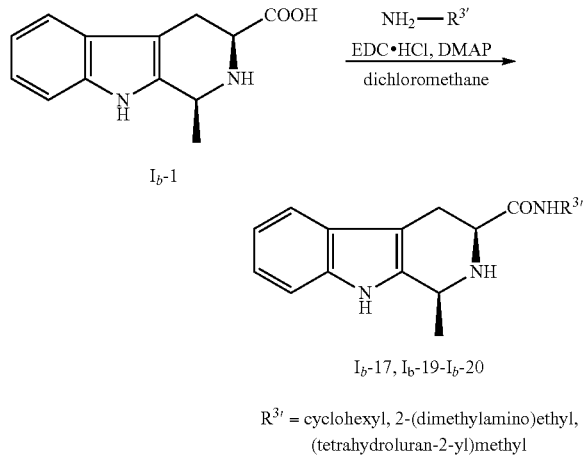

The tetrahydro-β-carboline alkaloid derivatives (I$_c$) described in the present invention may be prepared by the following method (Path 12): reacting hydrazide compound I$_b$-15 with fatty aldehyde or aromatic aldehyde to obtain corresponding acylhydrazone type compound I$_c$-1-I$_c$-29.

Path 12:

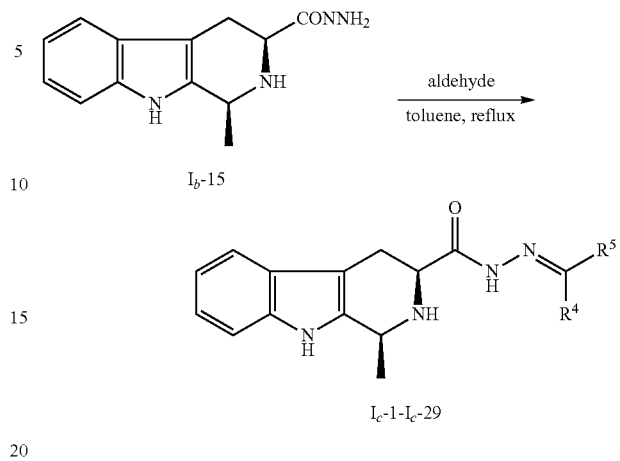

The tetrahydro-β-carboline alkaloid derivatives (I$_d$) described in the present invention may be prepared by the following method (Path 13): reacting hydrazide compound I$_b$-15 with acyl chloride to obtain corresponding bishydrazide type compound I$_d$-1-I$_d$-7.

Path 13:

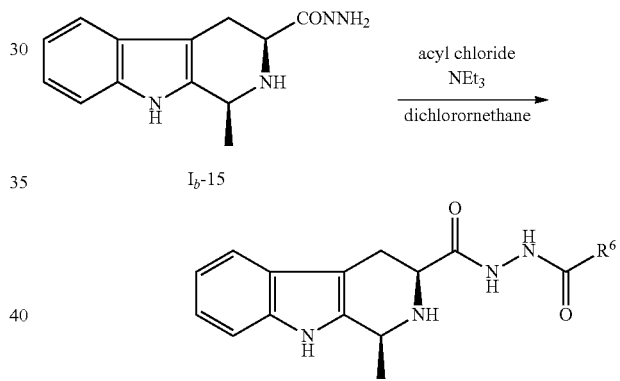

In the above general formulas,

R represents hydrogen, 1~4 halogen atoms, 1~4 nitro groups, 1~4 cyano groups, 1~4 C1-C6 alkoxy groups, 1~4 hydroxy groups, 1~4 ester groups, 1~2OCH$_2$O, 1-2OCH$_2$CH$_2$O, 1~4 C0-C10 amino groups, 1~4 C1-C6 alkyl carbonyl groups, 1~4 C1-C10 alkoxy carbonyl groups, 1~4 C1-C10 alkyl amino carbonyl groups, 1~4 C1-C6 alkoxy carbonyloxy groups, 1~4 C1-C6 alkyl amino carbonyloxy groups, 1~4 C1-C10 α-amino alkyl carbonyloxy groups;

R$^1$ respectively represents hydrogen, hydroxy, halogen atom, cyano group, ester group, amido group, C1-C10 hydrocarbyl, C1-C6 alkoxy, C1-C4 alkyl carbonyloxy, C1-C4 alkoxy carbonyloxy, C1-C10 nitrogen-containing heterocyclic ring, C1-C10 oxygen-containing heterocyclic ring, C1-C10 sulfur-containing heterocyclic ring, as well as stereomers of the foregoing compounds;

R$^2$ respectively represents hydrogen, hydroxy, C1-C6 alkoxy, amino, C1-C10 amino, halogen atom, cyano group, aldehyde group, C1-C6 alkyl carbonyl, C1-C10 alkoxy carbonyl, C1-C10 alkyl amino carbonyl, C1-C6 alkoxy carbonyloxy, C1-C6 alkyl amino carbonyloxy;

X respectively represents hydrogen, oxygen, sulfur, nitrogen, carbon;

$R^3$ respectively represents hydrogen, hydroxy, halogen atom, cyano group, ester group, amido group, C1-C10 hydrocarbyl, C1-C6 alkoxy, C1-C4 alkyl carbonyloxy, C1-C4 alkoxy carbonyloxy, C1-C10 nitrogen-containing heterocyclic ring, C1-C10 oxygen-containing heterocyclic ring, C1-C10 sulfur-containing heterocyclic ring;

$R^4$ and $R^5$ respectively represents hydrogen, C1-C10 hydrocarbyl, C1-C10 nitrogen-containing heterocyclic ring, C1-C10 oxygen-containing heterocyclic ring, C1-C10 sulfur-containing heterocyclic ring; $R^4$ and $R^5$ are C1-C10 aliphatic ring, C1-C10 unsaturated carbon ring, C1-C10 nitrogen-containing heterocyclic ring, C1-C10 oxygen-containing heterocyclic ring, C1-10 sulfur-containing heterocyclic ring;

$R^6$ respectively represents hydrogen, hydroxy, amino, C1-C10 hydrocarbyl, C1-C6 alkoxy, C1-C10 amino group, substituted phenyl ring, C1-C10 nitrogen-containing heterocyclic ring, C1-C10 oxygen-containing heterocyclic ring, C1-C10 sulfur-containing heterocyclic ring.

The β-carboline, dihydro-β-carboline and tetrahydro-β-carboline alkaloid derivatives (I) described in the present invention are preferably the following compounds:

(E)-3-(1-methyl-pyridino [3,4-b] indol-3)-acrylic acid ($I_a$-14);
(E)-3-(1-(thiophene-2)-pyridino [3,4-b] indol-3)-acrylic acid ($I_a$-15);
(E)-3-(1-(pyridine-3)-pyridino [3,4-b] indol-3)-acrylic acid ($I_a$-16);
(1S, 3S)—N-butyl-1-methyl-2,3,4,9-tetrahydro-pyridino [3,4-b] indol-3-formamide ($I_b$-16);
(1S, 3S)—N-cyclohexyl-1-methyl-2,3,4,9-tetrahydro-pyridino [3,4-b] indol-3-formamide ($I_b$-17);
(1S, 3S)—N-(2-ethoxyl)-1-methyl-2,3,4,9-tetrahydro-pyridino [3,4-b] indol-3-formamide ($I_b$-18);
(1S, 3S)—N-(dimethyl amino methyl)-1-methyl-2,3,4,9-tetrahydro-pyridino [3,4-b] indol-3-formamide ($I_b$-19);
(1S, 3S)—N-((tetrahydrofuran-2)-methyl)-1-methyl-2,3,4,9-tetrahydro-pyridino [3,4-b] indol-3-formamide ($I_b$-20);
(1S, 3S)—N'-benzylidene-1-methyl-2,3,4,9-tetrahydropyridino [3,4-b] indol-3-formylhydrazine
(1S, 3S)—N'-(4-tert-butyl benzylidene)-1-methyl-2,3,4,9-tetrahydropyridino [3,4-b] indol-3-formylhydrazine ($I_c$-2);
(1S, 3S)—N'-(4-dimethyl amino benzylidene)-1-methyl-2,3,4,9-tetrahydropyridino [3,4-b] indol-3-formylhydrazine ($I_c$-3);
(1S, 3S)—N'-(4-nitrobenzylidene)-1-methyl-2,3,4,9-tetrahydropyridino [3,4-b] indol-3-formylhydrazine ($I_c$-4);
(1S, 3S)—N'-(4-chlorobenzylidene)-1-methyl-2,3,4,9-tetrahydropyridino [3,4-b] indol-3-formylhydrazine ($I_c$-5);
(1S, 3S)—N'-(2, 4-dichlorobenzylidene)-1-methyl-2,3,4,9-tetrahydropyridino [3,4-b] indol-3-formylhydrazine ($I_c$-6);
(1S, 3S)—N'-(4-dichlorobenzylidene)-1-methyl-2,3,4,9-tetrahydropyridino [3,4-b] indol-3-formylhydrazine ($I_c$-7);
(1S, 3S)—N'-(4-methoxybenzylidene)-1-methyl-2,3,4,9-tetrahydropyridino [3,4-b] indol-3-formylhydrazine ($I_c$-8);
(1S, 3S)—N'-methoxybenzylidene)-1-methyl-2,3,4,9-tetrahydropyridino [3,4-b] indol-3-formylhydrazine ($I_c$-9);
(1S, 3S)—N'-(2-methoxybenzylidene)-1-methyl-2,3,4,9-tetrahydropyridino [3,4-b] indol-3-formylhydrazine ($I_c$-10);
(1S, 3S)—N'-(3,4-dimethoxybenzylidene)-1-methyl-2,3,4,9-tetrahydropyridino [3,4-b] indol-3-formylhydrazine ($I_c$-11);
(1S, 3S)—N'-((benzo [d] [1, 3] dioxymethylene-5)-methylene)-1-methyl-2,3,4,9-tetrahydropyridino [3,4-b] indol-3-formylhydrazine ($I_c$-12);
(1S, 3S)—N-((2, 3-dihydrobenzo [b] [1, 4] dioxin-6-methylene)-1-methyl-2,3,4,9-tetrahydropyridino [3,4-b] indol-3-formylhydrazine ($I_c$-13);
(1S, 3S)—N'-(6-hydroxynaphthalene-2-methylene)-1-methyl-2,3,4,9-tetrahydropyridino [3,4-b] indol-3-formylhydrazine ($I_c$-14);
(1S, 3S)—N'-(pyridine-4-methylene)-1-methyl-2,3,4,9-tetrahydropyridino [3,4-b] indol-3-formylhydrazine ($I_c$-15);
(1S, 3S)—N'-(pyridine-3-methylene)-1-methyl-2,3,4,9-tetrahydropyridino [3,4-b] indol-3-formylhydrazine ($I_c$-16);
(1S, 3S)—N'-(pyridine-2-methylene)-1-methyl-2,3,4,9-tetrahydropyridino [3,4-b] indol-3-formylhydrazine ($I_c$-17);
(1S, 3S)—N'-(furan-2-methylene)-1-methyl-2,3,4,9-tetrahydropyridino [3,4-b] indol-3-formylhydrazine ($I_c$-18);
(1S, 3S)—N'-(pyrrole-2-methylene)-1-methyl-2,3,4,9-tetrahydropyridino [3,4-b] indol-3-formylhydrazine ($I_c$-19);
(1S, 3S)—N'-(thiophene-2-methylene)-1-methyl-2,3,4,9-tetrahydropyridino [3,4-b] indol-3-formylhydrazine ($I_c$-20);
(1S, 3S)—N'-(imidazole-2-methylene)-1-methyl-2,3,4,9-tetrahydropyridino [3,4-b] indol-3-formylhydrazine ($I_c$-21);
(1S, 3S)—N'-((E)-but-2-enylidene)-1-methyl-2,3,4,9-tetrahydropyridino [3,4-b] indol-3-formylhydrazine ($I_c$-22);
(1S, 3S)—N'-butylidene-1-methyl-2,3,4,9-tetrahydropyridino [3,4-b] indol-3-formylhydrazine ($I_c$-23);
(1S, 3S)—N'-octadien-1-methyl-2,3,4,9-tetrahydropyridino [3,4-b] indol-3-formylhydrazine ($I_c$-24);
(1S, 3S)—N'-cyclohexylmethylene)-1-methyl-2,3,4,9-tetrahydropyridino [3,4-b] indol-3-formylhydrazine ($I_c$-25);
(1S, 3S)—N-(2,2-dimethylpropylidene)-1-methyl-2,3,4,9-tetrahydropyridino [3,4-b] indol-3-formylhydrazine ($I_c$-26);
(1S, 3S)—N'-(1-phenylethylidene)-1-methyl-2,3,4,9-tetrahydropyridino [3,4-b] indol-3-formylhydrazine ($I_c$-27);
(1S, 3S)—N'-(3,3-dimethyl-2-butylidene)-1-methyl-2,3,4,9-tetrahydropyridino [3,4-b] indol-3-formylhydrazine ($I_c$-28);
(1S, 3S)—N'-cyclohexylidene-1-methyl-2,3,4,9-tetrahydropyridino [3,4-b] indol-3-formylhydrazine ($I_c$-29);
N'—((1S, 3S)-1-methyl-2,3,4,9-tetrahydropyridino [3,4-b] indol-3-tricarboxylate)benzo [d] [1,2,3] thiadiazole-7-formylhydrazine ($I_d$-1);
4-methyl-N'-((1S, 3S)methyl-2,3,4,9-tetrahydropyridino [3,4-b] indol-3-triformyl)-1,2,3-thiadiazole-5-formylhydrazine ($I_d$-2);
(1S, 3S)—N'-isonicotinoyl-1-methyl-2,3,4,9-tetrahydropyridino [3,4-b] indol-3-formylhydrazine ($I_d$-3);
(1S, 3S)—N'-benzoyl-1-methyl-2,3,4,9-tetrahydropyridino [3,4-b] indol-3-formylhydrazine ($I_d$-4);
(1S, 3S)—N'—N-hexanoyl-1-methyl-2,3,4,9-tetrahydropyridino [3,4-b] indol-3-formylhydrazine ($I_d$-5);
(1S, 3S)—N'-tert-valeryl-1-methyl-2,3,4,9-tetrahydropyridino [3,4-b] indol-3-formylhydrazine ($I_d$-6);
(1S, 3S)—N'-(cyclopentylformyl)-1-methyl-2,3,4,9-tetrahydropyridino [3,4-b] indol-3-formylhydrazine ($I_d$-7).

The compounds shown in general formula (I) of the present invention have excellent activity against plant viruses, can satisfactorily inhibit tobacco mosaic virus, chilli virus, rice virus, tomato virus, sweet potato virus, potato virus and cucurbits virus and maize dwarf mosaic virus, may effectively prevent and control virus diseases of tobacco, chilli, paddy, tomato, cucurbitaceous vegetable, grain, vegetable, bean and other crops, and is particularly applicable to the prevention and treating of tobacco mosaic. β-carboline, dihydro-β-carboline and tetrahydro-β-carboline alkaloid derivatives shown in general formula (I) have very high in vitro activity against TMV and also show very good in vivo activity against tobacco mosaic virus (TMV), and the in vivo activity of some of β-carboline, dihydro-β-carboline and tetrahydro-β-carboline alkaloid derivatives against tobacco mosaic virus is obviously better than that of commercial variety virazole. Particularly, the activity of compounds Harmalan, Tetrahydroharmane, Harmane, Tetrahydroharmine, $I_a$-1, $I_b$-13, $I_b$-15, $I_c$-1-$I_c$-9, $I_c$-12, $I_c$-19, $I_c$-20, $I_c$-24-$I_c$-26, $I_c$-28, $I_d$-1, $I_d$-6 and $I_d$-7 against tobacco mosaic virus at concentration of 100 μg/mL is equivalent to the activity of commercial variety ningnanmycin at concentration of 100 μg/mL. As far as we know, it is also the first time to report β-carboline, dihydro-β-carboline and tetrahydro-β-carboline alkaloid and their derivatives have activity against plant viruses.

The compounds shown in general formula (I) of the present invention can be used as inhibitors of plant viruses directly, or used by adding an agriculturally acceptable vector, or used by forming interactive compositions with other agents against plant viruses, such as: diazosulfide (BTH), tiadinil (TDL), 4-methyl-1,2,3-thiadiazole-5-formic acid (TDLA), DL-p-aminobutyric acid (BABA), virazole, ningnanmycin, phenanthroindolizidine alkaloid Antofine, linked triazole compounds XY-13 and XY-30, virus A, salicylic acid, polyhydroxy dinaphthaldehyde and amino oligosaccharin. Some of these compositions show a synergistic effect and some show an additive effect.

The compounds shown in general formula (I) of the present invention have the activity of killing armyworms, cotton bollworms and corn borers as well as *culex pipiens*.

The compounds shown in general formula (I) of the present invention show bactericidal activity against the following 14 kinds of pathogenic bacteria: cucumber fusarium wilt, *Cercospora arachidicola*, *Macrophoma kawatsukai*, *Alternaria solani*, *Fusarium graminearumt*, potato late blight, *Sclerotinia scleotiorum*, *Botrytis cinerea*, *Rhizoctonia solani*, *Phytophthora capsici*, *Fusarium fujikuroi*, *Rhizoctonia cereali*, *Bipolaria maydis* and *Colletotrichum orbiculare*.

The compounds shown in general formula (I) of the present invention can be used as insecticides and bactericides directly, or used by adding an agriculturally acceptable vector, or used in combination with other insecticides, miticides and bactericides, such as: tebufenpyrad, chlorfenapyr, etoxazole and fenpyroximate etc. Some of these compositions show a synergistic effect and some show an additive effect.

DETAILED DESCRIPTION OF THE EMBODIMENTS

The following embodiments and bioassay results are intended to further illustrate but not to limit the present invention.

Embodiment 1: Synthesis of Dihydro-β-Carboline Alkaloid Harmalan

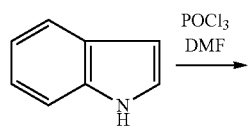

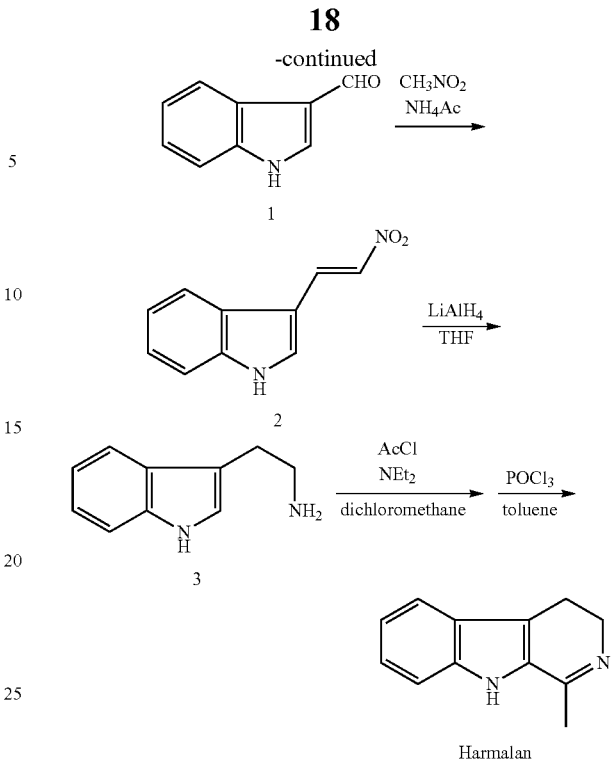

Synthesis of Indol-3-Formaldehyde

Add 140 mL of DMF to a 500 mL single-necked flask, add 27 mL of POCl$_3$ at 0° C., then add 50 mL of DMF solution containing 25 g (214 mmol) of indole and stir them overnight. Add 50 mL of water and 150 mL of 20% NaOH aqueous solution in turn and heat and reflux them for 6 h. Pour the reaction solution into water and conduct suction filtration to obtain 20.6 g of brown solid. The yield is 66% and the melting point is 190-192° C. (literature value: 190-192° C.);

$^1$H NMR (400 MHz, CDCl$_3$)

δ 10.08 (s, 1H, CHO), 8.80 (s, 1H, NH), 8.32-8.34 (m, 1H, Ar—H), 7.86 (d, $^3J_{HH}$=2.8 Hz, 1H, Ar—H), 7.44-7.62 (m, 1H, Ar—H), 7.31-7.36 (m, 2H, Ar—H).

Synthesis of (E)-3-(Nitrovinyl) Indole

Add 20 g (138 mmol) of indol-3-formaldehyde, 5.3 g (69 mmol) of ammonium acetate and 200 mL of nitromethane to a 500 mL single-necked flask, and heat and reflux them for 8 h. Add 200 mL of water and 150 mL of ethyl acetate and separate the liquid. Wash the organic phase with water, dry it and evaporate the solvent under a reduced pressure. Use dichloromethane for column chromatography under normal pressure to obtain 19.1 g of yellow solid. The yield is 74% and the melting point is 170-171° C.;

$^1$H NMR (400 MHz, CDCl$_3$) δ 8.74 (s, 1H, NH), 8.30 (d, $^3J_{HH}$=13.6 Hz, 1H, CH), 7.79-7.83 (m, 2H, CH and Ar—H), 7.69 (d, $^3J_{HH}$=2.8 Hz, 1H, Ar—H), 7.48-7.50 (m, 1H, Ar—H), 7.33-7.38 (m, 2H, Ar—H).

Synthesis of Tryptamine

Add 500 mL of tetrahydrofuran to a 1000 mL single-necked flask, and add 11.4 g (300 mmol) of lithium aluminum hydride and 9.4 g (50 mmol) of (E)-3-(nitrovinyl)

indole. Heat and reflux them for 7 h. Use water to quench lithium aluminum hydride not fully reacted. Conduct suction filtration, remove the solvent in the filtrate and add ethyl acetate and water to separate liquid. Wash the organic phase with a saturated saline solution, dry it with anhydrous sodium sulfate, remove solvent to obtain a red viscous substance, and dry it naturally to obtain 8.9 g of brown solid. The yield is 89% and the melting point is 115-117° C.;

$^1$H NMR (400 MHz, CDCl$_3$) δ 8.26 (s, 1H, NH), 7.62 (d, $^3J_{HH}$=7.6 Hz, 1H, Ar—H), 7.36 (d, $^3J_{HH}$=8.0 Hz, 1H, Ar—H), 7.20 (t, $^3J_{HH}$=7.6 Hz, 1H, Ar—H), 7.12 (t, $^3J_{HH}$=7.3 Hz, 1H, Ar—H), 7.02 (s, 1H, Ar—H), 3.04 (t, $^3J_{HH}$=6.4 Hz, 2H, CH$_2$), 2.91 (t, $^3J_{HH}$=6.8 Hz, 2H, CH$_2$), 1.47 (s, 2H, NH$_2$).

Synthesis of Harmalan

Add 0.5 g (3.13 mmol) of tryptamine, 40 mL of dichloromethane and 2 mL of triethylamine to a 100 mL single-necked flask. Add 5 mL of dichloromethane solution containing 0.27 g (3.44 mmol) of acetylchloride and react at room temperature for 5 h. Wash the reaction solution with a saturated sodium bicarbonate aqueous solution, dry it with anhydrous sodium sulfate and remove the solvent. Add 20 mL of toluene, 20 mL of chloroform and 3 mL of phosphorus oxychloride without the need of purification. Heat and reflux them for 7 h. Add sodium carbonate to regulate the reaction solution to be alkaline. Extract the reaction solution with dichloromethane, and wash the organic phase with a saturated saline solution, dry it with anhydrous sodium sulfate and remove the solvent. Use dichloromethane/methanol (10:1) for column chromatography under normal pressure to obtain 0.35 g of brownish yellow solid. The yield is 60% and the melting point is 110-113° C.;

$^1$H NMR (400 MHz, CDCl$_3$) δ 9.47 (s, 1H, NH), 7.60 (d, $^3J_{HH}$=8.0 Hz, 1H, Ar—H), 7.48 (d, $^3J_{HH}$=8.4 Hz, 1H, Ar—H), 7.31 (t, $^3J_{HH}$=8.0 Hz, 1H, Ar—H), 7.16 (t, $^3J_{HH}$=8.0 Hz, 1H, Ar—H), 3.88 (t, $^3J_{HH}$=8.4 Hz, 2H, CH$_2$), 2.95 (t, $^3J_{HH}$=8.8 Hz, 2H, CH$_2$), 2.53 (s, 3H, CH$_3$), HRMS (ESI) calcd for C$_{32}$H$_{13}$N$_2$(M+H)$^+$ 185.1073. found 185.1077.

Embodiment 2: Synthesis of Tetrahydroharmane and Harmane

Synthesis of Tetrahydroharmane

Add 8.1 mL (43.75 mmol) of 40% acetaldehyde aqueous solution, 250 mL of water and 5 drops of concentrated sulfuric acid to a 500 mL single-necked flask. Stir them at room temperature for 0.5 h, add 3.50 g (21.88 mmol) of tryptamine and heat and reflux them for 7 h. Add NaOH to regulate pH value to around 10, extract the solution with dichloromethane, wash the organic phase with a saturated saline solution, dry it with anhydrous sodium sulfate, remove the solvent, and use dichloromethane/methanol (5:1) for column chromatography under normal pressure to obtain 2.53 g of brown solid. The yield is 62% and the melting point is 173-175° C.;

$^1$H NMR (400 MHz, d$_6$-DMSO) δ 10.68 (s, 1H, NH), 7.35 (d, $^3J_{HH}$=8.0 Hz, 1H, Ar—H), 7.27 (d, $^3J_{HH}$=8.0 Hz, 1H, Ar—H), 6.98-7.02 (m, 1H, Ar—H), 6.97-6.95 (m, 1H, Ar—H), 3.99-4.04 (m, 1H, CHNH), 3.33 (s, 1H, CHNH), 3.14-3.19 (m, 1H, CH$_2$NH), 2.81-2.87 (m, 1H, CH$_2$NH), 2.51-2.62 (m, 2H, CH$_2$CH$_2$), 1.36 (d, $^3J_{HH}$=6.8 Hz, 3H, CH$_2$CH), HRMS (ESI) calcd for C$_{12}$H$_{12}$N$_2$(M+H)$^+$ 187.1230. found 187.1231.

Synthesis of Harmane

Add 0.85 g (4.57 mmol) of tetrahydrocarboline, 0.53 g (4.57 mmol) of maleic acid, 120 mL of water and 0.85 g of Pd/C to a 250 mL single-necked flask. Heat and reflux them for 8 h, conduct suction filtration, wash with water and regulate pH value of the filtrate with NaOH to 9-10 to obtain a large amount of white solid. Conduct suction filtration to obtain 0.5 g of white solid. The yield is 60% and the melting point is 244-245° C.;

$^1$H NMR (400 Mhz, CDCl$_3$) δ 8.41 (s, 1H, NH), 8.37 (d, $^3J_{HH}$=5.2 Hz, 1H, Ar—H), 8.12 (d, $^3J_{HH}$=8.0 Hz, 1H, Ar—H), 7.83 (d, $^3J_{HH}$=5.2 Hz, 1H, Ar—H), 7.52-7.57 (m, 2H, Ar—H), 7.26-7.32 (m, 1H, Ar—H), 2.84 (s, 3H, CH$_3$), HRMS (ESI) calcd for C$_{12}$H$_{11}$N$_2$(M+H)$^+$ 183.0917. found 183.0915.

Embodiment 3: Synthesis of Tetrahydroharmine

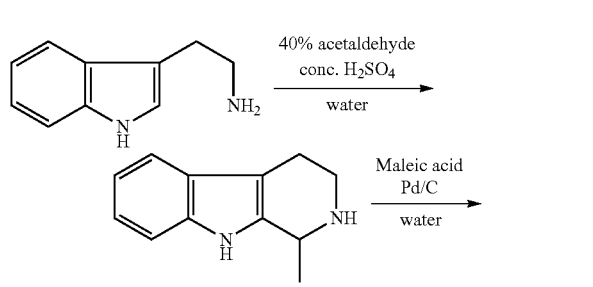

Tetrahydroharmane

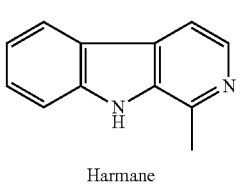

Harmane

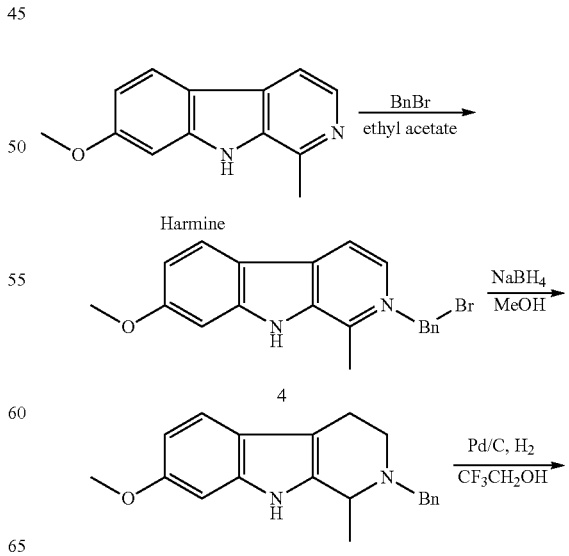

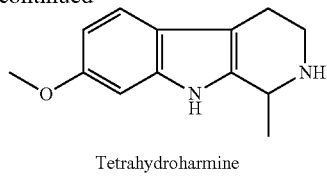

Tetrahydroharmine

Synthesis of Quaternary Ammonium Salt

Add 0.5 g (2.36 mmol) of harmine, 120 mL of ethyl acetate and 0.48 g (2.83 mmol) of benzyl bromide to a 250 mL single-necked flask. Heat and reflux them for 12 h. Conduct suction filtration to obtain 0.67 g of light yellow solid. The yield is 74% and the melting point is above 300° C.;

$^1$H NMR (400 Mhz, $d_6$-DMSO) δ 12.78 (s, 1H, NH), 8.74 (d, $^3J_{HH}$=6.4 Hz, 1H, Ar—H), 8.58 (d, $^3J_{HH}$=6.8 Hz, 1H, Ar—H), 8.37 (d, $^3J_{HH}$=8.8 Hz, 1H, Ar—H), 7.35-7.44 (m, 3H, Ar—H), 7.23 (d, $^3J_{HH}$=7.2 Hz, 2H, Ar—H), 7.12 (d, $^3J_{HH}$=1.0 Hz, 1H, Ar—H), 7.08 (dd, $^3J_{HH}$=8.8 Hz, $^3J_{HH}$=1.0 Hz, 1H, Ar—H), 5.98 (s, 2H, CH$_2$), 3.95 (s, 3H, OCH$_3$), 2.98 (s, 3H, CH$_3$).

Synthesis of N-Benzyl Tetrahydroharmine

Add 0.67 g (1.75 mmol) of quaternary ammonium salt and 150 mL of methanol to a 250 mL single-necked flask, and add 30 mL of methanol solution containing 0.53 g (14.0 mmol) of sodium borohydride. Heat and reflux them for 15 h. Remove the solvent and add dichloromethane and water to separate liquid. Wash the organic phase with a saturated saline solution, dry it with anhydrous sodium sulfate, remove the solvent, and use dichloromethane/methanol (20:1) for column chromatography under normal pressure to obtain 0.47 g of brown solid. The yield is 88% and the melting point is 147-149° C.;

$^1$H NMR (400 MHz, CDCl$_3$) δ 7.68 (s, 1H, NH), 7.50-7.52 (m, 2H, Ar—H), 7.43-7.47 (m, 3H, Ar—H), 7.36-7.40 (m, 1H, Ar—H), 6.90 (dd, $^3J_{HH}$=8.8 Hz, $^3J_{HH}$=2.4 Hz, 1H, Ar—H), 6.83 (d, $^3J_{HH}$=2.4 Hz, 1H, Ar—H), 3.97 (d, $^3J_{HH}$=13.6 Hz, 1H, CH$_2$C$_6$H$_5$), 3.81 (q, $^3J_{HH}$=6.8 Hz, 1H, CHCH$_3$), 3.77 (d, $^2J_{HH}$=13.6 Hz, 1H, CH$_2$C$_6$H$_5$), 3.22-3.29 (m, 1H, CH$_2$CH$_2$), 2.85-2.95 (m, 2H, CH$_2$CH$_2$), 2.68-2.74 (m, 1H, CH$_2$CH$_2$), 1.61 (d, $^3J_{HH}$=6.8 Hz, 1H, CHCH$_3$).

Synthesis of Tetrahydroharmine

Add 0.70 g (2.29 mmol) of N-benzyl-protected tetrahydroharmine, 120 mL of trifluoroethanol and 0.70 g of Pd/C to a 250 mL single-necked flask, input hydrogen and stir them overnight. Remove the solvent, and use dichloromethane/methanol (10:1) for column chromatography under normal pressure to obtain 0.37 g of light yellow viscous substance. The yield is 80% and the melting point is 195-197° C.;

$^1$H NMR (400 MHz, CDCl$_3$) δ 7.64 (s, 1H, NH), 7.35 (d, $^3J_{HH}$=8.8 Hz, 1H, Ar—H), 6.85 (d, $^3J_{HH}$=2.0 Hz, 1H, Ar—H), 6.77 (dd, $^3J_{HH}$=8.4 Hz, $^3J_{HH}$=2.4 Hz, 1H, Ar—H), 4.14-4.19 (m, 1H, CHCH$_3$), 3.84 (s, 3H, OCH$_3$), 3.33-3.39 (m, 1H, CH$_2$CH$_2$), 3.01-3.07 (m, 1H, CH$_2$CH$_2$), 2.66-2.78 (m, 2H, CH$_2$CH$_2$), 1.65 (s, 1H, NH), 1.44 (d, $^3J_{HH}$=6.8 Hz, 3H, CH$_3$), HRMS (ESI) calcd for C$_{33}$H$_{37}$N$_2$O (M+H)$^+$ 217.1335. found 217.1337.

Embodiment 4: Synthesis of Harmol

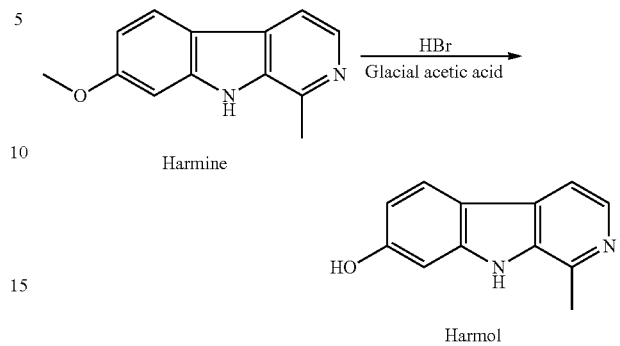

Harmine

Harmol

Add 0.5 g (2.36 mmol) of harmine, 18 mL of glacial acetic acid and 18 mL of 40% hydrobromic acid aqueous solution to a 100 mL single-necked flask, and heat and reflux them for 10 h. Use saturated sodium bicarbonate to regulate pH value to around 8 and generate precipitate. Conduct suction filtration to obtain 0.46 g of yellow green solid. The yield is 98% and the melting point is above 300° C.;

$^1$H NMR (400 MHz, $d_6$-DMSO) δ 11.24 (s, 1H, NH), 9.72 (s, 1H, OH), 8.11 (d, $^3J_{HH}$=5.2 Hz, 1H, Ar—H), 7.94 (d, $^3J_{HH}$=8.0 Hz, 1H, Ar—H), 7.75 (d, $^3J_{HH}$=5.2 Hz, 1H, Ar—H), 6.90 (d, $^4J_{HH}$=1.2 Hz, 1H, Ar—H), 6.69 (dd, $^3J_{HH}$=8.4 Hz, $^4J_{HH}$=1.6 Hz, 1H, Ar—H), 2.69 (s, 3H, CH$_3$), HRMS (ESI) calcd for C$_{12}$H$_{11}$N$_2$O (M+H)$^+$ 199.0866. found 199.0867.

Embodiment 5: Synthesis of Bromo and Nitro-Substituted Harmane

Synthesis of Bromo-Harmane (I$_a$-1 and I$_a$-2)

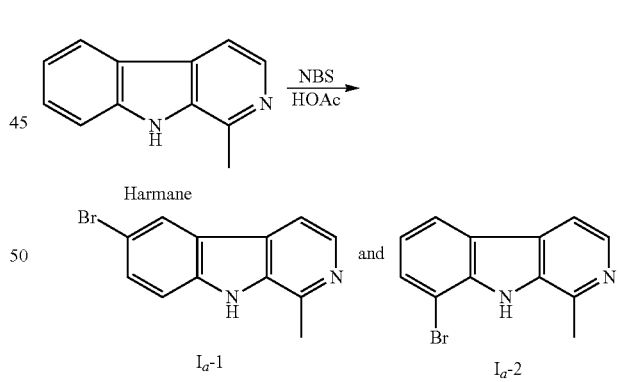

Harmane

I$_a$-1        I$_a$-2

Add of 0.2 g (1.10 mmol) of harman and 10 mL of glacial acetic acid to a 25 mL single-necked flask, add 0.2 g (1.10 mmol) of NB S, and react at room temperature for 6 h. Remove the solvent, wash with saturated sodium bicarbonate, extract with dichloromethane, dry the organic phase with anhydrous sodium sulfate, remove the solvent and use dichloromethane/methanol (40:1→20:1) in turn for column chromatography under normal pressure to obtain two kinds of white solid: solid I$_a$-1 0.05 g, yield 17%; $^1$H NMR (400 MHz, CDCl$_3$) δ 8.36-8.49 (m, 2H, NH and Ar—H), 8.04 (d, $^3J_{HH}$=6.4 Hz, 1H, Ar—H), 7.77-7.84 (m, 1H, Ar—H), 7.70

(d, $^3J_{HH}$=6.4 Hz, 1H, Ar—H), 7.18 (t, $^3J_{HH}$=6.4 Hz, 1H, Ar—H), 2.88 (s, 3H, CH$_3$). Solid I$_a$-2 0.24 g, yield 83%, melting point 256-257° C.;

$^1$H NMR (400 MHz, CDCl$_3$) δ 8.44 (s, 1H, NH), 8.39 (d, $^3J_{HH}$=5.6 Hz, 1H, Ar—H), 8.24 (d, $^4J_{HH}$=2.0 Hz, 1H, Ar—H), 7.78 (d, $^3J_{HH}$=5.6 Hz, 1H, Ar—H), 7.63 (dd, $^3J_{HH}$=8.4 Hz, $^4J_{HH}$=2.0 Hz, 1H, Ar—H), 7.42 (d, $^3J_{HH}$=8.8 Hz, 1H, Ar—H), 2.83 (s, 3H, CH$_3$), HRMS (ESI) calcd for C$_{12}$H$_{13}$BrN$_2$(M+H)$^+$ 261.0022. found 261.0026.

Synthesis of Nitro-Substituted Harmane (I$_c$-3 and I$_a$-4)

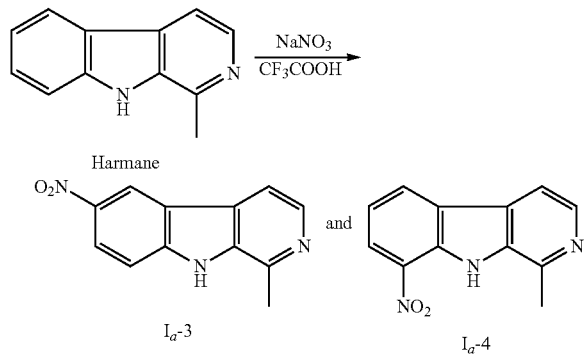

Add 0.4 g (2.20 mmol) of harman and 0.93 g (10.99 mmol) of sodium nitrate to a 50 mL single-necked flask, add 20 mL of trifluoroacetic acid, and stir them at room temperature for 6 h. Add a saturated sodium bicarbonate aqueous solution to the reaction solution to regulate pH value to 10-11 and generate yellow precipitate, and conduct suction filtration to obtain 0.06 g of yellow solid I$_a$-3. The yield is 12% and the melting point is 207-210° C.

$^1$H NMR (400 MHz, d$_6$-DMSO) δ 11.77 (s, 1H, NH), 8.77 (d, $^3J_{HH}$=7.6 Hz, Ar—H), 8.50 (d, $^3J_{HH}$=8.0 Hz, 1H, Ar—H), 8.38 (d, $^3J_{HH}$=5.2 Hz, 1H, Ar—H), 8.11 (d, $^3J_{HH}$=5.2 Hz, 1H, Ar—H), 7.48 (t, $^3J_{HH}$=7.6 Hz, 1H, Ar—H), 2.92 (s, 3H, CH$_3$), HRMS (ESI) calcd for C$_{12}$H$_{19}$N$_3$O$_3$(M+H)$^+$ 228.0768. found 228.0772, 0.36 g.

0.36 g of light yellow solid I$_a$-4. The yield is 12% and the melting point is above 300° C.

$^1$H NMR (400 MHz, d$_6$-DMSO) δ 12.36 (s, 1H, NH), 9.30 (d, $^4J_{HH}$=2.0 Hz, 1H, Ar—H), 8.41 (dd, $^3J_{HH}$=8.8 Hz, $^3J_{HH}$=3.0 Hz, 1H, Ar—H), 8.33 (d, $^3J_{HH}$=5.6 Hz, 1H, Ar—H), 8.20 (d, $^3J_{HH}$=5.2 Hz, 1H, Ar—H), 7.73 (d, $^3J_{HH}$=8.4 Hz, 1H, Ar—H), 2.79 (s, 3H, CH$_3$), HRMS (ESI) calcd for C$_{12}$H$_{10}$N$_3$O$_2$ (M+H)$^-$ 228.0768. found 228.0767.

Embodiment 6: Synthesis of isopropylamino formate (1-methylpyridino [3,4-b] indol-7)-ester (I$_a$-5)

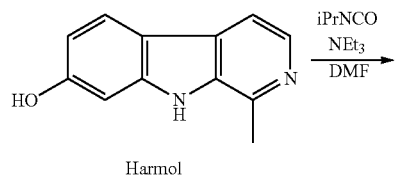

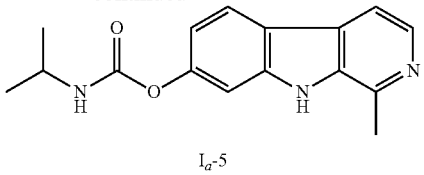

Add 0.5 g (2.53 mmol) of demethylated harmaline and 50 mL of DMF to a 100 mL single-necked flask, add 1.5 mL of isopropyl isocyanate and 0.08 g (0.758 mmol) of triethylamine, and stir them overnight. Add a saturated sodium chloride aqueous solution, extract with ethyl acetate, dry it with anhydrous sodium sulfate and remove the solvent. Use dichloromethane/methanol (20:1) for column chromatography under normal pressure to obtain 0.50 g of white solid. The yield is 70% and the melting point is above 300° C.;

$^1$H NMR (400 MHz, d$_6$-DMSO) δ 11.58 (s, 1H, NH), 8.20 (d, $^3J_{HH}$=5.2 Hz, 1H, Ar—H), 8.16 (d, $^3J_{HH}$=8.8 Hz, 1H, Ar—H), 7.90 (d, $^3J_{HH}$=5.2 Hz, 1H, Ar—H), 7.76 (d, $^3J_{HH}$=8.0 Hz, 1H, NHCO), 7.27 (d, $^4J_{HH}$=1.6 Hz, 1H, Ar—H), 6.95 (dd, $^3J_{HH}$=8.4 Hz, $^4J_{HH}$=2.0 Hz, 1H, Ar—H), 3.65-3.73 (m, 1H, CH), 2.75 (s, 3H, CH$_3$), 1.16 (d, $^3J_{HH}$=3.4 Hz, 6H, (CH$_3$)$_3$CH), HRMS (ESI) calcd for C$_{16}$H$_{14}$N$_2$O$_2$ (M+H)$^+$ 284.1394. found 284.1399.

Embodiment 7: Synthesis of dimethylcarbamate (1-methylpyridino [3,4-b] indol-7)-ester (I$_a$-6)

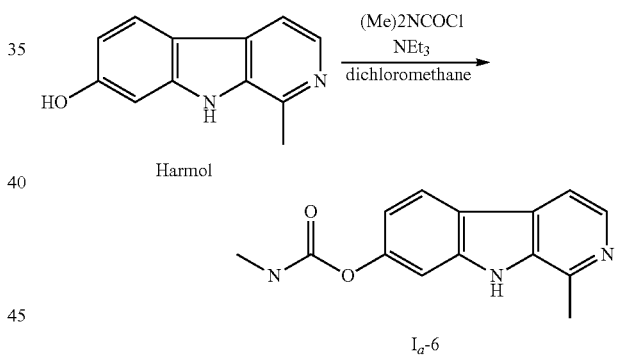

Add 0.4 g (2.02 mmol) of demethylated harmaline, 150 mL of tetrahydrofuran, 0.31 g (3.03 mmol) of triethylamine and a catalytic amount of DMAP to a 250 mL single-necked flask, stir them at room temperature for 0.5 h, add 0.33 g (3.03 mmol) of acyl chloride and stir them overnight. Remove the solvent, add dichloromethane and water to separate liquid, wash the organic phase with a saturated saline solution, dry it with anhydrous sodium sulfate, remove the solvent, and use dichloromethane/methanol (10:11) for column chromatography under normal pressure to obtain 0.48 g of white solid. The yield is 89% and the melting point is 225-227° C.;

$^1$H NMR (400 MHz, d$_6$-DMSO) δ 11.63 (s, 1H, NH), 8.20 (d, $^3J_{HH}$=5.2 Hz, 1H, Ar—H), 8.17 (d, $^3J_{HH}$=8.4 Hz, 1H, Ar—H), 7.91 (d, $^3J_{HH}$=5.2 Hz, 1H, Ar—H), 7.30 (d, $^3J_{HH}$=2.0 Hz, 1H, Ar—H), 6.97 (dd, $^3J_{HH}$=8.4 Hz, $^4J_{HH}$=2.0 Hz, 1H, Ar—H), 3.10 (s, 3H, CH$_3$), 2.94 (s, 3H, CH$_3$), 2.75 (s, 3H, CH$_3$), HRMS (ESI) calcd for C$_{15}$H$_{16}$N$_3$O$_2$ (M+H)$^+$ 270.1237. found 270.1240.

Compounds I$_a$-7-I$_a$-8 are completed through repeating the foregoing steps

Acetate (1-methylpyridino [3,4-b] indol-7)-ester (I$_a$-7)

White solid, yield 50%, melting point 237-240° C.;
$^1$H NMR (400 MHz, CDCl$_3$) δ 8.90 (s, 1H, NH), 8.23 (d, $^3J_{HH}$=2.4 Hz, 1H, Ar—H), 7.78 (d, $^3J_{HH}$=8.4 Hz, 1H, Ar—H), 7.70 (d, $^3J_{HH}$=2.0 Hz, 1H, Ar—H), 7.16 (s, 1H, Ar—H), 6.93 (d, $^3J_{HH}$=8.4 Hz, 1H, Ar—H), 2.76 (s, 3H, CH$_3$), 2.42 (s, 3H, CH$_3$CO), HRMS (ESI) calcd for C$_{14}$H$_{13}$N$_2$O$_2$ (M+H)$^+$ 241.0972. found 241.0970.

Tert-valerate (1-methylpyridino [3,4-b] indol-7)-ester (I$_a$-8)

White solid, yield 85%, melting point 221-222° C.;
$^1$H NMR (400 MHz, CDCl$_3$) δ 8.68 (s, 1H, NH), 8.30 (d, $^3J_{HH}$=5.2 Hz, 1H, Ar—H), 7.75 (d, $^3J_{HH}$=8.4 Hz, 1H, Ar—H), 7.54 (d, $^3J_{HH}$=4.8 Hz, 1H, Ar—H), 7.09 (s, 1H, Ar—H), 6.86 (d, $^3J_{HH}$=8.0 Hz, 1H, Ar—H), 2.73 (s, 3H, CH$_3$), 1.45 (s, 9H, C(CH$_3$)$_3$), HRMS (ESI) calcd for C$_{17}$H$_{13}$N$_2$O$_2$ (M+H)$^+$ 283.1441. found 283.1446.

Embodiment 8: Synthesis of (S)-3-methyl-2-carbobenzoxyaminobutyrate-(1-methylpyridino [3,4-b] indol-7-ester (I$_a$-9)

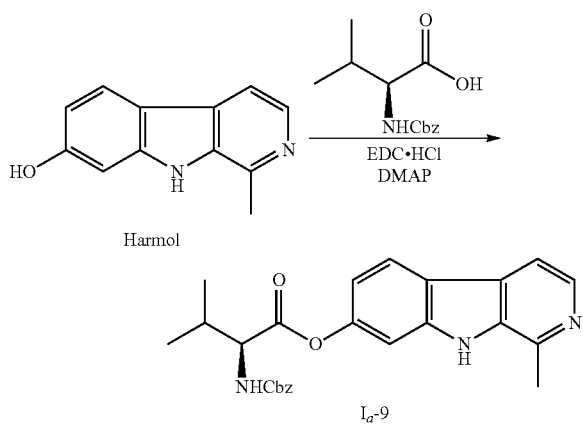

Add 0.80 g (3.03 mmol) of amino acid and 150 mL of dichloromethane to a 250 mL single-necked flask, and add 0.41 g (4.04 mmol) of triethylamine, 0.76 g (4.04 mmol) of EDCI (1-ethyl-(3-dimethylaminopropyl) carbonyldiimide hydrochloride) and 0.50 g (4.04 mmol) of DMAP (4-dimethylaminopyridine) and stir them overnight. Wash them with water, dry them with anhydrous sodium sulfate, remove the solvent, and use dichloromethane/methanol (20:1) for column chromatography under normal pressure to obtain 0.8 g of white solid. The yield is 92% and the melting point is 69-71° C.;
$^1$H NMR (400 MHz, CDCl$_3$) δ 8.54 (s, 1H, NH), 8.54 (d, $^3J_{HH}$=5.2 Hz, 1H, Ar—H), 7.92 (d, $^3J_{HH}$=8.4 Hz, 1H, Ar—H), 7.66 (d, $^3J_{HH}$=4.8 Hz, 1H, Ar—H), 7.35-7.38 (m, 5H, Ar—H), 7.19 (s, 1H, Ar—H), 6.94 (d, $^3J_{HH}$=8.4 Hz, 1H, Ar—H), 5.39 (d, $^3J_{HH}$=8.4 Hz, 1H, Ar—H), 5.17 (s, 2H, CH$_2$), 4.54-4.66 (m, 1H, CHNH), 2.77 (s, 3H, CH$_3$), 2.38-2.50 (m, 1H, CH(CH$_3$)$_2$), 1.14 (d, $^3J_{HH}$=6.8 Hz, 3H, CH(CH$_3$)$_3$), 1.09 (d, $^3J_{HH}$=6.8 Hz, 3H, CH(CH$_3$)$_2$), HRMS (ESI) calcd for C$_{23}$H$_{25}$N$_3$O$_4$(M+H)$^+$ 432.1918. found 432.1920.

Embodiment 9: (1S, 3S)-1-methyl-2,3,4,9-tetrahydropyridino [3,4-b] indol-3-formic acid (I$_b$-1)

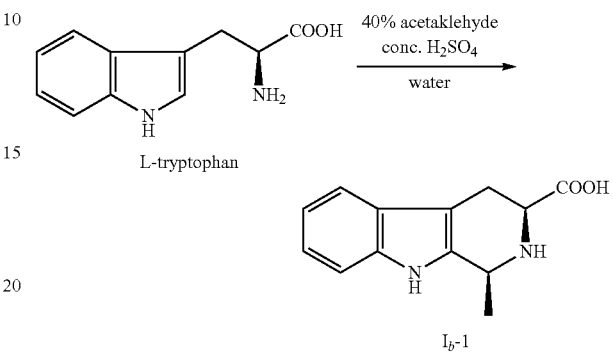

Add 20 g (98.0 mmol) of L-tryptophan, 500 mL of water, 2 mL of concentrated sulfuric acid and 20 mL of 40% acetaldehyde aqueous solution to a 1000 mL single-necked flask, stir them at room temperature overnight, use strong aqua to regulate pH value to 6-7, separate out white solid and conduct suction filtration to obtain 16.7 g of white solid. The yield is 74% and the melting point is 78-280° C.;
$^1$H NMR (400 MHz, d$_6$-DMSO) Γ 11.11 (s, 1H, COOH), 7.45 (d, $^3J_{HH}$=7.8 Hz, 1H, Ar—H), 7.34 (d, $^3J_{HH}$=8.0 Hz, 1H, Ar—H), 7.09 (t, $^3J_{HH}$=7.6 Hz, 1H, Ar—H), 7.00 (t, $^3J_{HH}$=7.2 Hz, 1H, Ar—H), 4.52 (q, $^3J_{HH}$=6.4 Hz, 1H, CH), 3.61 (dd, $^3J_{HH}$=11.6 Hz, $^3J_{HH}$=4.4 Hz, 1H, CH), 3.16 (dd, $^2J_{HH}$=16.0 Hz, $^3J_{HH}$=4.0 Hz, 1H, CH$_2$), 2.74-2.81 (m, 1H, CH$_2$), 1.62 (d, $^3J_{HH}$=6.4 Hz, 3H, CH$_3$); HRMS (ESI) calcd for C$_{23}$H$_{35}$N$_2$O$_2$ (M+H)$^+$ 231.1128. found 231.1132.

Compounds I$_b$-2 and I$_b$-3 are completed through repeating the foregoing steps

(1R,3R)-1-methyl-2,3,4,9-tetrahydropyridino [3,4-b] indol-3-formic acid (I$_b$-2)

White solid, yield 76%, melting point 285-287° C.;
$^1$H NMR (400 MHz, d$_6$-DMSO) δ 11.20 (s, 1H, COOH), 7.44 (d, $^3J_{HH}$=7.6 Hz, 1H, Ar—H), 7.35 (d, $^3J_{HH}$=8.0 Hz, 1H, Ar—H), 7.09 (t, $^3J_{HH}$=7.6 Hz, 1H, Ar—H), 7.00 (t, $^3J_{HH}$=7.6 Hz, 1H, Ar—H), 4.56 (q, $^4J_{HH}$=6.4 Hz, 1H, CHCH$_3$), 3.64 (dd, $^3J_{HH}$=12.0 Hz, $^3J_{HH}$=4.8 Hz, 1H, CH), 3.18 (dd, $^3J_{HH}$=16.0 Hz, $^3J_{HH}$=4.4 Hz, 1H, CH$_3$), 2.76-2.83 (m, 1H, CH$_2$), 1.64 (d, $^3J_{HH}$=6.4 Hz, 3H, CH$_3$); HRMS (ESI) calcd for C$_{13}$H$_{18}$N$_2$O$_2$ (M+H)$^+$ 231.1128. found 231.1132.

(1S, 3S)-1-ethyl-2,3,4,9-tetrahydropyridino [3,4-b] indol-3-formic acid (I$_b$-3)

2.67 g of white solid, yield 44%, melting point 277-280° C.;
$^1$H NMR (400 MHz, d$_6$-DMSO) δ 10.92 (s, 1H, COOH), 7.43 (d, $^3J_{HH}$=7.6 Hz, 1H, Ar—H), 7.35 (d, $^3J_{HH}$=8.0 Hz, 1H, Ar—H), 7.05-7.08 (m, 1H, Ar—H), 6.96-7.00 (m, 1H, Ar—H), 4.32-4.33 (m, 1H, CHNH), 3.54 (dd, $^3J_{HH}$=11.6 Hz, $^3J_{HH}$=4.4 Hz, 1H, CHCO), 3.10 (dd, $^3J_{HH}$=15.6 Hz, $^3J_{HH}$=4.0 Hz, 1H, CH$_2$), 2.70-2.78 (m, 1H, CH$_2$), 2.12-2.20

(m, 1H, CH$_2$CH$_3$), 1.83-1.90 (m, 1H, CH$_2$CH$_3$), 1.01 (t, $^3J_{HH}$=7.2 Hz, 3H, CH$_2$CH$_3$). HRMS (ESI) calcd for C$_{19}$H$_{17}$N$_2$O$_2$ (M+H)$^+$ 245.1285. found 245.1289.

Embodiment 10: Synthesis of 2,3,4,9-tetrahydropyridino [3,4-b] indol-3-formic acid (I$_b$-4)

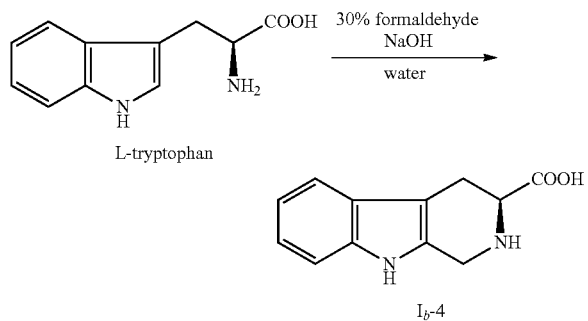

Add 10.00 g (49 mmol) of L-tryptophan, 1.96 g (49 mmol) of NaOH and 100 mL of water to a 250 mL single-necked flask, and add 5 mL of 30% formaldehyde aqueous solution. Heat and reflux them for 3 h. Use 3M diluted hydrochloric acid to regulate pH value to around 5 and generate precipitate, conduct suction filtration, wash the filter cakes with water and dry them to obtain 8.32 g of white solid. The yield is 88% and the melting point is 278-279° C.;

$^1$H NMR (400 MHz, d$_6$-DMSO) δ 10.97 (s, 1H, COOH), 7.45 (d, $^3J_{HH}$=7.8 Hz, 1H, Ar—H), 7.34 (d, $^3J_{HH}$=8.0 Hz, 1H Ar—H) 7.09 (t, $^3J_{HH}$=7.2 Hz, 1H, Ar—H), 7.00 (t, $^3J_{HH}$=7.2 Hz, 1H, Ar—H), 4.25 (d, $^2J_{HH}$=15.6 Hz, 1H, NHCH$_2$), 4.18 (d, $^3J_{HH}$=15.6 Hz, 1H, NHCH$_3$), 3.62 (dd, $^3J_{HH}$=10.4 Hz, $^3J_{HH}$=4.8 Hz, 1H, CH), 3.15 (dd, $^3J_{HH}$=16.4 Hz, $^3J_{HH}$=4.8 Hz, 1H, CH$_2$), 2.83 (dd, $^3J_{HH}$=15.6 Hz, $^3J_{HH}$=10.8 Hz, 1H, CH$_3$), HRMS (ESI) calcd for C$_{12}$H$_{13}$N$_2$O$_2$ (M+H)$^+$ 217.0972. found 217.0969.

Embodiment 11: Synthesis of (1S, 3S)-1-phenyl-2, 3,4,9-tetrahydropyridino [3,4-b] indol-3-formic acid (I$_b$-5)

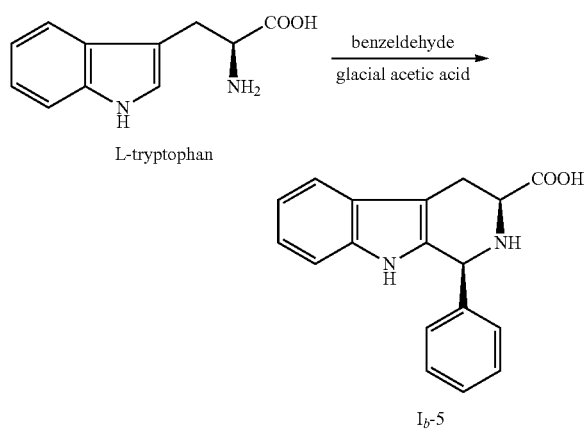

Add 2.5 g (12.3 mmol) of L-tryptophan, 50 mL of glacial acetic acid and 1.5 g (13.5 mmol) of benzeldehyde to a 100 mL single-necked flask, heat and reflux them for 12 h, remove the solvent, use ammonium hydroxide to regulate pH value to 5-6 and generate precipitate, and conduct suction filtration to obtain 3.1 g of white solid. The yield is 86% and the melting point is 197-207° C.;

$^1$H NMR (400 MHz, d$_6$-DMSO) δ 10.46 (s, 1H, COOH), 7.46 (d, $^3J_{HH}$=7.6 Hz, 1H, Ar—H), 7.39-7.41 (m, 5H, Ar—H), 7.23 (d, $^3J_{HH}$=8.0 Hz, 1H, Ar—H), 7.03 (t, $^3J_{HH}$=6.8 Hz, 1H, Ar—H), 6.98 (t, $^3J_{HH}$=7.6 Hz, 1H, Ar—H), 5.43 (s, 1H, CH), 4.95 (br, 1H, NH), 3.80 (dd, $^3J_{HH}$=11.2 Hz, $^3J_{HH}$=4.0 Hz, 1H, CH), 3.14 (dd, $^3J_{HH}$=18.4 Hz, $^3J_{HH}$=3.2 Hz, 1H, CH$_3$), 2.86-2.92 (m, 1H, CH$_2$), HRMS (ESI) calcd for C$_{18}$H$_{17}$H$_2$O$_2$ (M+H)$^+$ 293.1285. found 293.1286.

Compound I$_b$-6 is completed through repeating the foregoing steps.

(1S, 3S)-1-(pyridine-3)-2,3,4,9-tetrahydropyridino [3,4-b] indol-3-formic acid (I$_b$-6)

Yellow solid, yield 87% and the melting point is 250-253° C.;

$^1$H NMR (400 MHz, DMSO-d$_6$) δ 10.48 (s, 1H, COOH), 8.60 (d, $^3J_{HH}$=1.6 Hz, 1H, Ar—H), 8.56 (dd, $^3J_{HH}$=4.8 Hz, $^4J_{HH}$=1.6 Hz, 1H, Ar—H), 7.70 (dt, $^3J_{HH}$=8.0 Hz, $^4J_{HH}$=1.6 Hz, 1H, Ar—H), 7.47 (dd, $^3J_{HH}$=4.8 Hz, $^3J_{HH}$=8.0 Hz, 1H, Ar—H), 7.20 (d, $^3J_{HH}$=7.6 Hz, 1H, Ar—H), 7.00-7.04 (m, 1H, Ar—H), 6.96-6.99 (m, 1H, Ar—H), 5.37 (s, 1H, CHAr), 3.79 (dd, $^3J_{HH}$=11.2 Hz, $^3J_{HH}$=4.0 Hz, 1H, CHCOOH), 3.06-3.11 (m, 1H, CH$_2$), 2.81-2.88 (m, 1H, CH$_2$). HRMS (ESI) calcd for C$_{17}$H$_{16}$N$_3$O$_3$(M+H)$^+$ 294.1237. found 294.1237.

Embodiment 12: Synthesis of (1S, 3S)-1-methyl-2, 3,4,9-tetrahydropyridino [3,4-b] indol-3-ethyl formate (I$_b$-13)

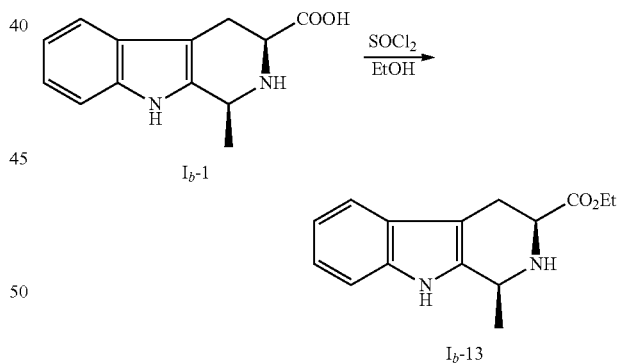

Add 16 g (69.0 mmol) of acid and 500 mL of anhydrous ethanol to a 1000 mL single-necked flask, add 30 mL of thionyl chloride, and heat and reflux them for 5 h. Use a saturated sodium bicarbonate aqueous solution to regulate pH value to 9 and generate precipitate, and conduct suction filtration to obtain 16.4 g of milky solid, The yield is 92% and the melting point is 136-137° C.;

$^1$H NMR (400 MHz, CDCl$_3$) δ 7.86 (s, 1H, NH), 7.49 (d, $^3J_{HH}$=8.0 Hz, 1H, Ar—H), 7.33 (d, $^3J_{HH}$=8.0 Hz, 1H, Ar—H), 7.17 (t, $^3J_{HH}$=7.2 Hz, 1H, Ar—H), 7.11 (t, $^3J_{HH}$=7.2 Hz, 1H, Ar—H), 4.26-4.31 (m, 3H, CH and OCH$_2$), 3.81 (dd, $^3J_{HH}$=11.2 Hz, $^3J_{HH}$=4.4 Hz, 1H, CH), 3.13 (dd, $^2J_{HH}$=15.2 Hz, $^3J_{HH}$=4.0 Hz, 1H, CH$_2$), 2.79-2.86 (m, 1H, CH$_2$), 1.52 (d, $^3J_{HH}$=6.4 Hz, 3H, CH$_2$), 1.35 (t, $^3J_{HH}$=7.2 Hz, 3H, OCH$_2$CH$_3$), HRMS (ESI) calcd for C$_{18}$H$_{18}$N$_2$O$_2$ (M+H)$^+$ 259.1441. found 259.1443.

Compounds I$_b$-7–I$_b$-12 are completed through repeating the foregoing steps

(S)-2,3,4,9-tetrahydropyridino [3,4-b] indol-3-ethyl formate (I$_b$-7)

Light yellow solid, yield 95%, melting point 50-53° C.;
$^1$H NMR (400 MHz, CDCl$_3$) δ 7.81 (s, 1H, NH), 7.48 (d, $^3J_{HH}$=7.6 Hz, 1H, Ar—H), 7.32 (d, $^3J_{HH}$=8.0 Hz, 1H, Ar—H), 7.17 (t, $^3J_{HH}$=7.2 Hz, 1H, Ar—H), 7.11 (t, $^3J_{HH}$=7.2 Hz, 1H, Ar—H), 4.25-4.30 (m, 3H, CH and OCH$_2$), 3.83-3.86 (m, 4H, CH and OCH$_3$), 3.11-3.16 (m, 1H, CH$_2$), 2.80-2.87 (m, 1H, CH$_2$), 1.51 (d, $^3J_{HH}$=6.8 Hz, 3H, CH$_3$), HRMS (ESI) calcd for C$_{16}$H$_{16}$N$_2$O$_2$ (M+H)$^+$ 245.1285. found 245.1288.

(1S, 3S)-1-methyl-2,3,4,9-tetrahydropyridino [3,4-b] indol-3-butyl formate (I$_b$-8)

Yellow oily substance, yield 68%;
$^1$H NMR (400 MHz, CDCl$_3$) δ 7.78 (s, 1H, NH), 7.49 (d, $^3J_{HH}$=7.6 Hz, 1H, Ar—H), 7.33 (d, $^3J_{HH}$=8.0 Hz, 1H, Ar—H), 7.17 (t, $^3J_{HH}$=7.2 Hz, 1H, Ar—H), 7.11 (t, $^3J_{HH}$=7.2 Hz, 1H, Ar—H), 4.26-4.31 (m, 1H, CHCH$_2$), 4.23 (t, $^3J_{HH}$=6.8 Hz, 2H, CH$_2$O), 3.82 (dd, $^3J_{HH}$=7.2 Hz, $^3J_{HH}$=4.4 Hz, 1H, CHCO), 3.10-3.16 (m, 1H, CH$_2$), 2.78-2.85 (m, 1H, CH$_2$), 1.67-1.74 (m, 2H, OCH$_2$CH$_2$), 1.52 (d, $^3J_{HH}$=6.8 Hz, 3H, CHCH$_3$), 1.41-1.48 (m, 2H, CH$_2$CH$_3$), 0.97 (t, $^3J_{HH}$=7.2 Hz, 3H, CH$_2$CH$_3$). HRMS (ESI) calcd for C$_{17}$H$_{23}$N$_2$O$_2$ (M+H)$^+$ 287.1754. found 287.1759.

2,3,4,9-tetrahydropyridino [3,4-b] indol-3-ethyl formate (I$_b$-9)

Yellow solid, yield 90%, melting point 136-137° C.;
$^1$H NMR (400 MHz, CDCl$_3$) δ 7.80 (s, 1H, NH), 7.49 (d, $^3J_{HH}$=7.6 Hz, 1H, Ar—H), 7.31 (d, $^3J_{HH}$=8.0 Hz, 1H, Ar—H), 7.16 (d, $^3J_{HH}$=7.2 Hz, $^4J_{HH}$=4.8 Hz, 1H, Ar—H), 7.08-7.12 (m, 1H, Ar—H), 4.26 (q, $^3J_{HH}$=6.8 Hz, 2H, OCH$_3$), 4.10-4.19 (m, 2H, CH$_2$NH), 3.79 (q, $^3J_{HH}$=4.8 Hz, 1H, CHCO), 3.14 (q, 1H, $^3J_{HH}$=7.2 Hz, 1H, CHCO$_2$Et), 3.14 (dd, $^2J_{HH}$=15.2 Hz, $^3J_{HH}$=4.8 Hz, 1H, CH$_2$), 2.85-2.96 (d, $^3J_{HH}$=6.4 Hz, 1H, CH$_2$), 1.93 (br, 1H, NH), 1.33 (t, $^3J_{HH}$=6.8 Hz, 3H, OCH$_2$CH$_3$), HRMS (ESI) calcd for C$_{17}$H$_{23}$N$_2$O$_2$ (M+H)$^+$ 245.1285. found 245.1280.

(1S, 3S)-1-ethyl-2,3,4,9-tetrahydropyridino [3,4-b] indol-3-ethyl formate (I$_b$-10)

Yellow oily substance, yield 68%;
$^1$H NMR (400 MHz, CDCl$_3$) δ 7.49 (d, $^3J_{HH}$=7.6 Hz, 1H, Ar—H), 7.33 (d, $^3J_{HH}$=8.0 Hz, 1H, Ar—H), 7.14-7.18 (m, 1H, Ar—H), 7.09-7.13 (m, 1H, Ar—H), 4.26-4.32 (m, 2H, OCH$_3$), 4.15-4.18 (m, H, CHNH), 3.78 (dd, $^3J_{HH}$=11.2 Hz, $^3J_{HH}$=4.0 Hz, 1H, CHCO), 3.11-3.16 (m, 1H, CH$_2$), 2.77-2.84 (m, 1H, CH$_2$), 1.71-1.84 (m, 2H, CH$_3$CH$_2$), 1.35 (t, $^3J_{HH}$=7.2 Hz, 3H, OCH$_2$CH$_3$), 1.90 (t, $^3J_{HH}$=7.2 Hz, 3H, CH$_2$CH$_3$), HRMS (ESI) calcd for C$_{16}$H$_{21}$N$_2$O$_2$ (M+H)$^+$ 273.1598. found 273.1602.

(1S, 3S)-1-(pyridine-3)-2,3,4,9-tetrahydropyridino [3,4-b] indol-3-ethyl formate (I$_b$-11)

White solid, yield 42%, melting point 239-240° C.;
$^1$H NMR (400 MHz, CDCl$_3$) δ 8.62 (d, $^3J_{HH}$=1.6 Hz, 1H, Ar—H), 8.55 (dd, $^3J_{HH}$=4.4 Hz, $^4J_{HH}$=1.6 Hz, 1H, Ar—H), 7.94 (s, 1H, NH), 7.72 (dt, $^3J_{HH}$=7.6 Hz, $^3J_{HH}$=1.6 Hz, 1H, Ar—H), 7.55-7.58 (m, 1H, Ar—H), 7.24-7.29 (m, 2H, Ar—H), 7.11-7.19 (m, 2H, Ar—H), 5.31 (s, 1H, CHAr), 4.28-4.31 (m, 2H, OCH$_2$CH$_2$), 3.97 (dd, $^3J_{HH}$=11.2 Hz, $^3J_{HH}$=4.0 Hz, 1H, CHCOOMe), 3.26 (ddd, $^3J_{HH}$=14.8 Hz, $^3J_{HH}$=4.0 Hz, $^4J_{HH}$=1.6 Hz, 1H, CH$_2$), 2.98-3.05 (m, 1H, CH$_2$), 1.35 (t, $^3J_{HH}$=6.8 Hz, 3H, OCH$_2$CH$_3$), HRMS (ESI) calcd for C$_{19}$H$_{20}$N$_3$O$_2$ (M+H)$^+$ 322.1550. found 322.1552.

(1R,3R)-1-methyl-2,3,4,9-tetrahydropyridino [3,4-b] indol-3-ethyl formate (I$_b$-12)

Light yellow solid, yield 92%, melting point 121-122° C.;
$^1$H NMR (400 MHz, CDCl$_3$) δ 7.83 (s, 1H, NH), 7.49 (d, $^3J_{HH}$=7.6 Hz, 1H, Ar—H), 7.32 (d, $^3J_{HH}$=7.6 Hz, 1H, Ar—H), 7.16 (d, $^3J_{HH}$=7.2 Hz, $^4J_{HH}$=1.2 Hz, 1H, Ar—H), 7.11 (td, $^3J_{HH}$=7.2 Hz, $^4J_{HH}$=0.8 Hz, 1H, Ar—H), 4.26-4.31 (m, 3H, CH and OCH$_2$), 3.81 (dd, $^3J_{HH}$=11.2 Hz, $^3J_{HH}$=4.4 Hz, 1H, CH), 3.13 (ddd, $^3J_{HH}$=15.2 Hz, $^3J_{HH}$=4.4 Hz, $^4J_{HH}$=2.0 Hz, 1H, CH$_2$), 2.82 (ddd, $^3J_{HH}$=14.8 Hz, $^3J_{HH}$=11.2 Hz, $^4J_{HH}$=2.4 Hz, 1H, CH$_2$), 1.51 (d, $^3J_{HH}$=6.8 Hz, 3H, CH$_3$), 1.35 (t, $^3J_{HH}$=7.2 Hz, 3H, OCH$_3$CH$_3$), HRMS (ESI) calcd for C$_{13}$H$_{19}$N$_2$O$_2$ (M+H)$^+$ 259.1441. found 259.1443.

Embodiment 13: 1-methyl-pyridino [3,4-b] indol-3-ethyl formate (I$_a$-10) and 1-methyl-pyridino [3,4-b] indol-3-formic acid (I$_a$-11)

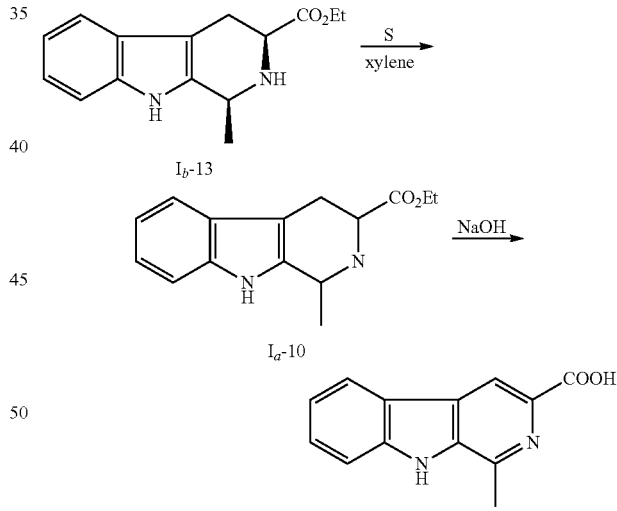

1-methyl-pyridino [3,4-b] indol-3-ethyl formate (I$_a$-10)

Add 12.4 g (47.7 mmol) of tetrahydrocarboline, 3.1 g (95.4 mmol) of elemental sulfur and 150 mL of xylol to a 250 mL single-necked flask, and heat and reflux them for 12 h. Cool them to separate out flesh pink solid, and conduct suction filtration to obtain 8.4 g of flesh color solid. Yellow solid, yield 69%, melting point 217-219° C.;
$^1$H NMR (400 MHz, CDCl$_3$) δ 9.60 (s, 1H, NH), 8.79 (s, 1H, Ar—H), 8.18 (d, $^3J_{HH}$=8.0 Hz, Ar—H), 7.54-7.60 (m, 2H, Ar—H), 7.32-7.36 (m, 1H, Ar—H), 4.50 (d, $^3J_{HH}$=6.8 Hz, 2H, OCH$_2$), 2.79 (s, 3H, CH$_3$), 1.41 (t, $^3J_{HH}$=7.2 Hz, 3H, OCH$_2$CH$_3$), HRMS (ESI) calcd for C$_{15}$H$_{19}$N$_2$O$_2$ (M+H)$^+$ 227.0815. found 227.0811.

1-methyl-pyridino [3,4-b] indol-3-formic acid (I$_a$-11)

Add 2.00 g (7.87 mmol) of ester, 0.47 g (11.81 mmol) of NaOH and 60 mL of ethanol to a 100 mL single-necked flask, and heat and reflux them for 6 h. Use 3M diluted hydrochloric acid to regulate pH value to 5-6 and generate precipitate, conduct suction filtration, wash filter cakes with water and dry them to obtain 1.46 g of light yellow solid. The yield is 82% and the melting point is above 300° C.;

$^1$H NMR (400 MHz, d$_6$-DMSO) δ 12.04 (s, 1H, COOH), 8.77 (s, 1H, Ar—H), 8.36 (d, $^3J_{HH}$=8.0 Hz, 1H, Ar—H), 7.66 (d, $^3J_{HH}$=8.0 Hz, 1H, Ar—H), 7.60 (t, $^3J_{HH}$=7.0 Hz, 1H, Ar—H), 7.30 (d, $^3J_{HH}$=7.2 Hz, 1H, Ar—H), 7.31 (d, $^3J_{HH}$=7.2 Hz, 1H, Ar—H), 2.82 (s, 3H, CH$_3$). HRMS (ESI) calcd for C$_{13}$H$_{11}$N$_2$O$_2$ (M+H)$^+$ 255.1128. found 255.1131.

Embodiment 14: Synthesis of (E)-3-(1-methyl-pyridino [3,4-b] indol-3)-acrylic acid (I$_a$-14)

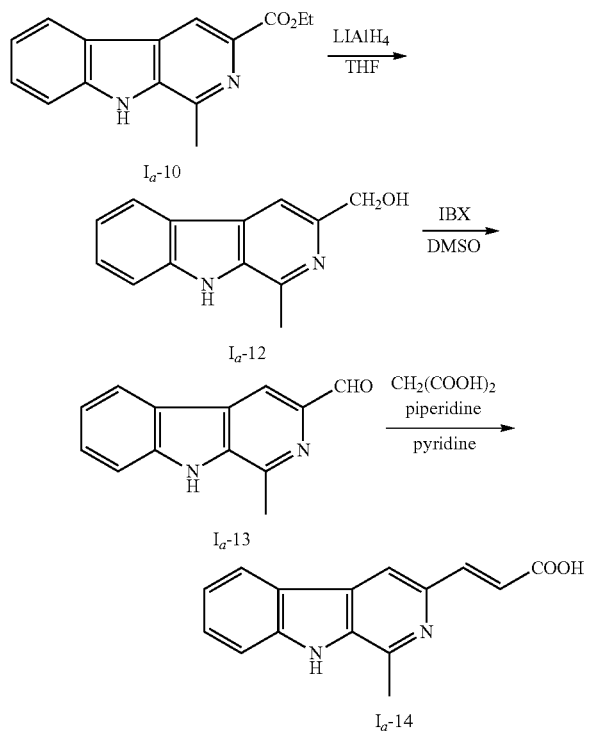

(1-methyl-pyridino [3,4-b] indol-3)-methanol (I$_a$-12)

Add 2 g (7.4 mmol) of ester and 300 mL of tetrahydrofuran to a 500 mL single-necked flask, add 0.6 g (15.7 mmol) of lithium aluminum hydride by batch, stir them at room temperature overnight, add water to quench the reaction, conduct suction filtration and remove the solvent of the filtrate to obtain 1.58 g of yellow solid. The yield is 95% and the melting point is 195-197° C.;

$^1$H NMR (400 MHz, d$_6$-DMSO) δ 11.46 (s, 1H, NH), 8.19 (d, $^3J_{HH}$=8.0 Hz, 1H, Ar—H), 7.95 (s, 1H, Ar—H), 7.56 (d, $^3J_{HH}$=8.0 Hz, 1H, Ar—H), 7.49-7.53 (m, 1H, Ar—H), 7.18-7.22 (m, 1H, Ar—H), 5.30 (t, $^3J_{HH}$=6.0 Hz, 1H, OH), 4.67 (d, $^3J_{HH}$=6.0 Hz, 2H, CH$_2$OH), 2.73 (s, 3H, CH$_3$).

1-methyl-pyridino [3,4-b] indol-3-formaldehyde (I$_a$-13)

Add 1.16 g (5.47 mmol) of alcohol, 3.04 g (10.93 mmol) of IBX and 60 mL of DMSO to a 100 mL single-necked flask, and stir them at room temperature overnight. Add 200 mL of water, use dichloromethane for extraction, wash the organic phase with a saturated saline solution, dry it with anhydrous sodium sulfate, remove the solvent, and use dichloromethane/methanol (10:1) for column chromatography under normal pressure to obtain 0.46 g of white solid. The yield is 40% and the melting point is 194-196° C.;

$^1$H NMR (400 MHz, d$_6$-DMSO) δ 12.17 (s, 1H, NH), 10.07 (s, 1H, CHO), 8.68 (s, 1H, Ar—H), 8.38 (d, $^3J_{HH}$=7.6 Hz, 1H, Ar—H), 7.68 (d, $^3J_{HH}$=8.0 Hz, 1H, Ar—H), 7.61 (t, $^3J_{HH}$=7.6 Hz, 1H, Ar—H), 7.33 (t, $^3J_{HH}$=7.6 Hz, 1H, Ar—H), 2.87 (s, 3H, CH$_3$).

(E)-3-(1-methyl-pyridino [3,4-b] indol-3)-acrylic acid (I$_a$-14)

Add 0.45 g (2.14 mmol) of aldehyde, 100 mL of pyridine and 3 drops of piperidine to a 250 mL single-necked flask, add 0.33 g (3.21 mmol) of malonic acid, and heat and react for 4 h. Use 3M diluted hydrochloric acid to regulate pH value of the water phase to 5-6, and conduct suction filtration to obtain 0.51 g of yellow solid. The yield is 94% and the melting point is 220-223° C.; $^1$H NMR (400 MHz, d$_6$-DMSO) δ 12.22 (s, 1H, NH), 11.85 (s, 1H, COOH), 8.31 (s, 1H, Ar—H), 8.21 (d, $^3J_{HH}$=7.6 Hz, 1H, Ar—H), 7.72 (d, $^3J_{HH}$=15.2 Hz, 1H, CHCH), 7.62 (d, $^3J_{HH}$=7.6 Hz, 1H, Ar—H), 7.56 (t, $^3J_{HH}$=7.6 Hz, 1H, Ar—H), 7.28 (t, $^3J_{HH}$=7.6 Hz, 1H, Ar—H), 6.78 (d, $^3J_{HH}$=15.6 Hz, 1H, CHCH), 2.80 (s, 3H, CH$_2$); HRMS (ESI) calcd for C$_{15}$H$_{13}$N$_2$O$_2$ (M+H)$^+$ 253.0972. found 253.0975.

Compounds I$_a$-15-I$_a$-16 are completed through repeating the foregoing steps (E)-3-(1-(thiophene-2)-pyridino [3,4-b] indol-3)-acrylic acid (I$_a$-15)

Yellow solid, yield 85%, melting point 248-250° C.;
$^1$H NMR (400 MHz, d$_6$-DMSO) δ 12.43 (s, 1H, NH), 12.10 (s, 1H, COOH), 8.47 (s, 1H, Ar—H), 8.28 (d, $^3J_{HH}$=8.0 Hz, 1H, Ar—H), 8.17 (d, $^3J_{HH}$=3.2 Hz, 1H, Ar—H), 7.80 (d, $^3J_{HH}$=4.8 Hz, 1H, Ar—H), 7.77-7.80 (m, 2H, Ar—H), 7.62 (t, $^3J_{HH}$=7.2 Hz, 1H, Ar—H), 7.33-7.38 (m, 2H, Ar—H and CHCH), 6.88 (d, $^3J_{HH}$=15.6 Hz, 1H, CHCH), 6.93 (d, $^3J_{HH}$=15.6 Hz, 1H, CHCH); HRMS (ESI) calcd for C$_{18}$H$_{32}$N$_2$O$_2$ (M+H)$^+$ 321.0692. found 321.0694.

(E)-3-(1-(pyridine-3)-pyridino [3,4-b] indol-3)-acrylic acid (I$_a$-16)

Yellow solid, yield 50%, melting point>300° C.;
$^1$H NMR (400 MHz, d$_6$-DMSO) δ 12.43 (s, 1H, NH), 12.10 (s, 1H, COOH), 9.31 (d, $^3J_{HH}$=1.6 Hz, 1H, Ar—H), 8.81 (d, $^3J_{HH}$=4.8 Hz, 1H, Ar—H), 8.61 (s, 1H, Ar—H), 8.56-8.59 (m, 1H, Ar—H), 8.31 (d, $^3J_{HH}$=7.6 Hz, 1H, Ar—H), 7.84 (d, $^3J_{HH}$=15.6 Hz, 1H, CHCH), 7.76 (dd, $^3J_{HH}$=7.6 Hz, $^3J_{HH}$=4.8 Hz, 1H, Ar—H), 7.70 (d, $^3J_{HH}$=8.0

Hz, 1H, Ar—H), 7.62 (t, $^3J_{HH}$=7.2 Hz, 1H, Ar—H), 7.35 (t, $^3J_{HH}$=7.2 Hz, 1H, Ar—H), 6.93 (d, $^3J_{HH}$=15.6 Hz, 1H, CHCH),

Embodiment 15: Synthesis of 1-methyl-4,9-dihydro-pyridino [3,4-b] indol-3-)ethyl formate ($I_b$-14)

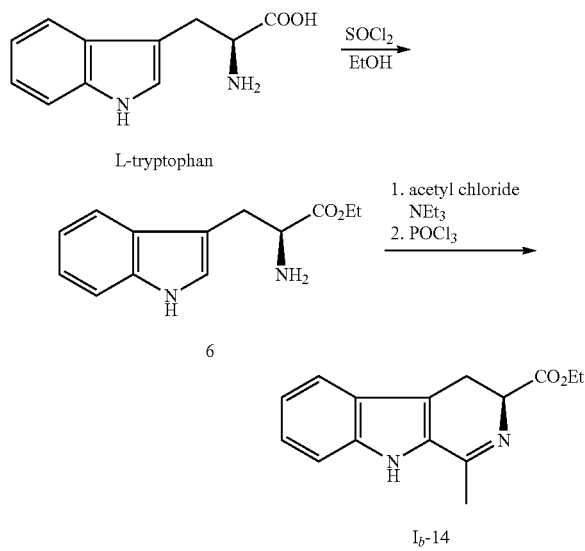

L-tryptophan ethyl ester (6)

Add 0.50 g (24.50 mmol) of L-tryptophan and 150 mL of ethanol to a 250 mL single-necked flask, add 15 mL of thionyl chloride, and heat and reflux them for 12 h. Remove the solvent to obtain 5.72 g of brown viscous substance, with a yield of 98%;

$^1$H NMR (400 MHz, CDCl$_3$) δ 8.10 (s, 1H, NH), 7.62 (d, $^3J_{HH}$=7.6 Hz, 1H, Ar—H), 7.37 (d, $^3J_{HH}$=80 Hz, 1H, Ar—H), 7.20 (t, $^3J_{HH}$=7.2 Hz, 1H, Ar—H), 7.13 (t, $^3J_{HH}$=7.2 Hz, 1H, Ar—H), 7.08 (s, 1H, Ar—H), 4.14-4.19 (m, 2H, OCH$_2$), 3.82 (dd, $^3J_{HH}$=7.6 Hz, $^3J_{HH}$=5.2 Hz, 1H, CH), 3.29 (dd, $^3J_{HH}$=14.4 Hz, $^3J_{HH}$=5.2 Hz, 1H, CH$_2$), 3.05 (dd, $^3J_{HH}$=14.4 Hz, $^3J_{HH}$=8.0 Hz, 1H, CH$_2$), 1.24 (t, $^3J_{HH}$=7.2 Hz, 3H, OCH$_2$CH$_3$).

1-methyl-4, 9-dihydro-pyridino [3,4-b] indol-3-ethyl formate ($I_b$-14)

Add 5.72 g (24.66 mmol) of tryptophan ethyl ester, 150 mL of dichloromethane and 2.99 g (29.59 mmol) of triethylamine to a 250 mL single-necked flask, add 2.13 g (27.12 mmol) of acetylchloride and stir them at room temperature for 5 h after dropwise addition. Use a saturated sodium bicarbonate to wash the reaction solution, extract with dichloromethane, wash the organic phase with a saturated saline solution, dry it with anhydrous sodium sulfate and remove the solvent to obtain 5.96 g of brown viscous substance. Dissolve it in chloroform, add 24 mL of POCl$_3$, and heat and reflux them for 5 h. Extract with dichloromethane, dry with anhydrous sodium sulfate, remove the solvent, and use dichloromethane/methanol (10:1) for column chromatography under normal pressure to obtain 2.85 g of yellow solid. Yellow solid, yield 45%, melting point 85-87° C.;

$^1$H NMR (400 MHz, CDCl$_3$) δ 8.33 (s, 1H, NH), 7.61 (d, $^3J_{HH}$=8.0 Hz, 1H, Ar—H), 7.41 (d, $^3J_{HH}$=8.0 Hz, 1H, Ar—H), 7.30 (t, $^3J_{HH}$=8.0 Hz, 1H, Ar—H), 7.17 (t, $^3J_{HH}$=8.0 Hz, 1H, Ar—H), 4.43-4.48 (m, 1H, CHCO$_2$Et), 4.31 (q, $^3J_{HH}$=7.2 Hz, OCH$_2$), 3.25 (dd, $^3J_{HH}$=16.4 Hz, $^3J_{HH}$=7.6 Hz, 1H, CH$_2$CH), 3.08 (dd, $^3J_{HH}$=16.4 Hz, $^3J_{HH}$=14.8 Hz, 1H, CH$_2$CH), 2.43 (d, $^3J_{HH}$=2.0 Hz, 3H, CH$_3$), 1.34 (t, $^3J_{HH}$=7.2 Hz, 3H, OCH$_2$CH$_3$), HRMS (ESI) calcd for C$_{15}$H$_{17}$N$_2$O$_2$ (M+H)$^+$ 247.1285. found 257.1287.

Embodiment 16: (1S, 3S)-1-methyl-2,3,4,9-tetrahydropyridino [3,4-b] indol-3-formylhydrazine ($I_b$-15)

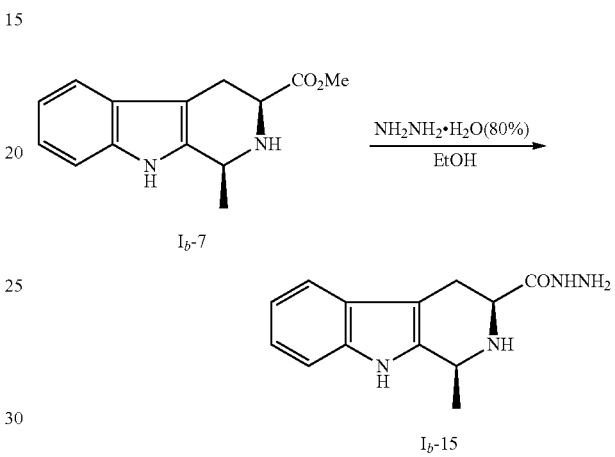

Add 1.00 g (4.1 mmol) of methyl ester, 50 mL of ethanol and 1.02 g (16.4 mmol) of 80% hydrazine hydrate to a 100 mL single-necked flask, and heat and reflux them for 6 h. Remove the solvent, dissolve it in ethyl acetate, wash it with a saturated saline solution, dry it with anhydrous sodium sulfate, and remove the solvent to obtain 0.98 g of light yellow solid, with a yield of 98%. White solid, yield 98% and melting point 100-103° C.;

$^1$H NMR (400 MHz, CDCl$_3$) δ 8.15 (s, 1H, NH), 7.90 (s, 1H, NHCO), 7.50 (d, $^3J_{HH}$=7.6 Hz, 1H, Ar—H), 7.32 (d, $^3J_{HH}$=8.0 Hz, 1H, Ar—H), 7.17 (t, $^3J_{HH}$=7.2 Hz, 1H, Ar—H), 7.11 (t, $^3J_{HH}$=7.2 Hz, 1H, Ar—H), 4.18-4.23 (m, 1H, CHCH$_3$), 3.93 (br, 2H, NH$_2$), 3.65 (q, $^3J_{HH}$=8.4 Hz, 1H, CHCO), 3.26-3.32 (m, 1H, CH$_2$), 2.71-2.78 (m, 1H, CH$_2$), 1.48 (d, $^3J_{HH}$=6.8 Hz, 3H, CH$_3$), HRMS (ESI) calcd for C$_{13}$H$_{12}$N$_4$O (M+H)$^+$ 245.1397. found 245.1398.

Embodiment 17: Synthesis of (1S, 3S)—N-butyl-1-methyl-2,3,4,9-tetrahydro-pyridino [3,4-b] indol-3-formamide ($I_b$-16)

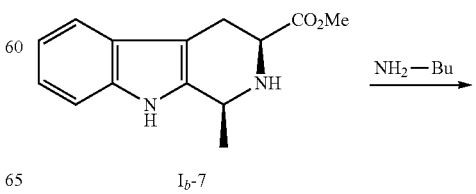

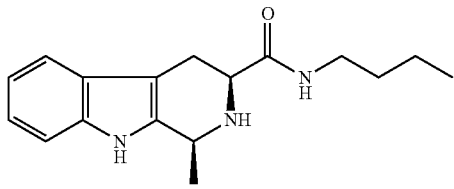

I<sub>b</sub>-16

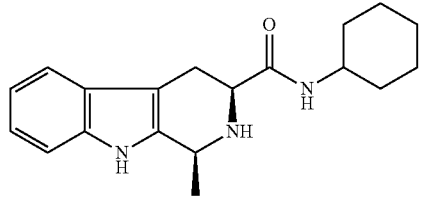

I<sub>b</sub>-17

Add 0.5 g (2.05 mmol) of methyl ester and 15 mL of n-butylamine to a 25 mL single-necked flask, and stir them at room temperature overnight. Remove the solvent, add dichloromethane to dissolve it, wash it with a saturated saline solution, dry with anhydrous sodium sulfate and remove the solvent. Use dichloromethane/methanol (20:1) for column chromatography under normal pressure to obtain 0.35 g of white solid. The yield is 60% and the melting point is 207-210° C.;

$^1$H NMR (400 MHz, CDCl$_3$) δ 8.02 (s, 1H, NH), 7.49 (d, $^3J_{HH}$=8.0 Hz, 1H, Ar—H), 7.31 (d, $^3J_{HH}$=7.6 Hz, 1H, Ar—H), 7.15 (t, $^3J_{HH}$=7.2 Hz, 1H, Ar—H), 7.10 (t, $^3J_{HH}$=7.2 Hz, 1H, Ar—H), 4.17-4.22 (m, 1H, CHCH$_3$), 3.58 (dd, $^3J_{HH}$=11.2 Hz, $^3J_{HH}$=4.4 Hz, 1H, CHCO), 3.28-3.38 (m, 3H, CHCH$_2$ and NHCH$_2$), 2.37-2.74 (m, 1H, CH$_2$), 1.51-1.59 (m, 2H, NHCH$_2$CH$_2$), 1.49 (d, $^3J_{HH}$=10.8 Hz, 3H, CHCH$_3$), 1.34-1.43 (m, 2H, CH$_2$CH$_3$), 0.95 (t, $^3J_{HH}$=7.22 Hz, 3H, CH$_2$CH$_3$); HRMS (ESI) calcd for C$_{13}$H$_{24}$N$_2$O (M+H)$^+$ 286.1914. found 286.1919.

Compound I$_b$-18 is completed through repeating the foregoing steps (1S, 3S)—N-(2-ethoxyl)-1-methyl-2,3,4,9-tetra-hydro-pyridino [3,4-b] indol-3-formamide (I$_b$-18)

White solid, yield 64%, melting point 110-112° C.;

1H NMR (400 MHz, d$_6$-methanol) δ 7.39 (d, $^3J_{HH}$=7.6 Hz, 1H, Ar—H), 7.29 (d, $^3J_{HH}$=8.0 Hz, 1H, Ar—H), 7.04-7.07 (m, 1H, Ar—H), 6.95-6.99 (m, 1H, Ar—H), 4.18 (q, $^3J_{HH}$=6.8 Hz, 1H, CHCH$_3$), 3.67 (t, $^3J_{HH}$=6.4 Hz, 2H, HOCH$_2$), 3.62 (dd, $^3J_{HH}$=11.2 Hz, $^3J_{HH}$=4.4 Hz, 1H, CHCO), 3.38-3.42 (m, 3H, NHCH$_2$), 3.30-3.32 (m, 1H, ?), 3.02-3.08 (m, 1H, CH$_2$CHCO), 2.72-2.80 (m, 1H, CH$_2$CHCO), 1.52 (d, $^3J_{HH}$=6.8 Hz, 3H, CHCH$_3$); HRMS (ESI) calcd for C$_{13}$H$_{30}$N$_2$O$_2$ (M+H)$^+$ 274.1550. found 274.1552.

Embodiment 18: Synthesis of (1S, 3S)—N-cyclo-hexyl-1-methyl-2,3,4,9-tetrahydro-pyridino [3,4-b] indol-3-formamide (I$_b$-17)

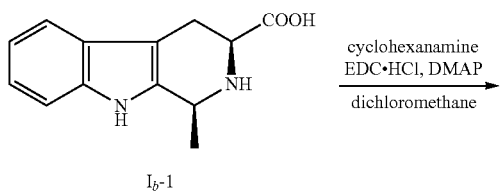

I$_b$-1 cyclohexanamine
EDC·HCl, DMAP
─────────────→
dichloromethane

White solid, yield 50%, melting point 231-233° C.;

$^1$H NMR (400 MHz, CDCl$_3$) δ 7.81 (s, 1H, NH), 7.51 (d, $^3J_{HH}$=8.0 Hz, 1H, Ar—H), 7.32 (d, $^3J_{HH}$=8.0 Hz, 1H, Ar—H), 7.14-7.18 (m, 1H, Ar—H), 7.09-7.13 (m, 1H, Ar—H), 6.94 (d, $^3J_{HH}$=8.0 Hz, 1H, NHCO), 4.19-4.24 (m, 1H, CHCH$_3$), 3.79-3.88 (m, 1H, NHCH), 3.57 (dd, $^3J_{HH}$=11.2 Hz, $^3J_{HH}$=4.8 Hz, 1H, CHCO), 3.28-3.33 (m, 1H, COCHCH$_2$), 2.67-2.74 (m, 1H, COCHCH$_2$), 1.93-1.99 (m, 2H, CH$_2$), 1.73-1.73 (m, 2H, CH$_2$), 1.58-1.67 (m, 2H, CH$_2$), 1.50 (d, $^3J_{HH}$=8.0 Hz, 3H, CHCH$_3$), 1.36-1.43 (m, 2H, CH$_2$), 1.18-1.26 (m, 2H, CH$_2$), HRMS (ESI) calcd for C$_{19}$H$_{36}$N$_9$O (M+H)$^+$ 312.2070. found 312.2076.

Compounds I$_b$-19, I$_b$-20 are completed through repeating the foregoing steps (1S, 3S)—N-((dimethyl amino)methyl)-1-methyl-2,3,4,9-tetrahydro-pyridino [3,4-b] indol-3-formamide (I$_b$-19)

White solid, yield 55%;

mp=110-112° C.; $^1$H NMR (400 MHz, CDCl$_3$) δ 7.87 (s, 1H, Ar—NH), 7.51 (d, $^3J_{HH}$=8.0 Hz, 1H, Ar—H), 7.32 (d, $^3J_{HH}$=7.6 Hz, 1H, Ar—H), 7.28 (m, 1H, CONH), 7.16 (t, $^3J_{HH}$=7.2 Hz, 1H, Ar—H), 7.11 (t, $^3J_{HH}$=7.2 Hz, 1H, Ar—H), 4.22 (q, $^3J_{HH}$=6.8 Hz, 1H, CH), 3.61 (d, $^3J_{HH}$=4.4 Hz, $^3J_{HH}$=11.2 Hz, 1H, CH), 3.51-3.36 (m, 2H, N—CH$_2$), 3.28 (ddd, $^3J_{HH}$=2.0 Hz, $^3J_{HH}$=4.4 Hz, $^2J_{HH}$=16.0 Hz, 1H, CH$_2$), 2.74 (ddd, $^4J_{HH}$=2.4 Hz, $^3J_{HH}$=11.2 Hz, $^2J_{HH}$=160 Hz, 1H, CH$_2$), 2.48 (t, $^3J_{HH}$=6.4 Hz, 2H, CH$_2$), 2.27 (s, 6H, CH$_3$), 1.50 (d, $^3J_{HH}$=6.8 Hz, 3H, CH$_2$); HRMS (ESI) calcd for C$_{17}$H$_{23}$N$_4$O (M+H)$^+$ 301.2023. found 301.2027.

(1S, 3S)—N-((tetrahydrofuran-2)-methyl)-1-methyl-2,3,4,9-tetrahydro-pyridino [3,4-b] indol-3-forma-mide (I$_b$-20)

Yellow solid, yield 47%, melting point 95-97° C.;

$^1$H NMR (400 MHz, CDCl$_3$) δ 7.81 (s, 1H, NH), 7.55 (d, $^3J_{HH}$=7.6 Hz, 1H, Ar—H), 7.40-7.45 (m, 1H, NHCO), 7.36 (d, $^3J_{HH}$=7.6 Hz, 1H, Ar—H), 7.20 (t, $^3J_{HH}$=7.6 Hz, 1H, Ar—H), 7.14 (t, $^3J_{HH}$=7.6 Hz, 1H, Ar—H), 4.25 (q, $^3J_{HH}$=6.8 Hz, 1H, CHCH$_3$), 4.04-4.10 (m, 1H, CHO), 3.90-3.95 (m, 1H, CH$_2$O), 3.83 (dd, $^3J_{HH}$=7.2 Hz, $^3J_{HH}$=15.2 Hz, 1H, CHCO), 3.63-3.70 (m, 2H, CH$_2$O and CH$_2$NH), 3.35 (dd, $^3J_{HH}$=16.0 Hz, $^3J_{HH}$=4.4 Hz, 1H, CH$_2$CH), 3.18-3.30 (m, 1H, CH$_2$NH), 2.72-2.79 (m, 1H, CH$_2$CH), 2.02-2.98 (m, 1H, CH$_2$CH$_2$), 1.92-1.99 (m, 2H, CH$_2$CH$_2$), 1.59-1.65 (m, 1H, CH$_2$CH$_2$), 1.53 (d, $^3J_{HH}$=6.8 Hz, 3H, CHCH$_3$), HRMS (ESI) calcd for C$_{18}$H$_{23}$N$_2$O$_1$(M+H)$^+$ 314.1863. found 314.1867.

Embodiment 19: (1S, 3S)—N'-benzylidene-1-methyl-2,3,4,9-tetrahydropyridino [3,4-b] indol-3-formylhydrazine (I$_c$-1)

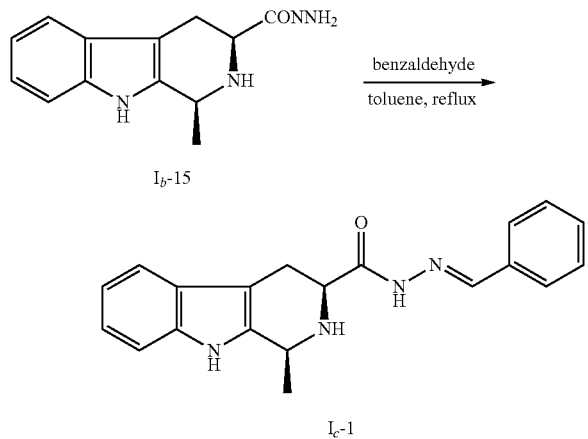

Add 0.50 g (2.05 mmol) of hydrazide and 40 mL of toluene to a 100 mL single-necked flask, add 0.44 g (4.10 mmol) of benzaldehyde, and heat and reflux them for 5 h. Conduct suction filtration and wash with toluene to obtain 0.50 g of yellow solid. The yield is 74% and the melting point is 200-204° C.;

$^1$H NMR (400 MHz, DMSO-d$_6$) δ 11.48 and $^3J_{HH}$=7.6 Hz, 1H, Ph-H), 7.49-7.42 (m, 2H, Ph-H), 7.42-7.33 (m, 2H, Ph-H and Ar—H), 7.31 and 7.30 (d, $^3J_{HH}$=8.0 Hz, 1H, Ar—H), 7.03 (t, $^3J_{HH}$=7.2 Hz, 1H, Ar—H), 6.95 and 6.92 (t, $^3J_{HH}$=7.2 Hz, 1H, Ar—H), 4.48 and 3.61 (dd, $^3J_{HH}$=10.8 Hz, 3.6 Hz, 1H, CH), 4.15 (d, $^3J_{HH}$=8.0 Hz, 1H, CH), 2.98-2.89 (m, 1H, CH$_2$), 2.71 and 2.62 (ddd, $^3J_{HH}$=2.0 Hz, $^3J_{HH}$=11.6 Hz, $^3J_{HH}$=14.4 Hz, 1H, CH$_2$), 1.45 (d, $^3J_{HH}$=6.8 Hz, 3H, CH$_3$), HRMS (ESI) calcd for C$_{30}$H$_{21}$N$_4$O[M+H]$^+$ 333.1710. found 333.1715.

Compounds I$_c$-2-I$_c$-29 are completed through repeating the foregoing steps

(1S, 3S)—N'-(4-tert-butyl benzylidene)-1-methyl-2,3,4,9-tetrahydropyridino [3,4-b] indol-3-formylhydrazine (I$_c$-2)

Yellow solid, yield 72%, melting point 139-143° C.;
$^1$H NMR (400 MHz, DMSO-d$_6$) δ 11.47 and 11.32 (s, 1H, NH), 10.87 and 10.82 (s, 1H, O═C—NH), 8.31 and 8.03 (s, 1H, N═CH), 7.88 and 7.70-7.27 (m, 6H, Ph-H and Ar—H), 7.04 (t, $^3J_{HH}$=6.8 Hz, 1H, Ar—H), 6.96 (t, $^3J_{HH}$=7.2 Hz, 1H, Ar—H), 4.48 and 3.62 (dd, $^3J_{HH}$=10.4 Hz, 7.2 Hz, 1H, CH), 4.27-4.08 (m, 1H, CH), 3.02-2.88 (m, 1H, CH$_2$), 2.77-2.39 (m, 1H, CH$_2$), 1.52-1.35 (m, 3H, CH$_3$), 1.30 and 1.24 (s, 9H, CH$_3$); HRMS (ESI) calcd for C$_{24}$H$_{29}$N$_4$O (M+H)$^+$ 289.2336. found 389.2338.

(1S, 3S)—N'-(4-dimethyl amino benzylidene)-1-methyl-2,3,4,9-tetrahydropyridino [3,4-b] indol-3-formylhydrazine (I$_c$-3)

Yellow solid, yield 73%, melting point 215-220° C.;
$^1$H NMR (400 MHz, DMSO-d$_6$) δ 11.20 and 11.05 (s, 1H, NH), 10.84 and 10.80 (s, 1H, O═C—NH), 8.16 and 7.92 (s, 1H, N═CH), 7.52 and 7.36 (d, $^3J_{HH}$=7.6 Hz, 2H, Ph-H), 7.44-7.38 (m, 1H, Ar—H), 7.30 (d, $^3J_{HH}$=6.4 Hz, 1H, Ar—H), 7.03 (t, $^3J_{HH}$=6.8 Hz, 1H, Ar—H), 6.95 (t, $^3J_{HH}$=6.8 Hz, 1H, Ar—H), 6.75 and 6.67 (d, $^3J_{HH}$=7.0 Hz, 2H, Ph-H), 4.44 and 3.57 (d, $^3J_{HH}$=8.8 Hz, 1H, CH), 4.23-4.08 (m, 1H, CH), 3.07-2.86 (m, 7H, N—CH$_3$ and CH$_2$), 2.74-2.56 (m, 1H, CH$_2$), 1.52-1.38 (m, 3H, CH$_3$); HRMS (ESI) calcd for C$_{32}$H$_{30}$N$_5$O [M+H]$^+$ 376.2132. found 376.2137.

(1S, 3S)—N'-(4-nitrobenzylidene)-1-methyl-2,3,4,9-tetrahydropyridino [3,4-b] indol-3-formylhydrazine (I$_c$-4)

Yellow solid, yield 74%, melting point 222-227° C.;
$^1$H NMR (400 MHz, DMSO-d$_6$) δ 11.81 and 11.68 (s, 1H, NH), 10.87 and 10.82 (s, 1H, O═C—NH), 8.46 and 8.17 (s, 1H, N═CH), 8.31 and 8.22 (d, $^3J_{HH}$=8.4 Hz, 2H, Ph-H), 7.98 and 7.88 (d, $^3J_{HH}$=8.4 Hz, 2H, Ph-h), 7.41 and 7.36 (d, $^3J_{HH}$=7.6 Hz, 1H, Ar—H), 7.31 (d, $^3J_{HH}$=6.4 Hz, 1H, Ar—H), 7.04 (t, $^3J_{HH}$=7.2 Hz, 1H, Ar—H), 6.96 (t, $^3J_{HH}$=7.6 Hz, 1H, Ar—H), 4.55 and 3.67 (d, $^3J_{HH}$=8.8 Hz, 1H, CH), 4.25-4.10 (m, 1H, CH), 2.86 (d, $^3J_{HH}$=13.6 Hz, 1H, CH$_2$), 2.79-2.60 (m, 1H, CH$_2$), 1.47 (d, $^3J_{HH}$=6.4 Hz, 3H, CH$_3$); HRMS (ESI) calcd for C$_{20}$H$_{30}$N$_3$O[M+H]$^+$ 378.1561. found 378.1563.

(1S, 3S)—N'-(4-chlorobenzylidene)-1-methyl-2,3,4,9-tetrahydropyridino [3,4-b] indol-3-formylhydrazine (I$_c$-5)

Yellow solid, yield 81%, melting point 140-145° C.;
$^1$H NMR (400 MHz, DMSO-d$_6$) δ 11.62 and 11.51 (s, 1H, NH), 10.91 and 10.85 (s, 1H, O═C—CH), 8.35 and 8.07 (s, 1H, N═CH), 7.74 and 7.64 (d, $^3J_{HH}$=7.2 Hz, 2H, Ph-H), 7.58-7.35 (m, 3H, Ph-H and Ar—H), 7.35-7.28 (m, 1H, Ar—H), 7.10-7.00 (m, 1H, CH$_2$), 2.79-2.62 (m, 1H, CH$_2$), 1.54-1.39 (m, 3H, CH$_3$); HRMS (ESI) calcd for C$_{21}$H$_{20}$N$_2$OCl[M+H]$^+$ 367.1320. found 367.1323.

(1S, 3S)—N'-(2, 4-dichlorobenzylidene)-1-methyl-2,3,4,9-tetrahydropyridino [3,4-b] indol-3-formylhydrazine (I$_c$-6)

yellow solid, yield 85%, melting point 211-213° C.;
$^1$H NMR (400 MHz, DMSO-d$_6$) δ 11.82 and 11.77 (s, 1H, NH), 10.91 and 10.84 (s, 1H, O═C—NH), 8.71 and 8.42 (s, 1H, N═CH), 8.00 and 7.85 (d, $^3J_{HH}$=8.4 Hz, 1H, Ph-H), 7.73 and 7.71 (d, $^3J_{HH}$=2.0 Hz, 1H, Ph-H), 7.53 and 7.43-7.35 (dd, $^4J_{HH}$=2.0 Hz, $^3J_{HH}$=8.4 Hz, 1H, Ph-H), 7.41 and 7.37 (d, $^3J_{HH}$=8.0 Hz, 1H, Ar—H), 7.32 and 7.31 (d, $^3J_{HH}$=8.0 Hz, 1H, Ar—H), 7.04 (t, $^3J_{HH}$=7.2 Hz, 1H, Ar—H), 6.96 and 6.94 (t, $^3J_{HH}$=7.2 Hz, 1H, Ar—H), 4.65-4.56 and 3.66 (dd, $^3J_{HH}$=10.4 Hz, 6.3 Hz, 1H, CH), 4.35-4.13 (m, 1H, CH), 3.06-2.91 (m, 1H, CH$_2$), 2.78-2.64 (m, 1H, CH$_2$), 1.54-1.43 (m, 3H, CH$_3$); HRMS (ESI) calcd for C$_{20}$H$_{19}$N$_4$OCl$_2$[M+H]$^+$ 401.0931. found 401.0929.

(1S, 3S)—N'-(3,4-dichlorobenzylidene)-1-methyl-2,3,4,9-tetrahydropyridino [3,4-b] indol-3-formylhydrazine (I$_c$-7)

Yellow solid, yield 79%, melting point 189-193° C.;
$^1$H NMR (400 MHz, DMSO-d$_6$) δ 11.84 and 11.67 (s, 1H, NH), 10.98 and 10.86 (s, 1H, O═C—NH), 8.34 and 8.07 (s, 1H, N═CH), 7.94 and 7.88 (s, 1H, Ph-H), 7.72 and 7.64 (s, 2H, Ph-H), 7.41 and 7.39 (d, $^3J_{HH}$=8.4 Hz, 1H, Ar—H), 7.33 and 7.31 (d, $^3J_{HH}$=8.4 Hz, 1H, Ar—H), 7.06 and 7.04 (t, $^3J_{HH}$=7.2 Hz, 1H, Ar—H), 6.96 and 6.96 (t, $^3J_{HH}$=7.2 Hz, 1H, Ar—H), 4.68 and 3.70 (dd, $^3J_{HH}$=10.4 Hz, 4.4 Hz, 1H, CH), 4.38 and 4.19 (q, $^3J_{HH}$=6.4 Hz, 1H, CH), 3.06 and 2.98 (dd, $^3J_{HH}$=6.6 Hz, $^3J_{HH}$=14.4 Hz, 1H, CH$_2$), 2.80-2.66 (m, 1H, CH$_2$), 1.53 and 1.48 (d, $^3J_{HH}$=6.4 Hz, 3H, CH$_3$); HRMS (ESI) calcd for C$_{20}$H$_{19}$N$_4$OCl$_3$[M+H]$^+$ 401.0931. found 401.0934.

(1S, 3S)—N'-(4-methoxybenzylidene)-1-methyl-2,3,4,9-tetrahydropyridino [3,4-b] indol-3-formylhydrazine (I$_c$-8)

Yellow solid, yield 69%, melting point 138-143° C.;
$^1$H NMR (400 MHz, DMSO-d$_6$) δ 11.35 and 11.22 (s, 1H, NH), 10.84 and 10.81 (s, 1H, O=C—NH), 8.27 and 8.00 (s, 1H, N=CH), 7.65 and 7.55 (d, $^3J_{HH}$=8.0 Hz, 2H, Ph-H), 7.40 and 7.36 (d, $^3J_{HH}$=7.6 Hz, 1H, Ar—H), 7.30 (d, $^3J_{HH}$=7.6 Hz, 1H, Ar—H), 7.08-6.89 (m, 4H, Ar—H and Ph-H), 4.45 and 3.59 (d, $^3J_{HH}$=8.8 Hz, 1H, CH), 4.20-4.08 (m, 1H, CH), 3.81 and 3.74 (s, 3H, O=CH$_2$), 2.93 (d, $^2J_{HH}$=14.4 Hz, 1H, CH$_2$), 2.76-2.56 (m, 1H, CH$_3$), 1.45 (d, $^5J_{HH}$=6.0 Hz, 3H, CH$_3$), HRMS (ESI) calcd for C$_{21}$H$_{23}$N$_4$O$_2$[M+H]$^+$ 363.1816. found 363.1819.

(1S, 3S)—N'-(3-methoxybenzylidene)-1-methyl-2,3,4,9-tetrahydropyridino [3,4-b] indol-3-formylhydrazine (I$_c$-9)

Yellow solid, yield 63%, melting point 186-190° C.;
$^1$H NMR (400 MHz, DMSO-d$_6$) δ 11.54 and 11.39 (s, 1H, NH), 10.87 and 10.83 (s, 1H, O=C—NH), 8.32 and 8.03 (s, 1H, N=CH), 7.45-7.11 (m, 5H, Ph-H and Ar—H), 7.08-8.89 (m, 3H, Ar—H and Ph-H), 4.48 and 3.63 (d, $^3J_{HH}$=8.0 Hz, 1H, CH), 4.25-4.10 (m, 1H, CH), 3.81 and 3.69 (s, 3H, O—CH$_3$), 3.02-2.89 (m, 1H, CH$_2$), 2.77-2.60 (m, 1H, CH$_2$), 1.46 (d, $^3J_{HH}$=5.2 Hz, 3H, CH$_3$); HRMS (ESI) calcd for C$_{23}$H$_{23}$N$_3$O$_2$[M+H]$^+$ 363.1816. found 363.1818.

(1S, 3S)—N'-(2-methoxybenzylidene)-1-methyl-2,3,4,9-tetrahydropyridino [3,4-b] indol-3-formylhydrazine (I$_c$-10)

Yellow solid, yield 82%, melting point 180-183° C.;
$^1$H NMR (400 MHz, DMSO-d$_6$) δ 11.52 and 11.46 (s, 1H, NH), 10.90 and 10.84 (s, 1H, O=C—NH), 8.66 and 8.41 (s, 1H, N=CH), 7.84 and 7.68 (d, $^3J_{HH}$=7.2 Hz, 1H, Ph-H), 7.41 (d, $^3J_{HH}$=7.6 Hz, 1H, Ar—H), 7.37 (d, $^3J_{HH}$=7.6 Hz, 1H, Ar—H), 7.31 (dd, $^3J_{HH}$=8.0 Hz, 1H, Ph-H), 7.14-6.86 (m, 4H, Ph-H and Ar—H), 4.54 and 3.61 (dd, $^3J_{HH}$=10.0 Hz, 2.8 Hz, 1H, CH), 4.30-4.10 (m, 1H, CH), 3.86 and 3.84 (s, 3H, O—CH$_3$), 3.04-3.89 (m, 1H, CH$_2$), 2.77-2.60 (m, 1H, CH$_2$), 1.55-1.37 (m, 3H, CH$_3$); HRMS (ESI) calcd for C$_{21}$H$_{23}$N$_6$O$_2$[M+H]$^+$ 363.1816. found 363.1823.

(1S, 3S)—N'-(3,4-dimethoxybenzylidene)-1-methyl-2,3,4,9-tetrahydropyridino [3,4-b] indol-3-formylhydrazine (I$_c$-11)

Light yellow solid, yield 91%, melting point 203-206° C.;
$^1$H NMR (400 MHz, DMSO-d$_6$) δ 11.47 and 11.27 (s, 1H, NH), 10.89 and 10.83 (s, 1H, O=C—NH), 8.25 and 7.99 (s, 1H, N=CH), 7.43-7.36 (m, 1H, Ar—H), 7.34-7.27 and 7.22-7.15 (m, 3H, Ar—H and Ph-H), 7.07-6.91 (m, 3H, Ar—H and Ph-H), 4.49 and 3.67-3.59 (dd, $^3J_{HH}$=11.2 Hz, 3.6 Hz, CH), 4.33-4.11 (m, 1H, CH), 3.82 and 3.75 (s, 3H, O—CH$_3$), 3.81 and 3.64 (s, 3H, O—CH$_3$), 3.03 and 2.94 (dd, $^3J_{HH}$=2.8 Hz, $^3J_{HH}$=14.8 Hz, 1H, CH$_2$), 2.76-2.65 (m, 1H, CH$_2$) 1.48 and 1.46 (d, $^3J_{HH}$=6.8 Hz, 3H, CH$_3$); HRMS (ESI) calcd for C$_{22}$H$_{23}$N$_4$O$_4$[M+H]$^+$ 393.1921. found 393.1918.

(1S, 3S)—N'-((benzo [d] [1,3] dioxymethylene-5)-methylene-1-methyl-2,3,4,9-tetrahydropyridino [3,4-b] indol-3-formylhydrazine (I$_c$-12)

Yellow solid, yield 83%, melting point 199-203° C.;
$^1$H NMR (400 MHz, DMSO-d$_6$) δ 11.41 and 11.26 (s, 1H, NH), 10.86 and 10.81 (s, 1H, O=C—NH), 8.24 and 7.96 (s, 1H, N=CH), 7.40 and 7.36 (d, $^3J_{HH}$=7.6 Hz, 1H, Ar—H), 7.31 and 7.30 (d, $^3J_{HH}$=8.0 Hz, 1H, Ar—H), 7.28 and 7.17 (s, 1H, Ph-H), 7.15 and 7.09 (d, $^3J_{HH}$=8.0 Hz, 1H, Ph-H), 7.06-6.96 (m, 2H, Ar—H and Ph-H), 6.94 (t, $^3J_{HH}$=7.6 Hz, 1H, Ar—H), 6.10 (s, 1H, O—CH$_2$), 6.02 (d, $^2J_{HH}$=4.8 Hz, 1H, O—CH$_2$), 4.49 and 3.60 (dd, $^3J_{HH}$=10.8 Hz, 3.6 Hz, CH), 4.22 and 4.13 (m, 1H, CH), 2.99-2.87 (m, 1H, CH$_2$), 2.75-2.87 (m, 1H, CH$_2$), 1.45 (d, $^3J_{HH}$=6.4 Hz, 3H, CH$_3$); HRMS (ESI) calcd for C$_{21}$H$_{23}$N$_4$O$_3$[M+H]$^+$ 377.1608. found 377.1615.

(1S, 3S)—N'-(2, 3-dihydrobenzo [b] [1,4] dioxin-6-methylene)-1-methyl)-2,3,4,9-tetrahydropyridino [3,4-b] indol-3-formylhydrazine (I$_c$-13)

Light yellow solid, yield 81%, melting point 204-207° C.;
$^1$H NMR (400 MHz, DMSO-d$_6$) δ 11.44 and 11.26 (s, 1H, NH), 10.89 and 10.82 (s, 1H, O=C—NH), 8.21 and 7.94 (s, 1H, c=CH), 7.40 and 7.36 (d, $^3J_{HH}$=7.6 Hz, 1H, Ar—H), 7.32 and 7.30 (d, $^3J_{HH}$=8.0 Hz, 1H, Ar—H), 7.20 and 7.10 (s, 1H, Ph-H), 7.19 and 7.09 (d, $^3J_{HH}$=7.6 Hz, 1H, Ph-H), 7.07-7.01 (m, 1H, Ar—H), 6.99-6.83 (m, 2H, Ar—H and Ph-H), 4.51 and 3.61 (dd, $^3J_{HH}$=10.8 Hz, 3.6 Hz, 1H, CH), 4.35-4.09 (m, 5H, CH and O—CH$_2$—CH$_2$—O), 3.03-2.89 (m, 1H, CH$_2$), 2.76-2.60 (m, 1H, CH$_2$), 1.53-1.43 (m, 3H, CH$_3$), HRMS (ESI) calcd for C$_{22}$H$_{23}$N$_4$O$_2$[M+H]$^+$ 391.1765. found 391.1763.

(1S, 3S)—N'-(6-hydroxynaphthalene-2-methylene)-1-methyl-2,3,4,9-tetrahydropyridino [3,4-b] indol-3-formylhydrazine (I$_c$-14)

Yellow solid, yield 70%, melting point 275-278° C.;
$^1$H NMR (400 MHz, DMSO-d$_6$) δ 11.46 and 11.35 (s, 1H, NH), 10.85 and 10.81 (s, 1H, O=C—NH), 9.98 (s, 1H, OH), 8.42 and 8.16 (s, 1H, N=CH), 7.99 and 7.91 (s, 1H, Naphthalene-H), 7.85 (d, $^3J_{HH}$=9.2 Hz, 1H, Nahphthalene-H), 7.80 and 7.61 (d, $^3J_{HH}$=8.8 Hz, 1H, Naphthalene-H), 7.74 and 7.70 (d, $^3J_{HH}$=8.8 Hz, 1H, Naphthalene-H), 7.42 and 7.37 (d, $^3J_{HH}$=7.6 Hz, 1H, Ar—H), 7.16 and 7.08 (s, 1H, Naphthalene-H), 7.15-7.09 (m, 1H, Naphthalene-H), 7.04 (t, $^3J_{HH}$=7.6 Hz, 1H, Ar—H), 7.00-6.90 (m, 1H, Ar—H), 4.52 and 3.63 (d, $^3J_{HH}$=8.4 Hz, 1H, CH), 4.25-4.10 (m, 1H, CH), 3.02-2.90 (m, 1H, CH$_2$), 2.73 and 2.65 (t, $^3J_{HH}$=12.8 Hz, 1H, CH$_2$), 1.47 (d, $^3J_{HH}$=6.0 Hz, 3H, CH$_3$); HRMS (ESI) calcd for C$_{24}$H$_{23}$N$_4$O$_2$[M+H]$^+$ 399.1816. found 399.1822.

(1S, 3S)—N'-(pyridine-4-methylene)-1-methyl-2,3,4,9-tetrahydropyridino [3,4-b] indol-3-formylhydrazine (I$_c$-15)

Yellow solid, yield 79%, melting point 235-239° C.;
$^1$H NMR (400 MHz, DMSO-d$_6$) δ 11.84 and 11.69 (s, 1H, NH), 10.90 and 10.84 (s, 1H, O=C—NH), 8.65 and 8.57 (d, $^3J_{HH}$=5.6 Hz, 2H, Py-H), 8.35 and 8.05 (s, 1H, N=CH), 7.65 and 7.57 (d, $^3J_{HH}$=5.6 Hz, 2H, Py-H), 7.41 and 7.37 (d, ³J$_{HH}$=7.6 Hz, 1H, Ph-H), 7.34-7.29 (m, 1H, Ar—H), 7.04 (t, ³J$_{HH}$=7.6 Hz, 1H, Ar—H), 6.95 (t, ³J$_{HH}$=7.6 Hz, 1H, Ar—H), 4.58 and 3.67 (dd, ³J$_{HH}$=10.8 Hz, 3.6 Hz, 1H, CH), 4.26 and 4.16 (q, ³J$_{HH}$=6.4 Hz, 1H, CH), 3.05-2.91 (m, 1H, CH$_2$), 2.80-2.62 (m, 1H, CH$_2$), 1.48 (d, ³J$_{HH}$=6.4 Hz, 3H, CH$_3$); HRMS (ESI) calcd for C$_{25}$H$_{20}$N$_5$O[M+H]$^+$ 334.1662. found 334.1663.

(1S, 3S)—N'-(pyridine-3-methylene)-1-methyl-2,3,4,9-tetrahydropyridino [3,4-b] indol-3-formylhydrazine (I$_c$-16)

Yellow solid, yield 72%, melting point 205-209° C.;
$^1$H NMR (400 MHz, DMSO-d$_6$) δ 11.74 and 11.58 (s, 1H, NH), 10.91 and 10.84 (s, 1H, O=C—NH), 8.84 and 8.79 (s, 1H, Py-H), 8.62 and 8.55 (d, ³J$_{HH}$=4.0 Hz, 1H, Py-H), 8.41 and 8.12 (s, 1H, N=CH), 8.12 and 8.03 (d, ³J$_{HH}$=4.0 Hz, 1H, Py-H), 7.49 and 7.44-7.35 (m, 2H, Py-H and Ar—H), 7.33 and 7.31 (d, ³J$_{HH}$=7.6 Hz, 1H, Ph-H), 7.04 (t, ³J$_{HH}$=7.6 Hz, 1H, Ar—H), 6.96 (t, ³J$_{HH}$=7.6 Hz, 1H, Ar—H), 4.59 and 3.66 (dd, ³J$_{HH}$=10.8 Hz, 3.6 Hz, 1H, CH), 4.32 and 4.12 (m, 1H, CH), 3.85-2.92 (m, 1H, CH$_3$), 2.78-2.63 (m, 1H, CH$_3$), 1.53-1.39 (m, 3H, CH$_3$); HRMS (ESI) calcd for C$_{29}$H$_{28}$N$_9$O [M+H]$^+$ 334.1662. found 334.1664.

(1S, 3S)—N'-(pyridine-2-methylene)-1-methyl-2,3,4,9-tetrahydropyridino [3,4-b] indol-3-formylhydrazine (I$_c$-17)

Yellow solid, yield 72%, melting point 245-249° C.;
$^1$H NMR (400 MHz, DMSO-d$_6$) δ 11.69 and 11.65 (s, 1H, NH), 10.85 and 10.82 (s, 1H, O=C—NH), 8.62 and 8.57 (d, ³J$_{HH}$=4.8 Hz, 1H, Py-H), 8.36 and 8.10 (s, 1H, N=CH), 7.95 and 7.80 (d, ³J$_{HH}$=8.0 Hz, 1H, Py-H), 7.88 and 7.75 (td, ³J$_{HH}$=1.2 Hz, ³J$_{HH}$=7.6 Hz, 1H, Py-H), 7.44-7.33 (m, 2H, Py-H and Ar—H), 7.31 and 7.30 (d, ³J$_{HH}$=7.6 Hz, 1H, Ar—H), 7.03 (t, ³J$_{HH}$=7.2 Hz, 1H, Ar—H), 6.95 and 6.92 (t, ³J$_{HH}$=7.2 Hz, 1H, Ar—H), 4.50 and 3.63 (dd, ³J$_{HH}$=10.8 Hz, 4.0 Hz, CH), 4.16 (q, ³J$_{HH}$=8.9 Hz, 1H, CH), 2.94 (ddd, ³J$_{HH}$=1.6 Hz, ³J$_{HH}$=4.4 Hz, ²J$_{HH}$=14.8 Hz, 1H, CH$_2$), 2.72 and 2.63 (ddd, ⁴J$_{HH}$=2.0 Hz, ⁴J$_{HH}$=10.8 Hz, ²J$_{HH}$=14.8 Hz, 1H, CH$_2$), 1.46 and 1.45 (d, ³J$_{HH}$=6.8 Hz, 3H, CH$_3$); HRMS (ESI) calcd for C$_{19}$H$_{20}$N$_2$O[M+H]$^+$ 334.1662. found 334.1666.

(1S, 3S)—N'-(furan-2-methylene)-1-methyl-2,3,4,9-tetrahydropyridino [3,4-b] indol-3-formylhydrazine (I$_c$-18)

Yellow solid, yield 62%, melting point 144-148° C.;
$^1$H NMR (400 MHz, CDCl$_3$) δ 10.33 and 10.20 (s, 1H, NH), 8.26 and 8.11 (s, 1H, O=C—NH), 8.04 and 7.72 (s, 1H, N=CH), 7.51-7.38 (m, 2H, Ar—H and furan-H), 7.34 and 7.31 (d, ³J$_{HH}$=7.6 Hz, 1H, Ar—H), 7.14 (t, ³J$_{HH}$=6.8 Hz, 1H, Ar—H), 7.08 (t, ³J$_{HH}$=7.2 Hz, 1H, Ar—H), 6.77 and 6.62 (s, 1H, furan-H), 6.45 and 6.42 (s, 1H, furan-H), 4.65 and 3.69 (d, ³J$_{HH}$=7.6 Hz, 1H, CH), 4.32-4.11 (m, 1H, CH), 3.30 and 3.19 (d, ³J$_{HH}$=13.6 Hz, 1H, CH$_2$), 2.79 (t, ³J$_{HH}$=13.2 Hz, 1H, CH$_2$), 1.97 (br, 1H, NH), 1.52 and 1.46 (d, ³J$_{HH}$=6.4 Hz, 3H, CH$_3$); HRMS (ESI) calcd for C$_{18}$H$_{19}$N$_4$O$_2$[M+H]$^+$ 323.1503. found 323.1505.

(1S, 3S)—N'-(pyrrole-2-methylene)-1-methyl-2,3,4,9-tetrahydropyridino [3,4-b] indol-3-formylhydrazine Red solid, yield 75%, melting point 207-209° C.;
$^1$H NMR (400 MHz, DMSO-d$_6$) δ 11.52 and 11.31 (s, 1H, NH), 11.16 and 11.05 (s, 1H, Pyrrole-NH), 10.83 and 10.80 (s, 1H, O=C—NH), 8.15 and 7.88 (s, 1H, N=CH), 7.45-7.35 (m, 1H, Ar—H), 7.30 (d, ³J$_{HH}$=7.2 Hz, 1H, Ar—H), 7.03 (t, ³J$_{HH}$=7.2 Hz, 1H, Ar—H), 6.95 (t, ³J$_{HH}$=7.2 Hz, 1H, Ar—H), 6.90 and 6.83 (s, 1H, Pyrrole-H), 6.45 and 6.39 (s, 1H, Pyrrole-H), 6.13 and 6.08 (s, 1H, Pyrrole-H), 4.60 and 3.58 (d, ³J$_{HH}$=8.8 Hz, 1H, CH), 4.24-4.08 (m, 1H, CH), 2.98-2.88 (m, 1H, CH$_2$), 2.70-2.59 (m, 1H, CH$_2$), 1.50-1.45 (m, 3H, CH$_3$); HRMS (ESI) calcd for C$_{18}$H$_{20}$N$_4$O[M+H]$^+$ 322.1662. found 322.1668.

(1S, 3S)—N'-(thiophene-2-methylene)-1-methyl-2,3,4,9-tetrahydropyridino [3,4-b] indol-3-formylhydrazine Yellow solid, yield 76%, melting point 139-141° C.;
$^1$H NMR (400 MHz, DMSO-d$_6$) δ 11.55 and 11.39 (s, 1H, NH), 10.90 and 10.83 (s, 1H, O=C—NH), 8.56 and 8.24 (s, 1H, N=CH), 7.67 and 7.54 (d, ³J$_{HH}$=4.8 Hz, 1H, Thiophene-H), 7.47-7.35 (m, 2H, Thiophene-H and Ar—H), 7.35-7.28 (m, 1H, Ar—H), 7.14 and 7.09 (t, ³J$_{HH}$=4.4 Hz, 1H, Thiophene-H), 7.04 (t, ³J$_{HH}$=7.2 Hz, 1H, Ar—H), 7.00-6.90 (m, 1H, Ar—H), 4.38 and 3.62 (dd, ³J$_{HH}$=8.8 Hz, 4.0 Hz, 1H, CH), 4.29-4.10 (m, 1H, CH), 3.04-2.89 (m, 1H, CH$_2$), 2.77-2.61 (m, 1H, CH$_2$), 1.54-1.38 (m, 3H, CH$_3$); HRMS (ESI) calcd for C$_{18}$H$_{19}$N$_1$OS [M+H]$^+$ 339.1274. found 339.1278.

(1S, 3S)—N'-(imidazole-2-methylene)-1-methyl-2,3,4,9-tetrahydropyridino [3,4-b] indol-3-formylhydrazine Green solid, yield 81%, melting point 188-190° C.;
$^1$H NMR (400 MHz, DMSO-d$_6$) δ 14.10, 13.33, 12.81 and 12.57 (s, 1H, Imidazole-NH), 12.93 and 11.47 (s, 1H, NH), 10.84 and 10.81 (s, 1H, O=C—NH), 8.45, 8.26, 7.95 and 7.44 (s, 1H, N=CH), 7.42-6.88 (m, 6H, Ar—H and Imidazole-H), 4.65, 4.50, 3.69 and 3.63 (m, 1H, CH), 4.37 and 4.17 (m, 1H, CH), 3.03 and 2.95 (d, ³J$_{HH}$=14.0 Hz, 1H, CH$_2$), 2.78-2.56 (m 1H, CH$_3$), 1.52-1.42 (m, 3H, CH$_3$); HRMS (ESI) calcd for C$_{37}$H$_{19}$N$_6$O[M+H]$^+$ 323.1615. found 323.1620.

(1S, 3S)—N'-((E)-but-2-enylidene)-1-methyl-2,3,4,9-tetrahydropyridino [3,4-b] indol-3-formylhydrazine (I$_c$-22)

Yellow solid, yield 61%, melting point 145-148° C.;
$^1$H NMR (400 MHz, CDCl$_3$) δ 10.10 and 9.63 (s, 1H, NH), 8.23 and 8.15 (s, 1H, O=C—NH), 7.72 and 7.37 (d, ³J$_{HH}$=8.4 Hz, 1H, N=CH), 4.57-4.48 and 3.70-3.58 (m, 1H, CH), 4.31-4.06 (m, 1H, CH), 3.27 and 3.12 (d, ³J$_{HH}$=14.4 Hz, 1H, CH$_2$), 2.85-2.66 (m, 1H, CH$_2$), 2.09 (br, 1H, NH), 1.92-1.75 (m, 3H, CH$_3$), 1.50 and 1.43 (d, ³J$_{HH}$=5.6 Hz, 3H, CH$_3$); HRMS (ESI) calcd for C$_{18}$H$_{20}$N$_5$O[M+H]$^+$ 297.1710. found 297.1714.

(1S, 3S)—N'-butylidene-1-methyl-2,3,4,9-tetrahydropyridino [3,4-b] indol-3-formylhydrazine (I$_c$-23)

Yellow solid 0.52 g, yield 71%, melting point 113-117° C.;
$^1$H NMR (400 MHz, DMSO-d$_6$) δ 11.04 and 10.97 (s, 1H, NH), 10.82 and 10.80 (s, 1H, O=C—NH), 7.59 and 7.42-7.33 (m, 3H, N=CH and Ar—H), 7.30 (d, ³J$_{HH}$=7.6 Hz, 1H, Ph-H), 7.03 (t, ³J$_{HH}$=6.8 Hz, 1H, Ar—H), 6.95 (t, ³J$_{HH}$=6.8

Hz, 1H, Ar—H), 4.28 and 3.51 (d, $^3J_{HH}$=9.6 Hz, 1H, CH), 4.19-4.04 (m, 1H, CH), 2.89 (d, $^3J_{HH}$=14.0 Hz, 1H, CH$_2$), 2.67 and 2.57 (t, $^2J_{HH}$=12.8 Hz, 1H, CH$_2$), 2.25-2.10 (m, 2H, CH$_2$), 1.55-1.40 (m, 3H, CH$_3$ and CH$_2$), 0.92 and 0.86 (t, $^3J_{HH}$=6.8 Hz, 3H, CH$_3$); HRMS (ESI) calcd for C$_{17}$H$_{23}$N$_4$O [M+H]$^+$ 299.1866. found 299.1870.

(1S, 3S)—N'-octadien-1-methyl-2,3,4,9-tetrahydropyridino [3,4-b] indol-3-formylhydrazine (I$_c$-24)

Yellow solid, yield 78%, melting point 68-71° C.;
$^1$H NMR (400 MHz, CDCl$_3$) δ 9.94 and 9.02 (s, 1H, NH), 7.90 and 7.50 (s, 1H, N═CH), 7.50 and 7.46 (d, $^3J_{HH}$=8.0 Hz, 1H, Ar—H), 7.34 and 7.32 (d, $^3J_{HH}$=8.4 Hz, 1H, Ar—H), 7.17 (t, $^3J_{HH}$=7.2 Hz, 1H, Ar—H), 7.11 (t, $^3J_{HH}$=7.2 Hz, 1H, Ar—H), 4.53 and 3.76 (dd, $^3J_{HH}$=11.2 Hz, 4.4 Hz, 1H, CH), 4.33-4.17 (m, 1H, CH), 3.37 and 3.13 (dd, $^3J_{HH}$=2.8 Hz, $^3J_{HH}$=14.4 Hz, 1H, CH$_2$), 2.83-2.72 (m, 1H, CH$_2$), 2.38 and 2.22 (q, $^3J_{HH}$=7.2 Hz, 2H, CH$_2$), 1.96 (br, 1H, NH), 1.58-1.43 (m, 3H, CH$_3$ and CH$_3$), 1.42-1.18 (m, 9H, CH$_2$), 0.95-0.81 (m, 3H, CH$_3$); HRMS (ESI) calcd for C$_{21}$H$_{35}$N$_4$O[M+H]$^+$ 355.2493. found 355.2492.

(1S, 3S)—N'-(cyclohexylmethylene)-1-methyl-2,3,4,9-tetrahydropyridino [3,4-b] indol-3-formylhydrazine (I$_c$-25)

Yellow solid, yield 92%, melting point 123-126° C.;
$^1$H NMR (400 MHz, CDCl$_3$) δ 9.88 and 9.21 (s, 1H, NH), 7.98 and 7.96 (s, 1H, N═CH), 7.49 and 7.47 (d, $^3J_{HH}$=8.0 Hz, 1H, Ar—H), 7.38-7.29 and 7.05 (m, 2H, Ar—H and O═C—NH), 7.16 and 7.16 (t, $^3J_{HH}$=7.2 Hz, 1H, Ar—H), 7.10 (t, $^3J_{HH}$=7.2 Hz, 1H, Ar—H), 4.52 and 3.66 (dd, $^2J_{HH}$=10.8 Hz, 4.4 Hz, 1H, CH), 4.28 and 4.18 (q, $^3J_{HH}$=6.8 Hz, 1H, CH), 3.35 and 3.12 (dd, $^3J_{HH}$=2.8 Hz, $^3J_{HH}$=15.6 Hz, 1H, CH$_2$), 2.85-2.72 (m, 1H, CH$_2$), 2.47-2.35 and 2.23-2.13 (m, 1H, CH), 1.94 (br, 1H, NH), 1.87-1.58 (m, 4H, CH$_3$), 1.53 and 1.48 (d, $^3J_{HH}$=10.8 Hz, 3H, CH$_3$), 1.38-1.11 (m, 6H, CH$_2$), 0.95-0.81 (m, 3H, CH$_3$); HRMS (ESI) calcd for C$_{20}$H$_{27}$N$_4$O[M+H]$^+$ 339.2180. found 339.2179.

(1S, 3S)—N'-(2, 2-dimethylpropylidene)-1-methyl-2,3,4,9-tetrahydropyridino [3,4-b] indol-3-formylhydrazine (I$_c$-26)

Yellow solid, yield 95%, melting point 140-141° C.;
$^1$H NMR (400 MHz, CDCl$_3$) δ 9.93 and 9.39 (s, 1H, NH), 8.13 and 8.09 (s, 1H, N═CH), 7.53-7.02 (m, 4H, Ar—H), 4.51 and 3.67 (d, $^3J_{HH}$=8.4 Hz, 1H, CH), 4.37-4.16 (m, 1H, CH), 3.33 and 3.13 (d, $^3J_{HH}$=14.4 Hz, 1H, CH$_2$), 2.79 (t, $^2J_{HH}$=13.2 Hz, 1H, CH$_2$), 2.09 (br, 1H, NH), 1.58-1.41 (m, 3H, CH$_3$), 1.15 and 1.66 (s, 9H, CH$_3$); HRMS (ESI) calcd for C$_{18}$H$_{25}$N$_4$O[M+H]$^+$ 313.2023. found 313.2028.

(1S, 3S)—N'-(1-phenylethylidene)-1-methyl-2,3,4,9-tetrahydropyridino [3,4-b] indol-3-formylhydrazine (I$_c$-27)

Light yellow solid, yield 56%, melting point 221-224° C.;
$^1$H NMR (400 MHz, DMSO-d$_6$) δ 10.84 and 10.81 (s, 1H, N—H), 10.69 and 10.48 (s, 1H, O═C—NH), 7.89-7.77 and 7.76-7.67 (m, 2H, Ar—H), 7.48-7.27 (m, 5H, Ph-H and Ar—H), 7.08-6.88 (m, 2H, Ar—H), 4.53 and 3.78 (dd, $^3J_{HH}$=10.8 Hz, 3.6 Hz, 1H, CH), 4.23-4.11 (m, 1H, CH), 3.03-2.93 (m, 1H, CH$_2$), 2.76-2.59 (m, 1H, CH$_2$), 3.31 and 3.30 (s, 3H, CH$_3$), 1.46 (d, $^3J_{HH}$=6.4 Hz, 3H, CH$_3$); HRMS (ESI) calcd for C$_{23}$H$_{22}$N$_4$O[M+H]$^+$ 347.1867. found 347.1872.

(1S, 3S)—N'-(3, 3-dimethyl-2-butylidene)-1-methyl-2,3,4,9-tetrahydropyridino [3,4-b] indol-3-formylhydrazine (I$_c$-28)

Yellow solid, yield 63%, melting point 103-107° C.;
$^1$H NMR (400 MHz, DMSO-d$_6$) δ 10.80 and 10.79 (s, 1H, N—H), 10.18 and 10.02 (s, 1H, O═C—NH), 7.40 and 7.35 (d, $^3J_{HH}$=7.6 Hz, 1H, Ar—H), 7.29 (d, $^3J_{HH}$=8.0 Hz, 1H, Ar—H), 7.03 (t, $^3J_{HH}$=7.2 Hz, 1H, Ar—H), 6.95 and 6.93 (t, $^3J_{HH}$=6.8 Hz, 1H, Ar—H), 4.26 and 3.65 (dd, $^3J_{HH}$=10.8 Hz, 4.0 Hz, 1H, CH), 4.16-4.07 (m, 1H, CH), 2.94 (dd, $^3J_{HH}$=2.8 Hz, $^3J_{HH}$=14.8 Hz, 1H, CH$_2$), 2.70-2.53 (m, 1H, CH$_2$), 1.87 and 1.85 (s, 3H, CH$_3$), 1.43 (d, $^3J_{HH}$=6.4 Hz, 3H, CH$_3$), 1.12 and 1.04 (s, 9H, CH$_3$); HRMS (ESI) calcd for C$_{26}$H$_{23}$N$_2$O [M+H]$^+$ 327.2180. found 327.2186.

(1S, 3S)—N'-cyclohexylidene-1-methyl-2,3,4,9-tetrahydropyridino [3,4-b] indol-3-formylhydrazine (I$_c$-29)

Yellow solid, yield 60%, melting point 131-135° C.;
$^1$H NMR (400 MHz, DMSO-d$_6$) δ 10.81 and 10.78 (s, 1H, NH), 10.39 and 10.24 (s, 1H, O═C—NH), 7.39 and 7.36 (d, $^3J_{HH}$=8.0 Hz, 1H, Ar—H), 7.29 (d, $^3J_{HH}$=7.6 Hz, 1H, Ar—H), 7.02 (t, $^3J_{HH}$=7.2 Hz, 1H, Ar—H), 6.94 (t, $^3J_{HH}$=7.2 Hz, 1H, Ar—H), 4.36 and 3.62 (dd, $^3J_{HH}$=10.0 Hz, 3.6 Hz, 1H, CH), 4.18-4.04 (m, 1H, CH), 2.94-2.84 (m, 1H, CH$_2$), 2.69-2.58 (m, 1H, CH$_2$), 2.40-2.12 (m, 4H, CH$_2$), 1.71-1.51 (m, 6H, CH$_2$), 1.42 (d, $^3J_{HH}$=6.0 Hz, 3H, CH$_3$); HRMS (ESI) calcd for C$_{19}$H$_{25}$N$_4$O[M+H]$^+$ 325.2023. found 325.2023.

Embodiment 20: N'-((1S, 3S)-1-methyl-2,3,4,9-tetrahydropyridino [3,4-b] indol-3-tricarboxylate) benzo [d] [1, 2, 3] thiadiazole-7-formylhydrazine (I$_d$-1)

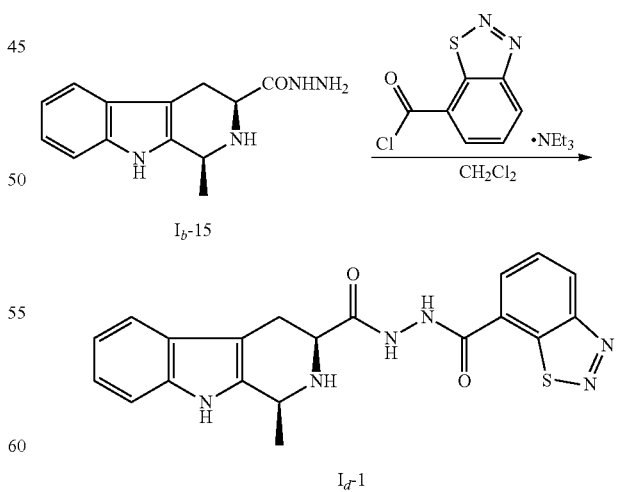

Add 0.40 g (1.64 mmol) of hydrazide and 40 mL of tetrahydrofuran to a 100 mL single-necked flask, add 0.22 g (2.17 mmol) of NEt$_3$, add a tetrahydrofuran solution containing acyl chloride (1.64 mmol), stir them at room temperature overnight after dropwise addition and remove the solvent to obtain 0.48 g of green solid. The yield is 72% and the melting point is 180-183° C.; $^1$H NMR (400 MHz, DMSO-d$_6$) δ 11.22 (br, 1H, O=C—NH), 10.91 (s, 1H, NH), 10.37 (br, 1H, O=C..NH), 9.00 (d, $^3J_{HH}$=8.0 Hz, 1H, Ph-H), 8.62 (d, $^3J_{HH}$=7.2 Hz, 1H, Ph-H), 7.99 (t, $^3J_{HH}$=7.6 Hz, 1H, Ph-H), 7.44 (d, $^3J_{HH}$=7.6 Hz, 1H, Ar—H), 7.33 (d, $^3J_{HH}$=8.0 Hz, 1H, Ar—H), 7.06 (t, $^3J_{HH}$=7.2 Hz, 1H, Ar—H), 6.99 (t, $^3J_{HH}$=7.2 Hz, 1H, Ar—H), 4.40-4.20 (m, 1H, CH), 3.97-3.76 (m, 1H, CH), 3.11-2.99 (m, 1H, CH$_2$), 2.85-2.73 (m, 1H, CH$_2$), 1.50 (d, $^3J_{HH}$=6.0 Hz, 3H, CH$_3$); HRMS (ESI) calcd for C$_{20}$H$_{33}$N$_6$O$_2$S[M+H]$^+$ 407.1285. found 407.1281.

Compounds I$_d$-2-I$_d$-7 are completed through repeating the foregoing steps 4-methyl-N'-((1S, 3S)-1-methyl-2,3,4,9-tetrahydro-pyridino [3,4-b] indol-3-triformyl)-1,2,3-thiadiaz-ole-5-formylhydrazine (I$_d$-2)

Green solid, yield 56%, melting point 145-148° C.;
$^1$H NMR (400 MHz, DMSO-d$_6$) δ 10.85 (s, 1H, NH), 10.29 (br, 1H, O=C—NH), 7.40 (d, $^3J_{HH}$=7.2 Hz, 1H, Ar—H), 7.31 (d, $^3J_{HH}$=7.6 Hz, 1H, Ar—H), 7.04 (t, $^3J_{HH}$=6.8 Hz, 1H, Ar—H), 6.97 (t, $^3J_{HH}$=6.8 Hz, 1H, Ar—H), 4.25-4.11 (m, 1H, CH), 3.78-3.62 (m, 1H, CH), 3.03-2.92 (m, 1H, CH$_2$), 2.85 (s, 3H, CH$_3$), 2.78-2.64 (m, 1H, CH$_2$), 1.46 (d, $^3J_{HH}$=5.2 Hz, 3H, CH$_3$); HRMS (ESI) calcd for C$_{13}$H$_{15}$N$_6$O$_2$S[M+H]$^+$ 371.1285. found 371.1287.

(1S, 3S)—N'-isonicotinoyl-1-methyl-2,3,4,9-tetrahy-dropyridino [3,4-b] indol-3-formylhydrazine (I$_d$-3)

Brown solid, yield 23%, melting point 243-245° C.;
$^1$H NMR (400 MHz, DMSO-d$_6$) δ 10.81 (s, 2H, NH and O=C—NH), 10.14 (br, 1H, O=C—NH), 8.78 (d, $^3J_{HH}$=4.0 Hz, 2H, Py-H), 7.81 (d, $^3J_{HH}$=4.0 Hz, 2H, Py-H), 7.39 (d, $^3J_{HH}$=7.2 Hz, 1H, Ar—H), 7.30 (d, $^3J_{HH}$=7.6 Hz, 1H, Ar—H), 7.04 (t, $^3J_{HH}$=7.2 Hz, 1H, Ar—H), 6.96 (t, $^3J_{HH}$=7.2 Hz, 1H, Ar—H), 4.18-4.08 (m, 1H, CH), 3.68-3.59 (m, 1H, CH), 2.98-2.88 (m, 1H, CH$_3$), 2.76-2.64 (m, 1H, CH$_3$), 1.44 (d, $^3J_{HH}$=6.4 Hz, 3H, CH$_3$); HRMS (ESI) calcd for C$_{15}$H$_{20}$N$_5$O$_3$[M+H]$^+$ 350.1612. found 350.1606.

(1S, 3S)—N'-benzoyl-1-methyl-2,3,4,9-tetrahydro-pyridino [3,4-b] indol-3-formylhydrazine (I$_d$-4)

yellow solid, yield 93%, melting point 140-143° C.;
$^1$H NMR (400 MHz, DMSO-d$_6$) δ 10.83 (s, 1H, NH), 10.47 (br, 1H, O=C—NH), 10.02 (br, 1H, and O=C—NH), 7.92 (d, $^3J_{HH}$=7.2 Hz, 2H, Ph-H), 7.60 (t, $^3J_{HH}$=7.2 Hz, 1H, Ph-H), 7.52 (t, $^3J_{HH}$=7.2 Hz, 2H, Ph-H), 7.40 (d, $^3J_{HH}$=7.2 Hz, 1H, Ar—H), 7.31 (d, $^3J_{HH}$=8.0 Hz, 1H, Ar—H), 7.04 (t, $^3J_{HH}$=7.2 Hz, 1H, Ar—H), 6.97 (t, $^3J_{HH}$=7.2 Hz, 1H, Ar—H), 4.20-4.11 (m, 1H, CH), 3.66 (dd, $^3J_{HH}$=10.0 Hz, 3.2 Hz, 1H, CH), 2.95 (dd, $^3J_{HH}$=2.8 Hz, $^3J_{HH}$=14.4 Hz, 1H, CH$_2$), 2.75-2.65 (m, 1H, CH$_2$), 1.45 (d, $^3J_{HH}$=6.8 Hz, 3H, CH$_3$); HRMS (ESI) calcd for C$_{30}$H$_{21}$N$_4$O$_2$[M+H]$^+$ 349.1659. found 349.1665.

(1S, 3S)—N'—N-Hexanoyl-1-methyl-2,3,4,9-tetra-hydropyridino [3,4-b] indol-3-formylhydrazine (I$_d$-5)

Light yellow solid, yield 78%, melting point 97-100° C.;
$^1$H NMR (400 MHz, DMSO-d$_6$) δ 10.79 (s, 1H, NH), 9.87 (s, 1H, O=C—NH), 9.81 (br, 1H, O=C—NH), 7.37 (d, $^3J_{HH}$=7.6 Hz, 1H, Ar—H), 7.29 (d, $^3J_{HH}$=8.0 Hz, 1H, Ar—H), 7.03 (t, $^3J_{HH}$=7.2 Hz, 1H, Ar—H), 6.95 (t, $^3J_{HH}$=7.2 Hz, 1H, Ar—H), 4.15-4.03 (m, 1H, CH), 3.55 (dd, $^3J_{HH}$=10.4 Hz, 3.6 Hz, 1H, CH), 2.87 (dd, $^3J_{HH}$=2.4 Hz, $^2J_{HH}$=14.8 Hz, 1H, CH$_2$), 2.62 (ddd, $^3J_{HH}$=2.0 Hz, $^3J_{HH}$=10.8 Hz, $^2J_{HH}$=14.8 Hz, 1H, CH$_2$), 2.15 (t, $^3J_{HH}$=7.2 Hz, 2H, CH$_2$), 1.60-1.48 (m, 2H, CH$_2$), 1.42 (d, $^3J_{HH}$=6.8 Hz, 3H, CH$_3$), 1.24-1.21 (m, 4H, CH$_2$CH$_2$), 6.88 (t, $^3J_{HH}$=6.8 Hz, 2H, CH$_2$); HRMS (ESI) calcd for C$_{19}$H$_{27}$N$_8$O$_2$[M+H]$^+$ 343.2129. found 343.2132.

(1S, 3S)—N'-tert-valeryl-1-methyl-2,3,4,9-tetrahy-dropyridino [3,4-b] indol-3-formylhydrazine (I$_d$-6)

Yellow solid, yield 93%, melting point 124-126° C.;
$^1$H NMR (400 MHz, CDCl$_3$) δ 8.83 (br, 1H, O=C—NH), 8.34 (s, 1H, O=C—NH), 7.25 (d, $^3J_{HH}$=7.6 Hz, 1H, Ar—H), 7.15 (d, $^3J_{HH}$=7.6 Hz, 1H, Ar—H), 7.00 (t, $^3J_{HH}$=7.2 Hz, 1H, Ar—H), 6.93 (t, $^3J_{HH}$=7.2 Hz, 1H, Ar—H), 3.95-3.81 (m, 1H, CH), 3.49 (dd, $^3J_{HH}$=10.8 Hz, 1H, CH), 3.05-2.97 (m, 1H, CH$_2$), 2.63-2.50 (m, 1H, CH$_2$), 1.30-1.07 (m, 12H, CH$_3$); HRMS (ESI) calcd for C$_{18}$H$_{25}$N$_6$O$_2$[M+H]$^+$ 329.1972. found 429.1975.

(1S, 3S)—N'-(cyclopentyl formyl)-1-methyl-2,3,4, 9-tetrahydropyridino [3,4-b] indol-3-formylhydra-zine (I$_d$-7)

White solid, yield 80%, melting point 141-144° C.;
$^1$H NMR (400 MHz, DMSO-d$_6$) δ 10.83 (s, 1H, NH), 9.94-9.74 (m, 2H, O=C—NH), 7.37 (d, $^3J_{HH}$=7.6 Hz, 1H, Ar—H), 7.30 (d, $^3J_{HH}$=8.0 Hz, 1H, Ar—H), 7.03 (t, $^3J_{HH}$=7.2 Hz, 1H, Ar—H), 6.96 (t, $^3J_{HH}$=7.2 Hz, 1H, Ar—H), 4.19-4.06 (m, 1H, CH), 3.66-3.54 (m, 1H, CH), 2.96-2.84 (m, 1H, CH$_2$), 2.72-2.57 (m, 2H, CH$_2$ and cyclo-pentyl-CH), 1.85-1.48 (m, 8H, cyclopentyl-CH$_2$), 1.43 (d, $^3J_{HH}$=6.4 Hz, 3H, CH$_3$); HRMS (ESI) calcd for C$_{19}$H$_{25}$N$_8$O$_2$[M+H]$^+$ 341.1972. found 341.1968.

Embodiment 21: Determination of Activity Against Tobacco Mosaic Virus, and the Determination Procedure is as Follows 1. Virus Purification and Concentration Determination:

Virus purification and concentration determination are executed by referring to the SOP for tobacco mosaic virus formulated by Bioassay Laboratory of the Research Institute of Elmento-organic Chemistry at Nankai University. After the crude extract of virus undergoes centrifugal treatment of polyethylene glycol twice, its concentration is determined. It is kept at 4° C. for future use.

2. Preparation of a Compound Solution:

After weighing, DMF is added to dissolve the crude drug and obtain a 1×10$^5$ m/mL mother solution. Then it is diluted with a 1%0 Tween 80 aqueous solution to the needed concentration; water is added to ningnanmycin formulation for dilution.

3. In Vitro Effect:

Mechanically inoculate the leaves of *Nicotiana tabacum* L.cv.Xanthi NN at an appropriate age and wash them with water (virus concentration is 10 m/mL). Cut them off after water drains, halves each leaf along the midrib, soak the left half leaf and the right half leaf in 1%0 Tween water and drug respectively, take them out 30 min later, and culture them at appropriate illumination and temperature in a moist state. Use 3 leaves each time and repeat the test 3 times. Record the number of necrotic lesions and calculate the preventive effect 3d later.

4. In Vivo Protective Effect:

Select evenly growing *Nicotiana tabacum* L.cv.Xanthi NN in 3-5-leaf stage, spray drug to the whole plants, repeat the treatment 3 times, and use 1‰ Tween 80 aqueous solution as control. Sprinkle emery (50 mesh) on leaf surface 24 h later, dip virus solution by a writing brush, smear the solution on the whole leaves along the direction of branch veins twice, hold up the leaves with palm under them (virus concentration is 10 μg/mL) and wash the leaves with running water after inoculation. Record the number of necrotic lesions and calculate the preventive effect 3d later.

5. In Vivo Therapeutic Effect:

Select evenly growing *Nicotiana tabacum* L.cv.Xanthi NN in 3-5-leaft stage, inoculate the virus to whole leaves by a writing brush (virus concentration is 10 μg/mL), and wash the leaves with running water after inoculation. Spray drug to the whole plants after the water on leaf surface drains, repeat the treatment for 3 times, and use 1‰ Tween 80 aqueous solution as control. Record the number of necrotic lesions and calculate the preventive effect 3d later.

6. In Vivo Inactivation:

Select evenly growing *Nicotiana tabacum* L.cv.Xanthi NN in 3-5-leaft stage, mix the drug with virus juice in an equal volume for inactivation, mechanically inoculate it 30 min later (virus concentration is 20 μg/mL), wash with running water after inoculation, repeat the treatment for 3 times, and use 1‰ Tween 80 aqueous solution as control. Record the number of necrotic lesions and calculate the result 3d later.

Inhibition rate (%)=[(number of necrotic lesions in the control group−number of necrotic lesions in the treatment group)/number of necrotic lesions in the control group]×100%

TABLE 1

Test results of anti-TMV activity of some of β-carboline, dihydro-β-carboline and tetrahydro-β-carboline alkaloids and their derivatives ($I_a$, $I_b$, $I_c$ and $I_d$):

| | | Relative inhibition rate (%) | | | |
|---|---|---|---|---|---|
| No. | Treatment dose (μg/mL) | In vitro activity | In vivo inactivation | In vivo therapy | In vivo protection |
| Harmalan | 500 | 58.6 | 62.3 | 55.1 | 60.3 |
| | 100 | 30 | 32.7 | 34.8 | 35.6 |
| Tetrahydroharmane | 500 | 63.7 | 64.2 | 57.2 | 59.5 |
| | 100 | 28.4 | 23.5 | 20.4 | 24.6 |
| Harmane | 500 | 54.3 | 50.6 | 50 | 57.8 |
| | 100 | 16.4 | 17.7 | 23.7 | 26.9 |
| Tetrahydroharmine | 500 | 58.2 | 59.8 | 55.5 | 54.6 |
| | 100 | 28.7 | 26.4 | 27.3 | 24.2 |
| Harmine | 500 | 44.6 | 40.5 | 38.6 | 42.4 |
| | 100 | 20 | 11.4 | 15.8 | 16.3 |
| Harmol | 500 | 32.6 | 35.1 | 30 | 36.7 |
| | 100 | 0 | 0 | 0 | 9.5 |
| $I_a$-1 | 500 | 44.5 | 46.3 | 47.4 | 51.2 |
| | 100 | 18.2 | 14.9 | 19.3 | 20.4 |
| $I_a$-3 | 500 | 15.7 | 21.5 | 18.5 | 26.1 |
| | 100 | 0 | 0 | 0 | 0 |
| $I_a$-4 | 500 | 30 | 36.4 | 33.3 | 30.1 |
| | 100 | 0 | 10.5 | 0 | 5.8 |
| $I_a$-5 | 500 | 31.3 | 29.5 | 32.7 | 40.3 |
| | 100 | 0 | 0 | 0 | 5.8 |
| $I_a$-6 | 500 | 12.6 | 12 | 15.6 | 18.7 |
| | 100 | 0 | 0 | 0 | 0 |
| $I_a$-7 | 500 | 30 | 20.3 | 24.1 | 27.2 |
| | 100 | 0 | 0 | 0 | 0 |
| $I_a$-8 | 500 | 0 | 15.3 | 0 | 14.4 |
| | 100 | 0 | 0 | 0 | 0 |
| $I_a$-9 | 500 | 20.7 | 13.6 | 12.5 | 19.6 |
| | 100 | 0 | 0 | 0 | 0 |
| $I_a$-10 | 500 | 33.3 | 26.3 | 28.8 | 23.7 |
| | 100 | 0 | 0 | 0 | 0 |
| $I_a$-11 | 500 | 32.5 | 27.3 | 29.6 | 21.4 |
| | 100 | 0 | 0 | 0 | 0 |
| $I_a$-14 | 500 | 25.8 | 18.4 | 21.5 | 28.4 |
| | 100 | 0 | 0 | 0 | 0 |
| $I_a$-15 | 500 | 40.2 | 39.6 | 36.2 | 35.1 |
| | 100 | 0 | 13.5 | 10 | 10.2 |
| $I_a$-16 | 500 | 17.8 | 26.5 | 20.2 | 21.3 |
| | 100 | 0 | 0 | 0 | 0 |
| $I_b$-1 | 500 | 41.6 | 35.5 | 40.4 | 41.3 |
| | 100 | 18.9 | 13.5 | 15.8 | 20 |
| $I_b$-2 | 500 | 25 | 28.6 | 31.5 | 29.7 |
| | 100 | 0 | 0 | 0 | 0 |
| $I_b$-5 | 500 | 19.7 | 27.6 | 24.3 | 32.3 |
| | 100 | 0 | 0 | 0 | 0 |
| $I_b$-6 | 500 | 25 | 17.5 | 21.4 | 24.8 |
| | 100 | 0 | 0 | 0 | 0 |
| $I_b$-7 | 500 | 26.9 | 36.5 | 30.7 | 40.1 |
| | 100 | 12.3 | 19.3 | 15.9 | 16.2 |
| $I_b$-8 | 500 | 48.2 | 51.3 | 42.2 | 43.2 |
| | 100 | 13.4 | 20.3 | 17.1 | 17.6 |
| $I_b$-9 | 500 | 44.5 | 41 | 42.7 | 40.4 |
| | 100 | 12.8 | 16.9 | 14.3 | 17.2 |
| $I_b$-10 | 500 | 34.1 | 46.4 | 38.1 | 36.6 |
| | 100 | 0 | 12.6 | 11.4 | 10.7 |
| $I_b$-11 | 500 | 40.9 | 37 | 38.9 | 36.7 |
| | 100 | 0 | 13.1 | 18 | 14.3 |
| $I_b$-12 | 500 | 40 | 35.8 | 38.6 | 41.9 |
| | 100 | 12.6 | 16.7 | 12.9 | 17 |
| $I_b$-13 | 500 | 46.5 | 50.4 | 43.9 | 47.9 |
| | 100 | 21.8 | 25.7 | 17.5 | 18.6 |
| $I_b$-14 | 500 | 42.6 | 35.7 | 45.8 | 47 |
| | 100 | 11.1 | 0 | 15.9 | 21.4 |
| $I_b$-15 | 500 | 50 | 46 | 48.2 | 49.6 |
| | 100 | 21.4 | 16.5 | 20.3 | 23.4 |
| $I_b$-16 | 500 | 38.4 | 44 | 44.9 | 42.1 |
| | 100 | 0 | 13.5 | 21.1 | 15.8 |
| $I_b$-17 | 500 | 38.8 | 43.3 | 44.6 | 37.1 |
| | 100 | 0 | 12.3 | 15.1 | 14.2 |
| $I_b$-18 | 500 | 37.6 | 41.5 | 40 | 41 |
| | 100 | 5.4 | 10 | 18.6 | 12.1 |
| $I_b$-19 | 500 | 26.6 | 18.5 | 20.9 | 24.7 |
| | 100 | 0 | 0 | 0 | 0 |
| $I_b$-20 | 500 | 37.5 | 39.1 | 34.2 | 29.6 |
| | 100 | 0 | 9.8 | 0 | 0 |
| $I_c$-1 | 500 | 55.8 | 56.3 | 51.5 | 53.2 |
| | 100 | 28.4 | 19.6 | 16 | 21.8 |
| $I_c$-2 | 500 | 52.4 | 50.3 | 47 | 53.8 |
| | 100 | 17.6 | 13.3 | 18.2 | 21.7 |
| $I_c$-3 | 500 | 56.8 | 64.5 | 60.4 | 62.4 |
| | 100 | 20.4 | 25 | 23.1 | 18.9 |
| $I_c$-4 | 500 | 62.8 | 58.3 | 57.1 | 61.5 |
| | 100 | 19.6 | 27.4 | 20.8 | 21.4 |
| $I_c$-5 | 500 | 67.3 | 70.4 | 71.5 | 64.2 |
| | 100 | 30.8 | 35.9 | 29.2 | 34.1 |
| $I_c$-6 | 500 | 56.8 | 66.7 | 60.4 | 57.2 |
| | 100 | 20.1 | 28.5 | 31.5 | 18.6 |
| $I_c$-7 | 500 | 50.7 | 55.2 | 48.9 | 48.1 |
| | 100 | 15.1 | 20.4 | 23.5 | 14.8 |
| $I_c$-8 | 500 | 62.5 | 69.1 | 66.4 | 70 |
| | 100 | 28.7 | 30.4 | 34.8 | 31.8 |
| $I_c$-9 | 500 | 53.2 | 59.2 | 54 | 54.7 |
| | 100 | 13.2 | 22.1 | 16.5 | 20.6 |
| $I_c$-10 | 500 | 38.5 | 43.2 | 36.4 | 34.8 |
| | 100 | 0 | 0 | 10.9 | 0 |
| $I_c$-11 | 500 | 37.2 | 47.1 | 40.5 | 42.3 |
| | 100 | 7.8 | 20.3 | 16.2 | 11 |

TABLE 1-continued

Test results of anti-TMV activity of some of β-carboline, dihydro-β-carboline and tetrahydro-β-carboline alkaloids and their derivatives ($I_a$, $I_b$, $I_c$ and $I_d$):

| No. | Treatment dose (μg/mL) | Relative inhibition rate (%) | | | |
|---|---|---|---|---|---|
| | | In vitro activity | In vivo inactivation | In vivo therapy | In vivo protection |
| $I_c$-12 | 500 | 72.6 | 74.5 | 69 | 68.1 |
| | 100 | 29.1 | 33.6 | 30.2 | 35.8 |
| $I_c$-13 | 500 | 46.5 | 43.6 | 48.1 | 46 |
| | 100 | 19.8 | 15.2 | 18.6 | 10.3 |
| $I_c$-14 | 500 | 40.9 | 45.6 | 43.9 | 47.8 |
| | 100 | 0 | 16.9 | 8.2 | 0 |
| $I_c$-15 | 500 | 36.6 | 43.4 | 39.6 | 37.5 |
| | 100 | 0 | 8.8 | 12.9 | 0 |
| $I_c$-16 | 500 | 33.3 | 41 | 36.9 | 33.6 |
| | 100 | 0 | 11.2 | 5.7 | 0 |
| $I_c$-17 | 500 | 32.7 | 38.9 | 36.8 | 31.4 |
| | 100 | 0 | 9.2 | 0 | 0 |
| $I_c$-18 | 500 | 48.8 | 54.6 | 44.2 | 47.5 |
| | 100 | 15.4 | 18.2 | 9.3 | 11.5 |
| $I_c$-19 | 500 | 49.5 | 61.3 | 63.4 | 54.7 |
| | 100 | 8.8 | 20.2 | 27.8 | 30 |
| $I_c$-20 | 500 | 58.5 | 59.1 | 52.3 | 61.3 |
| | 100 | 23 | 29.6 | 25.1 | 31.8 |
| $I_c$-21 | 500 | 42.4 | 49.6 | 45.3 | 48.1 |
| | 100 | 0 | 21.3 | 12.6 | 18.5 |
| $I_c$-22 | 500 | 35.2 | 47 | 33.2 | 37.1 |
| | 100 | 0 | 8.5 | 0 | 6.7 |
| $I_c$-23 | 500 | 32.6 | 47.1 | 41.3 | 40.5 |
| | 100 | 7.8 | 13.4 | 10.4 | 11.3 |
| $I_c$-24 | 500 | 61.3 | 73.4 | 70.9 | 59.6 |
| | 100 | 23.2 | 32.8 | 31.7 | 27.3 |
| $I_c$-25 | 500 | 59.6 | 75.8 | 62.8 | 69.2 |
| | 100 | 31.2 | 36.3 | 30.4 | 25.7 |
| $I_c$-26 | 500 | 64.4 | 63.7 | 68.2 | 66.8 |
| | 100 | 27.5 | 28.9 | 36.8 | 33.4 |
| $I_c$-27 | 500 | 30.2 | 39.5 | 34.8 | 37.2 |
| | 100 | 9.2 | 13.6 | 11.1 | 7.9 |
| $I_c$-28 | 500 | 58.1 | 59.7 | 55.4 | 56.8 |
| | 100 | 25.6 | 21.3 | 16.7 | 18.9 |
| $I_c$-29 | 500 | 43.4 | 33 | 41.9 | 46.2 |
| | 100 | 8.6 | 12.8 | 10.9 | 14.3 |
| $I_d$-1 | 500 | 52.1 | 44.1 | 54.5 | 58.3 |
| | 100 | 22.6 | 16.2 | 26.8 | 29.9 |
| $I_d$-2 | 500 | 41.2 | 42.9 | 48.8 | 51.3 |
| | 100 | 13.5 | 9.8 | 19.1 | 16 |
| $I_d$-3 | 500 | 39.2 | 45.3 | 45 | 42.1 |
| | 100 | 6.4 | 17.9 | 11.6 | 14.2 |
| $I_d$-4 | 500 | 36.9 | 37.5 | 34.2 | 40 |
| | 100 | 0 | 0 | 0 | 12.1 |
| $I_d$-5 | 500 | 32.1 | 31.5 | 27.3 | 30.9 |
| | 100 | 0 | 0 | 0 | 0 |
| $I_d$-6 | 500 | 45.7 | 44 | 42.1 | 47.5 |
| | 100 | 8.9 | 12.8 | 14.2 | 16.9 |
| $I_d$-7 | 500 | 47.2 | 42.4 | 51.4 | 53.9 |
| | 100 | 22.2 | 20.3 | 18.6 | 26.6 |
| NK-007 | 500 | 65.4 | 65.2 | 67.2 | 67.9 |
| | 100 | 38.7 | 33.9 | 34.9 | 36.2 |
| Virazole | 500 | 39.5 | 36.3 | 35.4 | 37.6 |
| | 100 | 15.3 | 12.9 | 11.9 | 16.2 |
| Ningnanmycin | 500 | 73.3 | 68 | 54.2 | 65.4 |
| | 100 | 26.8 | 38.4 | 20 | 23.1 |

Table 1 indicates most of β-carboline, dihydro-β-carboline and tetrahydro-β-carboline alkaloids and their derivatives ($I_a$, $I_b$, $I_c$ and $I_d$) show very high in vitro anti-TMV activity, most of the compounds show very good in vivo activity against tobacco mosaic virus (TMV), and most of alkaloid and acylhydrazone compounds obviously outperform commercial variety virazole in anti-TMV in vivo activity. Particularly, the anti-TMV activity of compounds Harmalan, Tetrahydroharmane, Harmane, Tetrahydroharmine, $I_a$-1, $I_b$-8, $I_b$-15, $I_c$-1-$I_c$-9, $I_c$-12, $I_c$-19, $I_c$-20, $I_c$-24-$I_c$-26, $I_c$-28, $I_d$-1, $I_d$-6 and $I_d$-7 at 100 μg/mL is equivalent to the activity of commercial variety ningnanmycin at 100 μg/mL, and they have great development value.

Embodiment 22: Determination of Fungicidal Activity, and the Determination Procedure is as Follows In vitro test method (*Alternaria solani* is taken for example. Alternatively, other fungi may be used): Inoculate *Alternaria solani* to PDA culture medium, culture it for 7 days, prepare Φ4 cm bacteria plates from colony edge by a puncher, inoculate 50 m/mL and drug-free PDA culture media, culture them for 4 days, measure colony diameter, compare with the control group and calculate the inhibition percentage of the drug.

TABLE 2

Test results of bactericidal activity of some of β-carboline, dihydro-β-carboline and tetrahydro-β-carboline alkaloids and their derivatives ($I_a$, $I_b$, $I_c$ and $I_d$):

| No. | Cucumber fusarium wilt | Cercospora arachidicola | Macrophoma kawatsukai | Alternaria solani | Fusarium graminearumt | Fusarium fujikuroi | Sclerotinia scleotiorum | Phytophthora capsici | Rhizoctonia cereali | Bipolaria maydis | Colletotrichum orbiculare | potato late blight | Rhizoctonia solani | Botrytis cinerea |
|---|---|---|---|---|---|---|---|---|---|---|---|---|---|---|
| Harmalan | 23.1 | 76.9 | 2.4 | 26.3 | 21.4 | 28.6 | 19.6 | 0.0 | 55.3 | 27.3 | 25.0 | 31.8 | 19.7 | 15.2 |
| Tetrahydr | 19.2 | 61.5 | 26.2 | 26.3 | 14.3 | 14.3 | 9.8 | 0.0 | 42.1 | 18.2 | 32.1 | 18.2 | 52.6 | 12.1 |
| Harmane | 19.2 | 92.3 | 61.9 | 68.4 | 23.8 | 35.7 | 33.3 | 15.6 | 42.1 | 36.4 | 46.4 | 9.1 | 26.3 | 12.1 |
| Tetrahydr | 19.2 | 76.9 | 14.3 | 21.1 | 11.9 | 14.3 | 19.6 | 9.4 | 34.2 | 27.3 | 25.0 | 22.7 | 26.3 | 27.3 |
| Harmine | 28.6 | 57.1 | 35.3 | 83.3 | 92.9 | 57.1 | 48.0 | 60.6 | 71.9 | 31.6 | 57.1 | 35.0 | 21.4 | 59.1 |
| Harmol | 26.9 | 46.2 | 23.8 | 26.3 | 23.8 | 28.6 | 5.9 | 25.0 | 42.1 | 31.8 | 46.4 | 22.7 | 50.0 | 9.1 |
| $I_a$-1 | 65.4 | 84.6 | 61.9 | 73.7 | 76.2 | 64.3 | 41.2 | 93.8 | 68.4 | 86.4 | 92.9 | 45.5 | 96.1 | 45.5 |
| $I_a$-3 | 23.8 | 7.1 | 35.3 | 33.3 | 50.0 | 42.9 | 56.0 | 36.4 | 59.4 | 31.6 | 23.8 | 25.0 | 10.7 | 54.6 |
| $I_a$-4 | 38.5 | 53.9 | 35.7 | 15.8 | 42.9 | 21.4 | 29.4 | 9.4 | 50.0 | 36.4 | 42.9 | 27.3 | 42.1 | 18.2 |
| $I_a$-5 | 34.6 | 53.9 | 2.4 | 21.1 | 23.8 | 14.3 | 9.8 | 25.0 | 36.8 | 22.7 | 39.3 | 18.2 | 6.6 | 0.0 |
| $I_a$-6 | 23.1 | 53.9 | 26.2 | 15.8 | 38.1 | 21.4 | 7.8 | 9.4 | 36.8 | 27.3 | 35.7 | 9.1 | 46.1 | 12.1 |
| $I_a$-7 | 14.3 | 35.7 | 5.9 | 33.3 | 35.7 | 35.7 | 76.0 | 18.2 | 62.5 | 21.1 | 33.3 | 20.0 | 0.0 | 36.4 |
| $I_a$-8 | 52.4 | 71.4 | 76.5 | 66.7 | 78.6 | 50.0 | 80.0 | 93.9 | 90.6 | 79.0 | 71.4 | 50.0 | 42.9 | 54.6 |
| $I_a$-9 | 38.5 | 61.5 | 78.6 | 36.8 | 35.7 | 21.4 | 13.7 | 50.0 | 84.2 | 36.4 | 50.0 | 45.5 | 52.6 | 51.5 |
| $I_a$-10 | 23.8 | 84.6 | 52.9 | 61.1 | 71.4 | 35.7 | 68.0 | 51.5 | 78.1 | 36.8 | 47.6 | 35.0 | 39.3 | 13.6 |
| $I_a$-11 | 19.1 | 50.0 | 82.4 | 33.3 | 35.7 | 35.7 | 72.0 | 60.6 | 53.1 | 21.1 | 38.1 | 25.0 | 42.9 | 63.6 |
| $I_a$-14 | 23.1 | 84.6 | 47.6 | 10.5 | 14.3 | 28.6 | 9.8 | 18.8 | 63.2 | 22.7 | 25.0 | 22.7 | 39.5 | 12.1 |
| $I_a$-15 | 33.3 | 21.4 | 58.8 | 22.2 | 78.6 | 64.3 | 76.0 | 66.7 | 81.3 | 73.7 | 66.7 | 55.0 | 17.9 | 68.2 |
| $I_a$-16 | 4.8 | 0.0 | 23.5 | 22.2 | 42.9 | 28.6 | 76.0 | 9.1 | 53.1 | 15.8 | 23.8 | 15.0 | 0.0 | 4.6 |
| $I_b$-1 | 19.2 | 30.8 | 23.8 | 21.1 | 26.2 | 21.4 | 7.8 | 18.8 | 42.1 | 22.7 | 35.7 | 27.3 | 26.3 | 21.2 |
| $I_b$-2 | 23.1 | 61.5 | 23.8 | 0.0 | 21.4 | 0.0 | 23.5 | 15.6 | 31.6 | 9.1 | 25.0 | 4.6 | 29.0 | 18.2 |
| $I_b$-5 | 19.2 | 69.2 | 11.9 | 15.8 | 26.2 | 42.9 | 9.8 | 12.5 | 44.7 | 22.7 | 35.7 | 22.7 | 36.8 | 21.2 |
| $I_b$-6 | 26.9 | 84.6 | 61.9 | 26.3 | 31.0 | 14.3 | 29.4 | 9.4 | 63.2 | 36.4 | 32.1 | 27.3 | 32.9 | 27.3 |
| $I_b$-7 | 33.3 | 42.9 | 64.7 | 50.0 | 42.9 | 64.3 | 60.0 | 66.7 | 78.1 | 42.1 | 47.6 | 40.0 | 42.9 | 50.0 |
| $I_b$-8 | 33.3 | 71.4 | 64.7 | 83.3 | 50.0 | 50.0 | 72.0 | 51.5 | 84.4 | 89.5 | 38.1 | 35.0 | 55.4 | 50.0 |
| $I_b$-9 | 19.2 | 84.6 | 21.4 | 26.3 | 35.7 | 14.3 | 19.6 | 15.6 | 44.7 | 22.7 | 42.9 | 22.7 | 35.5 | 12.1 |
| $I_b$-10 | 23.8 | 21.4 | 64.7 | 55.6 | 35.7 | 35.7 | 56.0 | 45.5 | 65.6 | 31.6 | 42.9 | 30.0 | 21.4 | 40.9 |
| $I_b$-11 | 23.8 | 42.9 | 61.9 | 26.3 | 28.6 | 28.6 | 76.0 | 36.4 | 65.6 | 15.8 | 42.9 | 35.0 | 17.9 | 40.9 |
| $I_b$-12 | 19.2 | 92.3 | 64.7 | 50.0 | 42.9 | 28.6 | 17.7 | 9.4 | 39.5 | 42.1 | 25.0 | 18.2 | 42.1 | 24.2 |
| $I_b$-13 | 28.6 | 50.0 | 29.4 | 26.3 | 21.4 | 42.9 | 68.0 | 60.6 | 59.4 | 26.3 | 38.1 | 30.0 | 33.9 | 68.2 |
| $I_b$-14 | 23.1 | 69.2 | 33.3 | 55.6 | 42.9 | 28.6 | 29.4 | 15.6 | 65.8 | 36.4 | 42.9 | 36.4 | 59.2 | 36.4 |
| $I_b$-15 | 13.6 | 18.2 | 39.4 | 42.1 | 38.5 | 29.4 | 30.8 | 51.5 | 54.1 | 24.0 | 24.0 | 26.1 | 4.2 | 27.8 |
| $I_b$-16 | 23.1 | 84.6 | 33.3 | 9.5 | 14.3 | 14.3 | 0.0 | 18.8 | 57.9 | 18.2 | 28.6 | 22.7 | 46.1 | 18.2 |
| $I_b$-17 | 34.6 | 69.2 | 47.6 | 21.1 | 59.5 | 28.6 | 33.3 | 37.5 | 71.1 | 45.5 | 50.0 | 31.8 | 50.0 | 27.3 |
| $I_b$-18 | 23.8 | 21.4 | 70.6 | 52.6 | 28.6 | 35.7 | 68.0 | 36.4 | 53.1 | 26.3 | 23.8 | 5.0 | 35.7 | 27.3 |
| $I_b$-19 | 19.2 | 41.2 | 55.6 | 27.8 | 27.6 | 21.4 | 35.3 | 7.9 | 47.1 | 24.0 | 25.9 | 20.0 | 26.3 | 27.3 |
| $I_b$-20 | 15.4 | 23.5 | 27.8 | 25.0 | 24.1 | 21.4 | 0.0 | 18.4 | 47.1 | 16.0 | 18.5 | 20.0 | 13.2 | 36.4 |
| $I_c$-1 | 36.4 | 72.7 | 36.4 | 20.0 | 53.8 | 58.8 | 26.9 | 69.7 | 86.5 | 60.0 | 52.0 | 30.4 | 48.6 | 88.9 |
| $I_c$-2 | 65.4 | 82.4 | 97.2 | 57.1 | 41.4 | 57.1 | 94.1 | 73.7 | 98.0 | 84.0 | 77.8 | 76.0 | 88.2 | 86.4 |
| $I_c$-3 | 38.5 | 76.5 | 97.2 | 70.0 | 31.0 | 35.7 | 41.2 | 78.9 | 96.1 | 64.0 | 48.1 | 72.0 | 63.2 | 72.7 |
| $I_c$-4 | 38.5 | 58.8 | 72.2 | 65.0 | 58.6 | 42.9 | 88.2 | 78.9 | 88.2 | 60.0 | 48.1 | 52.0 | 59.2 | 72.7 |
| $I_c$-5 | 61.5 | 76.5 | 97.2 | 45.0 | 75.9 | 64.3 | 88.2 | 81.6 | 94.1 | 68.0 | 77.8 | 80.0 | 81.6 | 59.1 |
| $I_c$-6 | 27.3 | 45.5 | 48.5 | 42.9 | 53.8 | 47.1 | 46.2 | 60.6 | 56.8 | 56.0 | 60.0 | 39.1 | 45.8 | 52.8 |

TABLE 2-continued

Test results of bactericidal activity of some of β-carboline, dihydro-β-carboline and tetrahydro-β-carboline alkaloids and their derivatives ($I_a$, $I_b$, $I_c$ and $I_d$):

Bactericidal activity (%)/50 mg/kg

| No. | Cucumber fusarium wilt | Cercospora arachidicola | Macrophoma kawatsukai | Alternaria solani | Fusarium graminearumt | Fusarium fujikuroi | Sclerotinia scleotiorum | Phytophthora capsici | Rhizoctonia cereali | Bipolaria maydis | Colletotrichum orbiculare | potato late blight | Rhizoctonia solani | Botrytis cinerea |
|---|---|---|---|---|---|---|---|---|---|---|---|---|---|---|
| $I_c$-7 | 77.3 | 72.7 | 97.0 | 71.4 | 76.9 | 70.6 | 84.6 | 84.8 | 97.3 | 80.0 | 80.0 | 65.2 | 62.5 | 80.6 |
| $I_c$-8 | 23.1 | 64.7 | 72.2 | 30.0 | 65.5 | 64.3 | 94.1 | 73.7 | 84.3 | 68.0 | 55.6 | 52.0 | 59.2 | 59.1 |
| $I_c$-9 | 34.6 | 58.8 | 69.4 | 65.0 | 41.4 | 57.1 | 88.2 | 81.6 | 92.2 | 48.0 | 40.7 | 40.0 | 68.4 | 68.2 |
| $I_c$-10 | 26.9 | 23.5 | 88.9 | 45.0 | 72.4 | 21.4 | 64.7 | 63.2 | 78.4 | 56.0 | 40.7 | 44.0 | 32.9 | 77.3 |
| $I_c$-11 | 22.7 | 45.5 | 66.7 | 52.4 | 30.8 | 47.1 | 21.2 | 84.8 | 89.2 | 52.0 | 72.0 | 30.4 | 44.4 | 66.7 |
| $I_c$-12 | 31.8 | 63.6 | 63.6 | 52.4 | 53.8 | 58.8 | 44.2 | 81.8 | 86.5 | 56.0 | 48.0 | 39.1 | 50.0 | 88.9 |
| $I_c$-13 | 22.7 | 45.5 | 66.7 | 52.4 | 30.8 | 47.1 | 21.2 | 84.8 | 89.2 | 52.0 | 72.0 | 30.4 | 44.4 | 66.7 |
| $I_c$-14 | 19.2 | 47.1 | 77.8 | 30.0 | 10.3 | 28.6 | 88.2 | 84.2 | 86.3 | 56.0 | 48.1 | 44.0 | 28.9 | 72.7 |
| $I_c$-15 | 23.1 | 35.3 | 52.8 | 15.0 | 27.6 | 21.4 | 64.7 | 28.9 | 66.7 | 28.0 | 29.6 | 24.0 | 23.7 | 36.4 |
| $I_c$-16 | 38.5 | 41.2 | 83.3 | 15.0 | 62.1 | 50.0 | 35.3 | 26.3 | 80.4 | 32.0 | 40.7 | 52.0 | 39.5 | 54.5 |
| $I_c$-17 | 23.1 | 23.5 | 75.0 | 20.0 | 20.7 | 21.4 | 5.9 | 18.4 | 41.2 | 16.0 | 25.9 | 12.0 | 21.1 | 36.4 |
| $I_c$-18 | 11.5 | 52.9 | 69.4 | 35.0 | 6.9 | 28.6 | 64.7 | 39.5 | 68.6 | 20.0 | 33.3 | 36.0 | 32.9 | 81.8 |
| $I_c$-19 | 23.1 | 23.5 | 97.2 | 15.0 | 41.4 | 14.3 | 58.8 | 42.1 | 74.5 | 28.0 | 29.6 | 24.0 | 32.9 | 22.7 |
| $I_c$-20 | 26.9 | 47.1 | 55.6 | 45.0 | 62.1 | 28.6 | 88.2 | 68.4 | 72.5 | 44.0 | 44.4 | 36.0 | 46.1 | 72.7 |
| $I_c$-21 | 34.6 | 47.1 | 97.2 | 15.0 | 27.6 | 28.6 | 35.3 | 18.4 | 64.7 | 12.0 | 25.9 | 24.0 | 15.8 | 36.4 |
| $I_c$-22 | 26.9 | 29.4 | 52.8 | 30.0 | 20.7 | 14.3 | 41.2 | 31.6 | 64.7 | 36.0 | 22.2 | 32.0 | 6.6 | 40.9 |
| $I_c$-23 | 19.2 | 17.6 | 69.4 | 45.0 | 6.9 | 0.0 | 64.7 | 5.3 | 43.1 | 12.0 | 14.8 | 20.0 | 6.6 | 9.1 |
| $I_c$-24 | 9.1 | 36.4 | 24.2 | 19.0 | 61.5 | 35.3 | 46.2 | 18.2 | 29.7 | 36.0 | 32.0 | 17.4 | 22.2 | 44.4 |
| $I_c$-25 | 4.5 | 0.0 | 33.3 | 19.0 | 30.8 | 41.2 | 21.2 | 9.1 | 29.7 | 36.0 | 24.0 | 17.4 | 5.6 | 66.7 |
| $I_c$-26 | 4.5 | 18.2 | 36.4 | 19.0 | 46.2 | 29.4 | 15.4 | 12.1 | 48.6 | 20.0 | 24.0 | 17.4 | 8.3 | 36.1 |
| $I_c$-27 | 0.0 | 36.4 | 39.4 | 33.3 | 61.5 | 29.4 | 11.5 | 36.4 | 51.4 | 36.0 | 52.0 | 26.1 | 15.3 | 69.4 |
| $I_c$-28 | 4.5 | 36.4 | 36.4 | 14.3 | 53.8 | 23.5 | 3.8 | 18.2 | 48.6 | 28.0 | 32.0 | 30.4 | 8.3 | 41.7 |
| $I_c$-29 | 0.0 | 18.2 | 9.1 | 19.0 | 46.2 | 29.4 | 7.7 | 12.1 | 48.6 | 32.0 | 32.0 | 26.1 | 15.3 | 52.8 |
| $I_d$-1 | 13.6 | 18.2 | 51.5 | 19.0 | 61.5 | 47.1 | 26.9 | 27.3 | 43.2 | 36.0 | 32.0 | 17.4 | 1.4 | 44.4 |
| $I_d$-2 | 4.5 | 18.2 | 39.4 | 14.3 | 53.8 | 29.4 | 19.2 | 6.1 | 45.9 | 28.0 | 24.0 | 30.4 | 0.0 | 61.1 |
| $I_d$-3 | 13.6 | 27.3 | 39.4 | 14.3 | 53.8 | 29.4 | 3.8 | 15.2 | 18.9 | 16.0 | 36.0 | 26.1 | 15.3 | 55.6 |
| $I_d$-4 | 13.6 | 27.3 | 45.5 | 33.3 | 38.5 | 29.4 | 7.7 | 18.2 | 35.1 | 28.0 | 32.0 | 17.4 | 5.6 | 55.6 |
| $I_d$-5 | 22.7 | 45.5 | 63.6 | 23.8 | 46.2 | 29.4 | 26.9 | 21.2 | 29.7 | 32.0 | 28.0 | 26.1 | 1.4 | 66.7 |
| $I_d$-6 | 4.5 | 9.1 | 42.4 | 14.3 | 30.8 | 29.4 | 17.3 | 12.1 | 10.8 | 20.0 | 24.0 | 26.1 | 5.6 | 50.0 |
| $I_d$-7 | 9.1 | 9.1 | 33.3 | 9.5 | 15.4 | 29.4 | 7.7 | 15.2 | 29.7 | 28.0 | 16.0 | 21.7 | 1.4 | 50.0 |
| Carbendazim | <50 | <50 | <50 | <50 | 100 | <50 | 100 | <50 | 100 | 100 | 100 | 100 | 100 | <50 |
| Chlorothalonil | 100 | 73.3 | 100 | 73.3 | <50 | 100 | <50 | 100 | 100 | 91.3 | 91.3 | 86.4 | 100 | 100 |

Table 2 indicates most of β-carboline, dihydro-β-carboline and tetrahydro-β-carboline alkaloids and their derivatives ($I_a$, $I_b$, $I_c$ and $I_d$) show high bactericidal activity against 14 kinds of fungi, and particularly, compound $I_a$-1, $I_c$-2, $I_c$-5 and $I_c$-7 show very good bactericidal activity against various kinds of fungi.

Embodiment 23: Determination of Activity Against Armyworms, Cotton Bollworms and Corn Borers. The Determination Procedure is as Follows Test of Activity Against Cotton Bollworms Experimental method of cotton bollworms: feed and drug mixing method: measure 3 mL of prepared solution and add it to about 27 g of newly prepared feed, thereby obtaining needed concentration through dilution by 10 times. Pour the evenly mixed drug into clean 24-well plates, cool it in the air, put 24 third instar cotton bollworms, observe them for 3-4 days and then check results.

Test of Activity Against Armyworms

Experimental method of armyworms: leaf soaking method: prepare a drug solution at the needed concentration, soak leaves with a diameter of about 5-6 cm in the drug solution for 5-6 s, take them out, put them on absorbent paper, dry them in the air, put them in a designated culture dish, put 10 third instar larvae, transfer them to a 27±1° C. insectariums, observe them for 3-4 days and then check results.

Test of Activity Against Corn Borers

Experimental method of corn borers: leaf soaking method: prepare a drug solution at the needed concentration, soak leaves with a diameter of about 5-6 cm in the drug solution for 5-6 s, take them out, put them on absorbent paper, dry them in the air, put them in a designated culture dish, put 10 third instar larvae, transfer them to a 27±1° C. insectariums, observe them for 3-4 days and then check results.

TABLE 3

Test results of the activity of some of β-carboline, dihydro-β-carboline and tetrahydro-β-carboline alkaloids and their derivatives ($I_a$, $I_b$, $I_c$ and $I_d$) against armyworms, cotton bollworms and corn borers:

| | Armyworm | | Cotton bollworm | | Corn borer | |
|---|---|---|---|---|---|---|
| No. | Concentration (mg/kg) | Mortality (%) | Concentration (mg/kg) | Mortality (%) | Concentration (mg/kg) | Mortality (%) |
| Harmalan | 600 | 20 | 600 | 10 | 600 | 15 |
| Tetrahydroharmane | 600 | 15 | 600 | 15 | 600 | 10 |
| Harmane | 600 | 45 | 600 | 35 | 600 | 35 |
| Tetrahydroharmine | 600 | 0 | 600 | 10 | 600 | 0 |
| Harmine | 600 | 20 | 600 | 15 | 600 | 15 |
| Harmol | 600 | 50 | 600 | 20 | 600 | 45 |
| $I_a$-1 | 600 | 30 | 600 | 20 | 600 | 25 |
| $I_a$-3 | 600 | 50 | 600 | 35 | 600 | 50 |
| $I_a$-4 | 600 | 10 | 600 | 10 | 600 | 5 |
| $I_a$-5 | 600 | 10 | 600 | 15 | 600 | 10 |
| $I_a$-6 | 600 | 45 | 600 | 20 | 600 | 35 |
| $I_a$-7 | 600 | 35 | 600 | 30 | 600 | 25 |
| $I_a$-8 | 600 | 70 | 600 | 15 | 600 | 65 |
| $I_a$-9 | 600 | 5 | 600 | 20 | 600 | 5 |
| $I_a$-10 | 600 | 30 | 600 | 40 | 600 | 30 |
| $I_a$-11 | 600 | 10 | 600 | 10 | 600 | 10 |
| $I_a$-14 | 600 | 25 | 600 | 30 | 600 | 20 |
| $I_a$-15 | 600 | 15 | 600 | 15 | 600 | 5 |
| $I_a$-16 | 600 | 10 | 600 | 5 | 600 | 10 |
| $I_b$-1 | 600 | 25 | 600 | 25 | 600 | 25 |
| $I_b$-2 | 600 | 10 | 600 | 25 | 600 | 10 |
| $I_b$-5 | 600 | 50 | 600 | 30 | 600 | 35 |
| $I_b$-6 | 600 | 45 | 600 | 20 | 600 | 40 |
| $I_b$-7 | 600 | 5 | 600 | 20 | 600 | 5 |
| $I_b$-8 | 600 | 5 | 600 | 20 | 600 | 0 |
| $I_b$-9 | 600 | 15 | 600 | 10 | 600 | 10 |
| $I_b$-10 | 600 | 30 | 600 | 15 | 600 | 25 |
| $I_b$-11 | 600 | 5 | 600 | 20 | 600 | 5 |
| $I_b$-12 | 600 | 50 | 600 | 30 | 600 | 50 |
| $I_b$-13 | 600 | 60 | 600 | 30 | 600 | 55 |
| $I_b$-14 | 600 | 10 | 600 | 30 | 600 | 10 |
| $I_b$-15 | 600 | 20 | 600 | 20 | 600 | 30 |
| $I_b$-16 | 600 | 65 | 600 | 50 | 600 | 50 |
| $I_b$-17 | 600 | 45 | 600 | 30 | 600 | 40 |
| $I_b$-18 | 600 | 5 | 600 | 5 | 600 | 5 |
| $I_b$-19 | 600 | 5 | 600 | 60 | 600 | 10 |
| $I_b$-20 | 600 | 65 | 600 | 30 | 600 | 60 |
| $I_c$-1 | 600 | 75 | 600 | 55 | 600 | 60 |
| $I_c$-2 | 600 | 10 | 600 | 30 | 600 | 5 |
| $I_c$-3 | 600 | 25 | 600 | 40 | 600 | 30 |
| $I_c$-4 | 600 | 30 | 600 | 35 | 600 | 35 |
| $I_c$-5 | 600 | 25 | 600 | 25 | 600 | 20 |
| $I_c$-6 | 600 | 45 | 600 | 35 | 600 | 40 |

TABLE 3-continued

Test results of the activity of some of β-carboline, dihydro-β-carboline and tetrahydro-β-carboline alkaloids and their derivatives ($I_a$, $I_b$, $I_c$ and $I_d$) against armyworms, cotton bollworms and corn borers:

| No. | Armyworm Concentration (mg/kg) | Armyworm Mortality (%) | Cotton bollworm Concentration (mg/kg) | Cotton bollworm Mortality (%) | Corn borer Concentration (mg/kg) | Corn borer Mortality (%) |
|---|---|---|---|---|---|---|
| $I_c$-7 | 600 | 5 | 600 | 30 | 600 | 5 |
| $I_c$-8 | 600 | 20 | 600 | 35 | 600 | 15 |
| $I_c$-9 | 600 | 35 | 600 | 30 | 600 | 40 |
| $I_c$-10 | 600 | 25 | 600 | 30 | 600 | 30 |
| $I_c$-11 | 600 | 65 | 600 | 40 | 600 | 55 |
| $I_c$-12 | 600 | 15 | 600 | 30 | 600 | 15 |
| $I_c$-13 | 600 | 30 | 600 | 15 | 600 | 35 |
| $I_c$-14 | 600 | 40 | 600 | 35 | 600 | 45 |
| $I_c$-15 | 600 | 15 | 600 | 15 | 600 | 20 |
| $I_c$-16 | 600 | 20 | 600 | 10 | 600 | 30 |
| $I_c$-17 | 600 | 25 | 600 | 20 | 600 | 20 |
| $I_c$-18 | 600 | 10 | 600 | 20 | 600 | 15 |
| $I_c$-19 | 600 | 70 | 600 | 50 | 600 | 60 |
| $I_c$-20 | 600 | 35 | 600 | 20 | 600 | 30 |
| $I_c$-21 | 600 | 40 | 600 | 45 | 600 | 35 |
| $I_c$-22 | 600 | 40 | 600 | 20 | 600 | 50 |
| $I_c$-23 | 600 | 15 | 600 | 10 | 600 | 10 |
| $I_c$-24 | 600 | 45 | 600 | 20 | 600 | 50 |
| $I_c$-25 | 600 | 45 | 600 | 20 | 600 | 55 |
| $I_c$-26 | 600 | 25 | 600 | 20 | 600 | 30 |
| $I_c$-27 | 600 | 20 | 600 | 30 | 600 | 30 |
| $I_c$-28 | 600 | 45 | 600 | 45 | 600 | 40 |
| $I_c$-29 | 600 | 20 | 600 | 25 | 600 | 15 |
| $I_d$-1 | 600 | 35 | 600 | 15 | 600 | 35 |
| $I_d$-2 | 600 | 40 | 600 | 40 | 600 | 40 |
| $I_d$-3 | 600 | 25 | 600 | 40 | 600 | 25 |
| $I_d$-4 | 600 | 10 | 600 | 30 | 600 | 15 |
| $I_d$-5 | 600 | 5 | 600 | 30 | 600 | 25 |
| $I_d$-6 | 600 | 35 | 600 | 25 | 600 | 50 |
| $I_d$-7 | 600 | 40 | 600 | 30 | 600 | 40 |

Table 3 indicates most of β-carboline, dihydro-β-carboline and tetrahydro-β-carboline alkaloids and their derivatives ($I_a$, $I_b$, $I_c$ and $I_d$) show certain activity against armyworms, cotton bollworms and corn borers. Particularly, compounds $I_a$-8, $I_b$-13, $I_b$-16, $I_b$-20, $I_c$-1, $I_c$-11 and $I_c$-19 show broad-spectrum activity.

Embodiment 24: Determination of Activity Against Mosquito Larvae, and the Determination Procedure is as Follows Test of Activity Against Mosquito Larvae Experimental method of mosquito larvae: *culex pipiens pallens*, a normal colony raised indoors. Weigh about 5 mg of the compound for test, put it in a penicillin vial, add 5 mL of acetone (or an appropriate solvent), and shake and dissolve it to obtain a 1000 ppm mother solution. Pipette 0.5 mL of the mother solution, add it to a 100 mL beaker filled with 89.9 mL of water, select 10 mosquito larvae at the beginning of the fourth instar, and pour them to a beaker together with 10 mL of feeding solution. The concentration of the drug solution is 5 ppm. Put it in a standard treatment room and check the result 24 h later. Use an aqueous solution containing 0.5 mL of test solvent as a blank.

TABLE 4

Test results of the activity of some of β-carboline, dihydro-β-carboline and tetrahydro-β-carboline alkaloids and their derivatives ($I_a$, $I_b$, $I_c$ and $I_d$) against mosquito larvae:

| No. | Mosquito larvae Concentration (mg/kg) | Mosquito larvae Mortality (%) | No. | Larvae Concentration (mg/kg) | Larvae Mortality (%) |
|---|---|---|---|---|---|
| Harmalan | 10 | 35 | $I_b$-19 | 10 | 20 |
| Tetrahydroharmane | 10 | 30 | $I_b$-20 | 10 | 100 |
| Harmane | 10 | 100 | | 5 | 40 |
| | 5 | 10 | $I_c$-1 | 10 | 100 |
| Tetrahydroharmine | 10 | 15 | | 5 | 80 |
| Harmine | 10 | 45 | $I_c$-2 | 10 | 20 |
| Harmol | 10 | 100 | $I_c$-3 | 10 | 55 |
| | 5 | 30 | $I_c$-4 | 10 | 65 |
| $I_a$-1 | 10 | 50 | $I_c$-5 | 10 | 50 |
| $I_a$-3 | 10 | 100 | $I_c$-6 | 10 | 100 |
| | 5 | 60 | | 5 | 20 |
| $I_a$-4 | 10 | 30 | $I_c$-7 | 10 | 10 |
| $I_a$-5 | 10 | 30 | $I_c$-8 | 10 | 35 |
| $I_a$-6 | 10 | 100 | $I_c$-9 | 10 | 75 |
| | 5 | 20 | $I_c$-10 | 10 | 50 |
| $I_a$-7 | 10 | 65 | $I_c$-11 | 10 | 100 |
| $I_a$-8 | 10 | 100 | | 5 | 40 |
| | 5 | 60 | $I_c$-12 | 10 | 15 |
| $I_a$-9 | 10 | 25 | $I_c$-13 | 10 | 60 |
| $I_a$-10 | 10 | 65 | $I_c$-14 | 10 | 75 |
| $I_a$-11 | 10 | 50 | $I_c$-15 | 10 | 30 |
| $I_a$-14 | 10 | 35 | $I_c$-16 | 10 | 40 |
| $I_a$-15 | 10 | 35 | $I_c$-17 | 10 | 50 |
| $I_a$-16 | 10 | 20 | $I_c$-18 | 10 | 25 |
| $I_b$-1 | 10 | 55 | $I_c$-19 | 10 | 100 |
| $I_b$-2 | 10 | 30 | | 5 | 80 |

TABLE 4-continued

Test results of the activity of some of β-carboline, dihydro-β-carboline and tetrahydro-β-carboline alkaloids and their derivatives ($I_a$, $I_b$, $I_c$ and $I_d$) against mosquito larvae:

| | Mosquito larvae | | | Larvae | |
|---|---|---|---|---|---|
| No. | Concentration (mg/kg) | Mortality (%) | No. | Concentration (mg/kg) | Mortality (%) |
| $I_b$-5 | 10 | 100 | $I_c$-20 | 10 | 75 |
|  | 5 | 30 | $I_c$-21 | 10 | 85 |
| $I_b$-6 | 10 | 100 | $I_c$-22 | 10 | 85 |
|  | 5 | 20 | $I_c$-23 | 10 | 35 |
| $I_b$-7 | 10 | 15 | $I_c$-24 | 10 | 100 |
| $I_b$-8 | 10 | 10 |  | 5 | 10 |
| $I_b$-9 | 10 | 35 | $I_c$-25 | 10 | 100 |
| $I_b$-10 | 10 | 60 |  | 5 | 10 |
| $I_b$-11 | 10 | 15 | $I_c$-26 | 10 | 55 |
| $I_b$-12 | 10 | 100 | $I_c$-27 | 10 | 40 |
|  | 5 | 40 | $I_c$-28 | 10 | 100 |
| $I_b$-13 | 10 | 100 |  | 5 | 20 |
|  | 5 | 60 | $I_c$-29 | 10 | 45 |
| $I_b$-14 | 10 | 30 | $I_d$-1 | 10 | 75 |
| $I_b$-15 | 10 | 40 | $I_d$-2 | 10 | 80 |
| $I_b$-16 | 10 | 100 | $I_d$-3 | 10 | 50 |
|  | 5 | 60 | $I_d$-4 | 10 | 25 |
| $I_b$-17 | 10 | 100 | $I_d$-5 | 10 | 10 |
|  | 5 | 10 | $I_d$-6 | 10 | 65 |
| $I_b$-18 | 10 | 10 | $I_d$-7 | 10 | 80 |

Table 4 indicates most of β-carboline, dihydro-β-carboline and tetrahydro-β-carboline alkaloids and their derivatives ($I_a$, $I_b$, $I_c$ and $I_d$) show high activity against *culex pipiens* larvae, and $I_a$-3, $I_a$-8, $I_b$-13, $I_b$-16, $I_c$-1 and $I_c$-19 still show high activity at 5 mg/kg.

The invention claimed is:

1. A β-carboline compound with a structure shown in the following formula Ic or formula Id

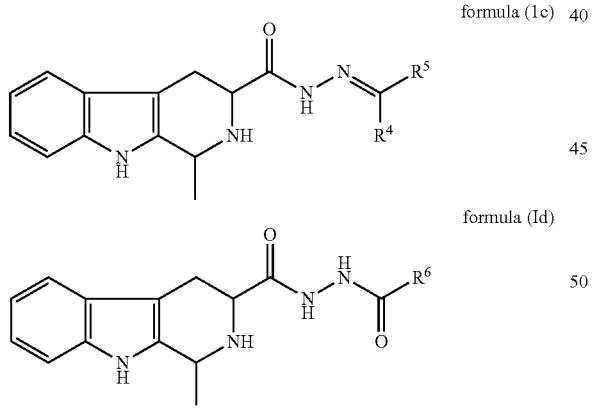

formula (Ic)

formula (Id)

wherein,
R⁴ and R⁵ respectively represent hydrogen, C1-C10 alkyl, C3-C10 nitrogen-containing heterocyclic ring, C1-C10 oxygen-containing heterocyclic ring, or C1-C10 sulfur-containing heterocyclic ring, or R⁴ and R⁵ form a C6 aliphatic ring, or R⁴ is hydrogen and R⁵ is prop-2-enyl; and
R⁶ represents hydrogen, hydroxy, C1-C6 alkoxy, substituted phenyl ring, C1-C10 oxygen-containing heterocyclic ring, or C1-C10 sulfur-containing heterocyclic ring.

2. A β-carboline compound selected from the group consisting of:
(1S, 3S)—N'-benzylidene-1-methyl-2,3,4,9-tetrahydropyridino [3,4-b] indol-3-formylhydrazine ($I_c$-1);
(1S, 3S)—N'-(4-tert-butyl benzylidene)-1-methyl-2,3,4,9-tetrahydropyridino [3,4-b] indol-3-formylhydrazine ($I_c$-2);
(1S, 3S)—N'-(4-dimethyl amino benzylidene)-1-methyl-2,3,4,9-tetrahydropyridino [3,4-b] indol-3-formylhydrazine ($I_c$-3);
(1S, 3S)—N'-(4-nitrobenzylidene)-1-methyl-2,3,4,9-tetrahydropyridino [3,4-b] indol-3-formylhydrazine ($I_c$-4);
(1S, 3S)—N'-(4-chlorobenzylidene)-1-methyl-2,3,4,9-tetrahydropyridino [3,4-b] indol-3-formylhydrazine ($I_c$-5);
(1S, 3S)—N'-(2, 4-dichlorobenzylidene)-1-methyl-2,3,4,9-tetrahydropyridino [3,4-b] indol-3-formylhydrazine ($I_c$-6);
(1S, 3S)—N'-(3,4-dichlorobenzylidene)-1-methyl-2,3,4,9-tetrahydropyridino [3,4-b] indol-3-formylhydrazine ($I_c$-7);
(1S, 3S)—N'-(4-methoxybenzylidene)-1-methyl-2,3,4,9-tetrahydropyridino [3,4-b] indol-3-formylhydrazine ($I_c$-8);
(1S, 3S)—N'-(3-methoxybenzylidene)-1-methyl-2,3,4,9-tetrahydropyridino [3,4-b] indol-3-formylhydrazine ($I_c$-9);
(1S, 3S)—N'-(2-methoxybenzylidene)-1-methyl-2,3,4,9-tetrahydropyridino [3,4-b] indol-3-formylhydrazine ($I_c$-10);
(1S, 3S)—N'-(3,4-dimethoxybenzylidene)-1-methyl-2,3,4,9-tetrahydropyridino [3,4-b] indol-3-formylhydrazine ($I_c$-11);
(1S, 3S)—N'-((benzo [d] [1, 3] dioxymethylene-5)-methylene)-1-methyl-2,3,4,9-tetrahydropyridino [3,4-b] indol-3-formylhydrazine ($I_c$-12);
(1S, 3S)—N'-(2, 3-dihydrobenzo [b] [1, 4] dioxin-6-methylene)-1-methyl-2,3,4,9-tetrahydropyridino [3,4-b] indol-3-formylhydrazine ($I_c$-13);
(1S, 3S)—N'-(6-hydroxynaphthalene-2-methylene)-1-methyl-2,3,4,9-tetrahydropyridino [3,4-b] indol-3-formylhydrazine ($I_c$-14);
(1S, 3S)—N'-(pyridine-4-methylene)-1-methyl-2,3,4,9-tetrahydropyridino [3,4-b] indol-3-formylhydrazine ($I_c$-15);
(1S, 3S)—N'-(pyridine-3-methylene)-1-methyl-2,3,4,9-tetrahydropyridino [3,4-b] indol-3-formylhydrazine ($I_c$-16);
(1S, 3S)—N'-(pyridine-2-methylene)-1-methyl-2,3,4,9-tetrahydropyridino [3,4-b] indol-3-formylhydrazine ($I_c$-17);
(1S, 3S)—N'-(furan-2-methylene)-1-methyl-2,3,4,9-tetrahydropyridino [3,4-b] indol-3-formylhydrazine ($I_c$-18);
(1S, 3S)—N'-(pyrrole-2-methylene)-1-methyl-2,3,4,9-tetrahydropyridino [3,4-b] indol-3-formylhydrazine ($I_c$-19);
(1S, 3S)—N'-(thiophene-2-methylene)-1-methyl-2,3,4,9-tetrahydropyridino [3,4-b] indol-3-formylhydrazine ($I_c$-20);
(1S, 3S)—N'-(imidazole-2-methylene)-1-methyl-2,3,4,9-tetrahydropyridino [3,4-b] indol-3-formylhydrazine ($I_c$-21);
(1S, 3S)—N'-((E)-but-2-enylidene)-1-methyl-2,3,4,9-tetrahydropyridino [3,4-b] indol-3-formylhydrazine ($I_c$-22);

(1S, 3S)—N'-butylidene-1-methyl-2,3,4,9-tetrahydropyridino [3,4-b] indol-3-formylhydrazine ($I_c$-23);

(1S, 3S)—N'-octadien-1-methyl-2,3,4,9-tetrahydropyridino [3,4-b] indol-3-formylhydrazine ($I_c$-24);

(1S, 3S)—N'-(cyclohexylmethylene)-1-methyl-2,3,4,9-tetrahydropyridino [3,4-b] indol-3-formylhydrazine ($I_c$-25);

(1S, 3S)—N'-(2,2-dimethylpropylidene)-1-methyl-2,3,4,9-tetrahydropyridino [3,4-b] indol-3-formylhydrazine ($I_c$-26);

(1S, 3S)—N'-(1-phenylethylidene)-1-methyl-2,3,4,9-tetrahydropyridino [3,4-b] indol-3-formylhydrazine ($I_c$-27);

(1S, 3S)—N'-(3,3-dimethyl-2-butylidene)-1-methyl-2,3,4,9-tetrahydropyridino [3,4-b] indol-3-formylhydrazine ($I_c$-28);

(1S, 3S)—N'-cyclohexylidene-1-methyl-2,3,4,9-tetrahydropyridino [3,4-b] indol-3-formylhydrazine ($I_c$-29);

N'-((1S, 3S)-1-methyl-2,3,4,9-tetrahydropyridino [3,4-b] indol-3-tricarboxylate) benzo [d] [1,2,3] thiadiazole-7-formylhydrazine ($I_d$-i);

4-methyl-N'-((1S, 3S)-1-methyl-2,3,4,9-tetrahydropyridino [3,4-b] indol-3-triformyl)-1, 2, 3-thiadiazole-5-formylhydrazine ($I_d$-2);

(1S, 3S)—N'-isonicotinoyl-1-methyl-2,3,4,9-tetrahydropyridino [3,4-b] indol-3-formylhydrazine ($I_d$-3);

(1S, 3S)—N'-benzoyl-1-methyl-2,3,4,9-tetrahydropyridino [3,4-b] indol-3-formylhydrazine ($I_d$-4);

(1S, 3S)—N'-n-hexanoyl-1-methyl-2,3,4,9-tetrahydropyridino [3,4-b] indol-3-formylhydrazine ($I_d$-5);

(1S, 3S)—N'-tert-valeryl-1-methyl-2,3,4,9-tetrahydropyridino [3,4-b] indol-3-formylhydrazine ($I_d$-G); and (1S, 3S)—N'-(cyclopentyl formyl)-1-methyl-2,3,4,9-tetrahydropyridino [3,4-b] indol-3-formylhydrazine ($I_d$-7).

3. A method for preparing the β-carboline according to claim 2:

regarding $I_c$-1-$I_c$-29, the method comprising:

reacting hydrazide compound $I_b$-15 with fatty aldehyde or aromatic aldehyde to obtain corresponding acylhydrazone compound $I_c$-1-$I_c$-29:

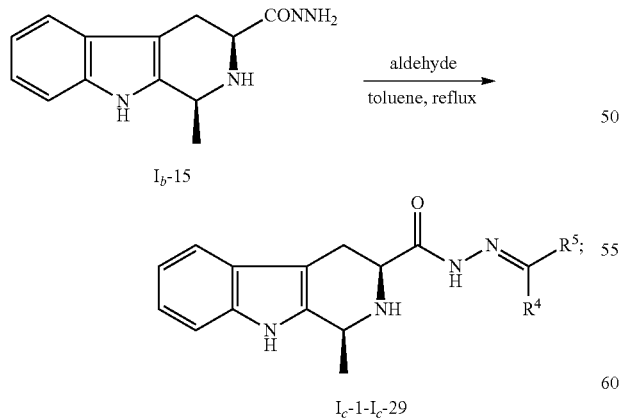

regarding $I_d$-1-$I_d$-7, the method comprising:

reacting hydrazide compound $I_b$-15 with acyl chloride to obtain corresponding bishydrazide compound $I_d$-1-$I_d$-7:

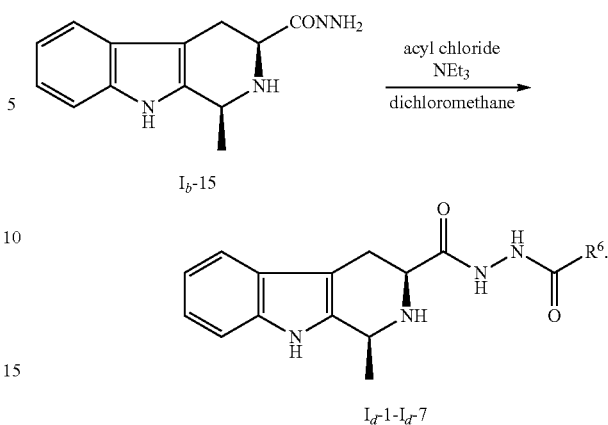

4. A method of treating plant viruses comprising administering the β-carboline compound according to claim 1.

5. A method of treating plant viruses comprising administering a β-carboline compound selected from the group consisting of:

(1S, 3S)—N'-benzylidene-1-methyl-2,3,4,9-tetrahydropyridino [3,4-b] indol-3-formylhydrazine ($I_c$-1);

(1S, 3S)—N'-(4-tert-butyl benzylidene)-1-methyl-2,3,4,9-tetrahydropyridino [3,4-b] indol-3-formylhydrazine ($I_c$-2);

(1S, 3S)—N'-(4-dimethyl amino benzylidene)-1-methyl-2,3,4,9-tetrahydropyridino [3,4-b] indol-3-formylhydrazine ($I_c$-3);

(1S, 3S)—N'-(4-nitrobenzylidene)-1-methyl-2,3,4,9-tetrahydropyridino [3,4-b] indol-3-formylhydrazine ($I_c$-4);

(1S, 3S)—N'-(4-chlorobenzylidene)-1-methyl-2,3,4,9-tetrahydropyridino [3,4-b] indol-3-formylhydrazine ($I_c$-5);

(1S, 3S)—N'-(2, 4-dichlorobenzylidene)-1-methyl-2,3,4,9-tetrahydropyridino [3,4-b] indol-3-formylhydrazine ($I_c$-6);

(1S, 3S)—N'-(3,4-dichlorobenzylidene)-1-methyl-2,3,4,9-tetrahydropyridino [3,4-b] indol-3-formylhydrazine ($I_c$-7);

(1S, 3S)—N'-(4-methoxybenzylidene)-1-methyl-2,3,4,9-tetrahydropyridino [3,4-b] indol-3-formylhydrazine ($I_c$-8);

(1S, 3S)—N'-(3-methoxybenzylidene)-1-methyl-2,3,4,9-tetrahydropyridino [3,4-b] indol-3-formylhydrazine ($I_c$-9);

(1S, 3S)—N'-(2-methoxybenzylidene)-1-methyl-2,3,4,9-tetrahydropyridino [3,4-b] indol-3-formylhydrazine ($I_c$-10);

(1S, 3S)—N'-(3,4-dimethoxybenzylidene)-1-methyl-2,3,4,9-tetrahydropyridino [3,4-b] indol-3-formylhydrazine ($I_c$-11);

(1S, 3S)—N'-((benzo [d] [1, 3] dioxymethylene-5)-methylene)-1-methyl-2,3,4,9-tetrahydropyridino [3,4-b] indol-3-formylhydrazine ($I_c$-12);

(1S, 3S)—N'-(2, 3-dihydrobenzo [b] [1, 4] dioxin-6-methylene)-1-methyl-2,3,4,9-tetrahydropyridino [3,4-b] indol-3-formylhydrazine ($I_c$-13);

(1S, 3S)—N'-(6-hydroxynaphthalene-2-methylene)-1-methyl-2,3,4,9-tetrahydropyridino [3,4-b] indol-3-formylhydrazine ($I_c$-14);

(1S, 3S)—N'-(pyridine-4-methylene)-1-methyl-2,3,4,9-tetrahydropyridino [3,4-b] indol-3-formylhydrazine ($I_c$-15);

(1S, 3S)—N'-(pyridine-3-methylene)-1-methyl-2,3,4,9-tetrahydropyridino [3,4-b] indol-3-formylhydrazine ($I_c$-16);
(1S, 3S)—N'-(pyridine-2-methylene)-1-methyl-2,3,4,9-tetrahydropyridino [3,4-b] indol-3-formylhydrazine ($I_c$-17);
(1S, 3S)—N'-(furan-2-methylene)-1-methyl-2,3,4,9-tetrahydropyridino [3,4-b] indol-3-formylhydrazine ($I_c$-18);
(1S, 3S)—N'-(pyrrole-2-methylene)-1-methyl-2,3,4,9-tetrahydropyridino [3,4-b] indol-3-formylhydrazine ($I_c$-19);
(1S, 3S)—N'-(thiophene-2-methylene)-1-methyl-2,3,4,9-tetrahydropyridino [3,4-b] indol-3-formylhydrazine ($I_c$-20);
(1S, 3S)—N'-(imidazole-2-methylene)-1-methyl-2,3,4,9-tetrahydropyridino [3,4-b] indol-3-formylhydrazine ($I_c$-21);
(1S, 3S)—N'-((E)-but-2-enylidene)-1-methyl-2,3,4,9-tetrahydropyridino [3,4-b] indol-3-formylhydrazine ($I_c$-22);
(1S, 3S)—N'-butylidene-1-methyl-2,3,4,9-tetrahydropyridino [3,4-b] indol-3-formylhydrazine ($I_c$-23);
(1S, 3S)—N'-octadien-1-methyl-2,3,4,9-tetrahydropyridino [3,4-b] indol-3-formylhydrazine ($I_c$-24);
(1S, 3S)—N'-(cyclohexylmethylene)-1-methyl-2,3,4,9-tetrahydropyridino [3,4-b] indol-3-formylhydrazine ($I_c$-25);
(1S, 3S)—N'-(2,2-dimethylpropylidene)-1-methyl-2,3,4,9-tetrahydropyridino [3,4-b] indol-3-formylhydrazine ($I_c$-26);
(1S, 3S)—N'-(1-phenylethylidene)-1-methyl-2,3,4,9-tetrahydropyridino [3,4-b] indol-3-formylhydrazine ($I_c$-27);
(1S, 3S)—N'-(3,3-dimethyl-2-butylidene)-1-methyl-2,3,4,9-tetrahydropyridino [3,4-b] indol-3-formylhydrazine ($I_c$-28);
(1S, 3S)—N'-cyclohexylidene-1-methyl-2,3,4,9-tetrahydropyridino [3,4-b] indol-3-formylhydrazine ($I_c$-29);
N'-((1S, 3S)-1-methyl-2,3,4,9-tetrahydropyridino [3,4-b] indol-3-tricarboxylate) benzo [d] [1,2,3] thiadiazole-7-formylhydrazine ($I_d$-1);
4-methyl-N'-((1S, 3S)-1-methyl-2,3,4,9-tetrahydropyridino [3,4-b] indol-3-triformyl)-1, 2, 3-thiadiazole-5-formylhydrazine ($I_d$-2);
(1S, 3S)—N'-isonicotinoyl-1-methyl-2,3,4,9-tetrahydropyridino [3,4-b] indol-3-formylhydrazine ($I_d$-3);
(1S, 3S)—N'-benzoyl-1-methyl-2,3,4,9-tetrahydropyridino [3,4-b] indol-3-formylhydrazine ($I_d$-4);
(1S, 3S)—N'-n-hexanoyl-1-methyl-2,3,4,9-tetrahydropyridino [3,4-b] indol-3-formylhydrazine ($I_d$-5);
(1S, 3S)—N'-tert-valeryl-1-methyl-2,3,4,9-tetrahydropyridino [3,4-b] indol-3-f ormylhydrazine ($I_d$-6); and
(1S, 3S)—N'-(cyclopentyl formyl)-1-methyl-2,3,4,9-tetrahydropyridino [3,4-b] indol-3-formylhydrazine ($I_d$-7).

6. The method according to claim 4, wherein the compound effectively inhibits tobacco mosaic virus, chilli virus, rice virus, tomato virus, sweet potato virus, potato virus and cucurbits virus as well as maize dwarf mosaic virus;
the compound shows bactericidal activity against 14 kinds of pathogenic bacteria, which are cucumber *fusarium wilt*, *Cercospora arachidicola*, *Macrophoma kawatsukai*, *Alternaria solani*, *Fusarium graminearumt*, potato late blight, *Sclerotinia scleotiorum*, *Botrytis cinerea*, *Rhizoctonia solani*, *Phytophthora capsici*, *Fusarium fujikuroi*, *Rhizoctonia cereali*, *Bipolaria maydis* and *Colletotrichum orbiculare*;
the compound shows activity against armyworms, cotton bollworms, corn borers and *culex pipiens*.

7. The method according to claim 5, wherein the compound effectively inhibits tobacco mosaic virus, chilli virus, rice virus, tomato virus, sweet potato virus, potato virus and cucurbits virus as well as maize dwarf mosaic virus;
the compound shows bactericidal activity against 14 kinds of pathogenic bacteria, which are cucumber *fusarium wilt*, *Cercospora arachidicola*, *Macrophoma kawatsukai*, *Alternaria solani*, *Fusarium graminearumt*, potato late blight, *Sclerotinia scleotiorum*, *Botrytis cinerea*, *Rhizoctonia solani*, *Phytophthora capsici*, *Fusarium fujikuroi*, *Rhizoctonia cereali*, *Bipolaria maydis* and *Colletotrichum orbiculare*;
the compound shows activity against armyworms, cotton bollworms, corn borers and *culex pipiens*.

8. The method according to claim 3, wherein the method for preparing $I_b$-15 comprises the steps of:
reacting methyl ester $I_b$-7 with hydrazine hydrate (80%) to obtain compound $I_b$-15:

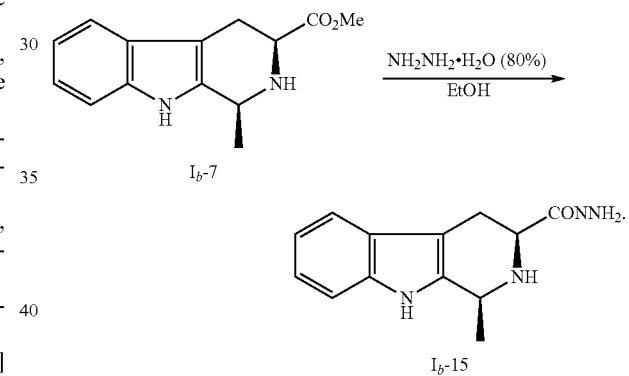

9. The method according to claim 8, wherein the method for preparing $I_b$-7 comprises the steps of:
reacting L-tryptophan with an acetaldehyde aqueous solution to obtain cyclization product $I_b$-1, which is then further esterified by one step to obtain compound $I_b$-7,

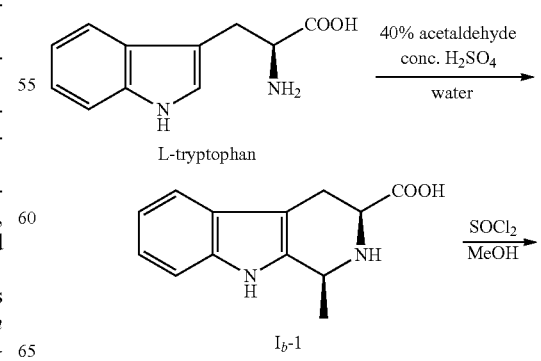

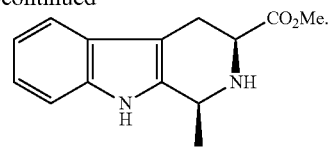
I$_b$-7
* * * * *